US008945552B2

(12) United States Patent
Baehner et al.

(10) Patent No.: US 8,945,552 B2
(45) Date of Patent: Feb. 3, 2015

(54) BISPECIFIC, BIVALENT ANTI-VEGF/ANTI-ANG-2 ANTIBODIES

(75) Inventors: Monika Baehner, Munich (DE); Sabine Imhof-Jung, Planegg (DE); Anita Kavlie, Oslo (NO); Hubert Kettenberger, Munich (DE); Christian Klein, Bonstetten (CH); Joerg Thomas, Munich (DE); Wolfgang Schaefer, Mannhein (DE); Kay-Gunnar Stubenrauch, Penzberg (DE); Markus Thomas, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 344 days.

(21) Appl. No.: 13/071,127

(22) Filed: Mar. 24, 2011

(65) Prior Publication Data

US 2011/0236388 A1    Sep. 29, 2011

(30) Foreign Application Priority Data

Mar. 26, 2010 (GB) ................................. 10003269.7

(51) Int. Cl.
*A61K 39/395* (2006.01)
*C07K 16/22* (2006.01)
*A61K 39/00* (2006.01)

(52) U.S. Cl.
CPC ............ *C07K 16/22* (2013.01); *A61K 2039/505* (2013.01); *C07K 2317/31* (2013.01); *C07K 2317/73* (2013.01); *C07K 2317/76* (2013.01); *C07K 2317/92* (2013.01); *C07K 2317/94* (2013.01)
USPC ....................... 424/136.1; 435/328; 530/387.3

(58) Field of Classification Search
None
See application file for complete search history.

(56) References Cited

U.S. PATENT DOCUMENTS

| 5,202,238 | A | 4/1993 | Fell, Jr. et al. |
| 5,204,244 | A | 4/1993 | Fell et al. |
| 6,166,185 | A | 12/2000 | Davis et al. |
| 6,897,044 | B1 | 5/2005 | Braslawsky et al. |
| 7,129,330 | B1 | 10/2006 | Little et al. |
| 8,268,314 | B2 * | 9/2012 | Baehner et al. ............ 424/136.1 |
| 2003/0064053 | A1 | 4/2003 | Liu et al. |
| 2003/0124129 | A1 | 7/2003 | Oliner |
| 2005/0079170 | A1 | 4/2005 | Le Gall et al. |
| 2006/0018909 | A1 | 1/2006 | Oliner et al. |
| 2006/0122370 | A1 | 6/2006 | Oliner et al. |
| 2006/0246071 | A1 | 11/2006 | Green et al. |
| 2006/0280747 | A1 | 12/2006 | Fuh et al. |
| 2007/0141065 | A1 | 6/2007 | Fuh et al. |
| 2009/0162360 | A1 | 6/2009 | Klein et al. |
| 2010/0111967 | A1 * | 5/2010 | Baehner et al. ............ 424/158.1 |
| 2012/0321627 | A1 * | 12/2012 | Baehner et al. ............ 424/136.1 |

FOREIGN PATENT DOCUMENTS

| EP | 1 870 459 A1 | 12/2007 |
| WO | 93/06217 A1 | 4/1993 |
| WO | 94/10202 A1 | 5/1994 |
| WO | 95/09917 A1 | 4/1995 |
| WO | 96/27011 A1 | 9/1996 |
| WO | 97/01580 A1 | 1/1997 |
| WO | 98/45331 A2 | 10/1998 |
| WO | 98/45332 A2 | 10/1998 |
| WO | 99/37791 A1 | 7/1999 |
| WO | 00/35956 A1 | 6/2000 |
| WO | 01/77342 | 10/2001 |
| WO | 03/020906 A2 | 3/2003 |
| WO | 03/030833 A2 | 4/2003 |
| WO | 03/057134 A2 | 7/2003 |
| WO | 03/106501 A1 | 12/2003 |
| WO | 2005/000900 A1 | 1/2005 |
| WO | 2005/044853 A2 | 5/2005 |
| WO | 2006/002058 A2 | 1/2006 |
| WO | 2006/031370 A2 | 3/2006 |
| WO | 2006/045049 | 4/2006 |
| WO | 2006/068953 A2 | 6/2006 |
| WO | 2006/093794 A1 | 9/2006 |
| WO | 2007/024715 A9 | 3/2007 |
| WO | 2007/044887 A2 | 4/2007 |
| WO | 2007/068895 | 6/2007 |
| WO | 2007/089445 | 8/2007 |
| WO | 2007/109254 A2 | 9/2007 |
| WO | 2008/077077 A2 | 6/2008 |
| WO | 2008/132568 A2 | 11/2008 |
| WO | 2009/032782 A2 | 3/2009 |
| WO | 2009/058812 | 5/2009 |
| WO | 2009/068649 | 6/2009 |
| WO | 2009/080251 A1 | 7/2009 |
| WO | 2009/080252 A1 | 7/2009 |
| WO | 2009/080253 A1 | 7/2009 |
| WO | 2009/080254 | 7/2009 |
| WO | 2009/134776 | 11/2009 |
| WO | 2009/142460 A2 | 11/2009 |
| WO | 2010/040508 | 4/2010 |

OTHER PUBLICATIONS

Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Schaefer et al. (PNAS 108(27):11187-11192 (Jul. 5, 2011).*
Brown et al., "A Human Monoclonal Anti-ANG2 Antibody Leads to Broad Antitumor Activity in Combination with VEGF Inhibitors and Chemotherapy Agents in Preclinical Models" Molecular Cancer Therapeutics 9(1):145-156 (Jan. 2010).
Ridgway et al., "Knobs-into-holes' Engineering of Antibody CH3 Domains for Heavy Chain Heterodimerization" Protein Engineering 9(7):617-621 ( 1996).

(Continued)

*Primary Examiner* — Lynn Bristol
(74) *Attorney, Agent, or Firm* — Janet M. Martineau

(57) ABSTRACT

The present invention relates to bispecific, bivalent antibodies against human vascular endothelial growth factor (VEGF/VEGF-A) and against human angiopoietin-2 (ANG-2), methods for their production, pharmaceutical compositions containing said antibodies, and uses thereof.

12 Claims, 14 Drawing Sheets

(56) References Cited

OTHER PUBLICATIONS

Fischer et al., "Bispecific Antibodies: Molecules that Enable Novel Therapuetic Strategies" Pathobiology 74:3-14 ( 2007).

Morrison, "A New Design for Bispecific Antibodies Enables Efficient Production of Stable Molecules with Good Pharmacodynamic Properties" Nature Biotechnology 25(11):1233-1234 ( 2007).

Xie et al., "A new format of Bispecific Antibody: Highly Efficient Heterodimerization, Expression and Tumor Cell Lysis" Journal of Immunological Methods 296:95-101 ( 2005).

Simon et al., "Antibody Domain Mutants Demostrate Autonomy of the Antigen Binding Site" EMBO Journal 9(4):1051-1056 ( 1990).

Morrison et al., "Variable Region Domain Exchange Influences the Functional Properties of IgG" Journal of Immunology 160:2802-2808 ( 1998).

Miller et al., "Design, Construction, and in Vitro Analyses of Multivalent Antibodies" Journal of Immunology 170:4854-4861 ( 2003).

Merchant et al., "An Efficient Route to Human Bispecific IgG" Nature Biotehcnology 16:677-681 ( 1998).

Borgstrom et al., "Complete Inhibition of Angiogenesis and Growth of Microtumors by Anti-Vascular Endothelial Growth Factor Neutralizing Antibody: Novel Concerts of Angiostatic Therapy from Intravital Videomicrocopy" Cancer Research 56:4032-4039 ( 1996).

Liang et al., "Molecular Basis of Cell and Developmental Biology;" Journal of Biological Chemistry 281:951-961 ( 2006).

Coloma et al., "Design and Production of Novel Tetravalent Bispecific Antibodies" Nature Biotechnology 15:159-163 ( 1997).

Melnyk et al., "Vascular Endothelial Growth Factor Promotes Tumor Dissemination by a Mechanism Distinct from its Effect on Primary Tumor Growth" Cancer Research 56:921-924 ( 1996).

Atwell et al., "Stable Heterodimers from Remodeling the Domain Interface of a Homodimer using a Phage Display Library" Journal of Mol. Biol. 270:26-35 ( 1997).

Jendreyko et al., "Simultaneous, Phenotypic Knockout of VEGF-R2 and Tie-2 with an Intradiabody Enhances Antiangiogenic Effects in Vivo" Klinische Padiatrie 218:143-151 ( 2006).

Shen et al., "single Variable Domain Antibody as a Versatile Buildin Block for the Construction of IgG-like Bispecific Antibodies" Journal of Immunological Methods 318:65-74 ( 2007).

Chan et al., "Variable Region Domain Echange in Human IgGs Promotes Antibody Complex Formation with Accompanying Structural Changes and Altered Affector Functions" Molecular Immunology 41:527-538 ( 2004).

Schoonjans et al., "Fab Chanins as an Efficient Heterodimerization Scaffold for the Production of Recombinant Bispecific and Trispecific Antibody Dervatives" Journal of Immunology 165:7050-7057 ( 2000), Kim et al , "Inhibition of Vascular Endothelial Growth Factor-Induced Angiogenesis Suppresses Tumour Growth in Vivo" Nature 362:841-844 ( 1993).

Morrison et al., "Chimeric Human Antibody Molecules: Mouse Antigen-Binding Domains with Human Constant Region Domains" Proc. Natl. Acad. Science USA 81:6851-6855 ( 1984).

Warren et al., "Regulation by Vascular Endothelial Growth Factor of Human Colon Cancer Tumorigenesis in a Mouse Model of Experimental Liver Metastasis" Journal of Clinical Investigation 95:1789-1797 ( 1995).

Wu et al., "Simultaneous Targeting of Multiple Disease Mediators by a Dual-variable-domain Immunoglobulin" Nature Biotechnology 25(11):1290-1297 ( 2007).

Jendreyko et al., "Phenotypic Knockout of VEGF-R2 and Tie-2 with an Intradiabody Reduces Tumor Growth and Angiogenesis in Vivo" PNAS 102(23):8293-8298 ( 2005).

Oliner et al., "Suppression of Angiogenesis and Tumor Growth by Selective Inhibition of Angiopoietin-2" Cancer Cell 6(5):507-516 ( 2004).

Chan et al., "Therapeutic antibodies for autoimmunity and inflammation" Nature Reviews :Immunology 10:301-316 (May 2010).

Carter, "Bispecific human IgG by design" J Immunol Methods 248(1-2):7-15 (Feb. 1, 2001).

Schaefer et al., "Immunoglobulin domain crossover as a generic approach for the production of bispecific IgG antibodies" Proceedings of the National Academy of Sciences 108(27):11187-11192 (Jul. 5, 2011).

Mabry et al., "Engineering of stable bispecific antibodies targeting IL-17A and IL-23" Protein Engineering, Design & Selection 23(3):115-127 ( 2010).

The Merck Index, An encyclopedia of Chemicals, Drugs, and Biologicals Maryadale J. O'Neil, 14th Edition Edition, Whitehouse Station, NJ USA: Merck Research Laboratories, Division of Merck & Co, Inc.,:pp. 26-27 ( 2006).

White et al., "Antibody-targeted immunotherapy for treatment of malignancy" Ann Rev Med 52:125-145 ( 2001).

\* cited by examiner

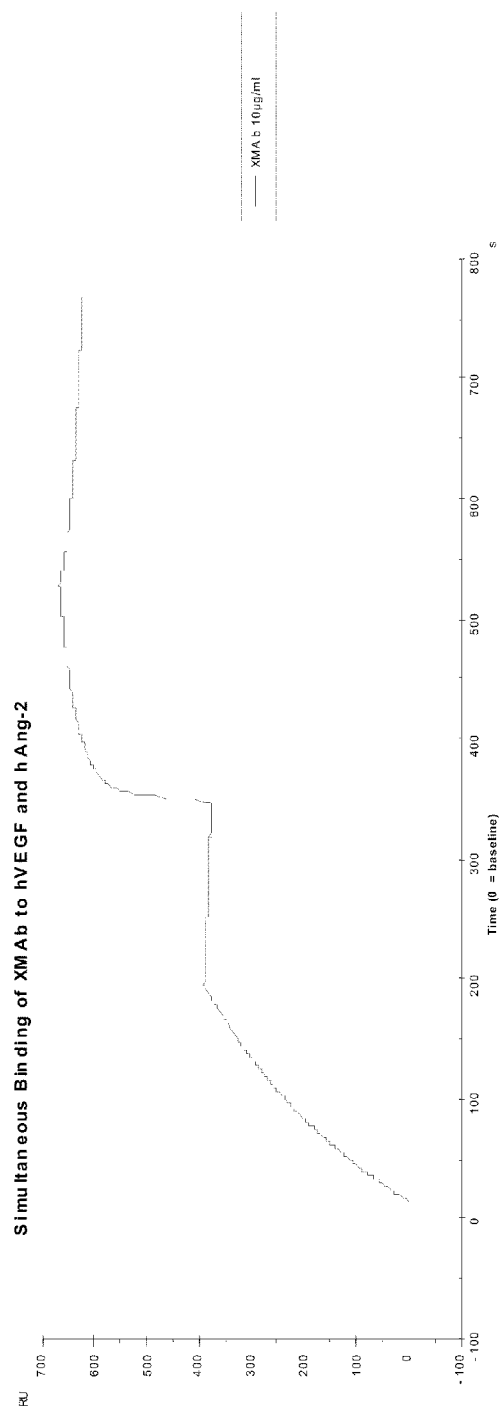

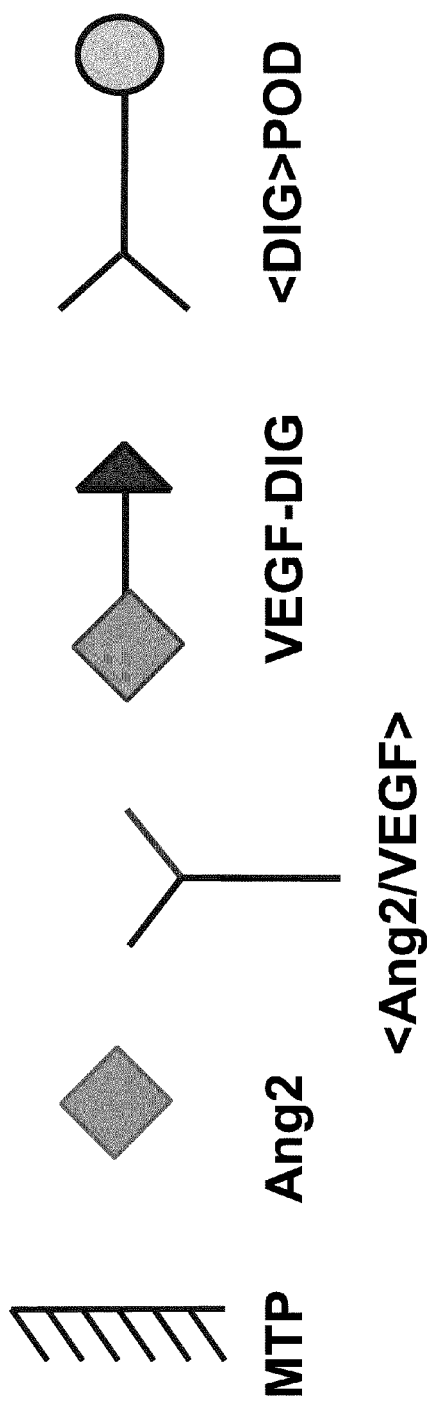

BISPECIFIC, BIVALENT ANTI-VEGF/ANTI-ANG-2 ANTIBODIES

RELATED APPLICATION

This application claims priority to and the benefit of European Application No. 10003269.7 filed Mar. 26, 2010, the contents of which is incorporated herein by reference.

FIELD OF THE INVENTION

The present invention relates to bispecific, bivalent antibodies against human vascular endothelial growth factor (VEGF/VEGF-A) and against human angiopoietin-2 (ANG-2), methods for their production, pharmaceutical compositions containing said antibodies, and uses thereof.

BACKGROUND OF THE INVENTION

Angiogenesis is implicated in the pathogenesis of a variety of disorders which include solid tumors, intraocular neovascular syndromes such as proliferative retinopathies or age-related macular degeneration (AMD), rheumatoid arthritis, and psoriasis (Folkman, J., et al., J. Biol. Chem. 267 (1992) 10931-10934; Klagsbrun, M., et al., Annu Rev. Physiol. 53 (1991) 217-239; and Garner, A., Vascular diseases, in: Pathobiology of ocular disease, A dynamic approach, Garner, A., and Klintworth, G. K. (eds.), 2nd edition, Marcel Dekker, New York (1994), pp. 1625-1710). In the case of solid tumors, the neovascularization allows the tumor cells to acquire a growth advantage and proliferative autonomy compared to the normal cells. Accordingly, a correlation has been observed between density of microvessels in tumor sections and patient survival in breast cancer as well as in several other tumors (Weidner, N., et al., N Engl J. Med. 324 (1991) 1-8; Horak, E. R., et al., Lancet 340 (1992) 1120-1124; and Macchiarini, P., et al., Lancet 340 (1992) 145-146).

VEGF and Anti-VEGF Antibodies

Human vascular endothelial growth factor (VEGF/VEGF-A) (SEQ ID No: 105) is described in e.g. Leung, D. W., et al., Science 246 (1989) 1306-9; Keck, P. J., et al., Science 246 (1989) 1309-12 and Connolly, D. T., et al., J. Biol. Chem. 264 (1989) 20017-24. VEGF is involved in the regulation of normal and abnormal angiogenesis and neovascularization associated with tumors and intraocular disorders (Ferrara, N., et al., Endocr. Rev. 18 (1997) 4-25; Berkman, R. A., et al., J. Clin. Invest. 91 (1993) 153-159; Brown, L. F., et al., Human Pathol. 26 (1995) 86-91; Brown, L. F., et al., Cancer Res. 53 (1993) 4727-4735; Mattern, J., et al., Brit. J. Cancer. 73 (1996) 931-934; and Dvorak, H. F., et al., Am. J. Pathol. 146 (1995) 1029-1039). VEGF is a homodimeric glycoprotein that has been isolated from several sources. VEGF shows highly specific mitogenic activity for endothelial cells. VEGF has important regulatory functions in the formation of new blood vessels during embryonic vasculogenesis and in angiogenesis during adult life (Carmeliet, P., et al., Nature, 380 (1996) 435-439; Ferrara, N., et al., Nature, 380 (1996) 439-442; reviewed in Ferrara, N., et al., Endocr. Rev. 18 (1997) 4-25. The significance of the role played by VEGF has been demonstrated in studies showing that inactivation of a single VEGF allele results in embryonic lethality due to failed development of the vasculature (Carmeliet, P., et al., Nature, 380 (1996) 435-439; Ferrara, N., et al., Nature, 380 (1996) 439-442. In addition VEGF has strong chemoattractant activity towards monocytes, can induce the plasminogen activator and the plasminogen activator inhibitor in endothelial cells, and can also induce microvascular permeability. Because of the latter activity, it is sometimes referred to as vascular permeability factor (VPF). The isolation and properties of VEGF have been reviewed; see Ferrara, N., et al., J. Cellular Biochem., 47 (1991) 211-218 and Connolly, D. T., J. Cellular Biochem., 47 (1991) 219-223. Alternative mRNA splicing of a single VEGF gene gives rise to five isoforms of VEGF.

Anti-VEGF neutralizing antibodies suppress the growth of a variety of human tumor cell lines in mice (Kim, K. J., et al., Nature 362 (1993) 841-844; Warren, S. R., et al., J. Clin. Invest. 95 (1995) 1789-1797; Borgstrom, P., et al., Cancer Res. 56 (1996) 4032-4039; and Melnyk, 0., et al., Cancer Res. 56 (1996) 921-924). WO 94/10202, WO 98/45332, WO 2005/00900 and WO 00/35956 refer to antibodies against VEGF. Humanized monoclonal antibody bevacizumab (sold under the trade name Avastin®) is an anti-VEGF antibody used in tumor therapy WO 98/45331).

Ranibizumab (trade name Lucentis®) is a monoclonal antibody fragment derived from the same parent murine antibody as bevacizumab (Avastin). It is much smaller than the parent molecule and has been affinity matured to provide stronger binding to VEGF-A (WO 98/45331). It is an anti-angiogenic that has been approved to treat the "wet" type of age-related macular degeneration (ARMD), a common form of age-related vision loss. Another anti-VEGF antibody is e.g. HuMab G6-31 described e.g. in US 2007/0141065.

ANG-2 and Anti-ANG-2 Antibodies

Human angiopoietin-2 (ANG-2) (alternatively abbreviated with ANGPT2 or ANG2) (SEQ ID No: 106) is described in Maisonpierre, P. C., et al, Science 277 (1997) 55-60 and Cheung, A. H., et al., Genomics 48 (1998) 389-91. The angiopoietins-1 and -2 (ANG-1 (SEQ ID No: 107) and ANG-2 (SEQ ID No: 106)) were discovered as ligands for the Ties, a family of tyrosine kinases that is selectively expressed within the vascular endothelium. Yancopoulos, G. D., et al., Nature 407 (2000) 242-48. There are now four definitive members of the angiopoietin family. Angiopoietin-3 and -4 (Ang-3 and Ang-4) may represent widely diverged counterparts of the same gene locus in mouse and man. Kim, I., et al., FEBS Let, 443 (1999) 353-56; Kim, I., et al., J Biol Chem 274 (1999) 26523-28. ANG-1 and ANG-2 were originally identified in tissue culture experiments as agonist and antagonist, respectively (see for ANG-1: Davis, S., et al., Cell 87 (1996) 1161-69; and for ANG-2: Maisonpierre, P. C., et al., Science 277 (1997) 55-60) All of the known angiopoietins bind primarily to Tie2, and both Ang-1 and -2 bind to Tie2 with an affinity of 3 nM (Kd). Maisonpierre, P. C., et al., Science 277 (1997) 55-60. Ang-1 was shown to support EC survival and to promote endothelium integrity, Davis, S., et al., Cell 87 (1996) 1161-69; Kwak, H. J., et al., FEBS Lett 448 (1999) 249-53; Suri, C., et al., Science 282 (1998) 468-71; Thurston, G., et al., Science 286 (1999) 2511-2514; Thurston, G., et al., Nat. Med. 6 (2000) 460-63, whereas ANG-2 had the opposite effect and promoted blood vessel destabilization and regression in the absence of the survival factors VEGF or basic fibroblast growth factor. Maisonpierre, P. C., et al., Science 277 (1997) 55-60. However, many studies of ANG-2 function have suggested a more complex situation. ANG-2 might be a complex regulator of vascular remodeling that plays a role in both vessel sprouting and vessel regression. Supporting such roles for ANG-2, expression analyses reveal that ANG-2 is rapidly induced, together with VEGF, in adult settings of angiogenic sprouting, whereas ANG-2 is induced in the absence of VEGF in settings of vascular regression. Holash, J., et al., Science 284 (1999) 1994-98; Holash, J., et al., Oncogene 18 (1999) 5356-62. Consistent with a context-dependent role, ANG-2 specifically binds to the same endothelial-specific receptor, Tie-2, which is activated by Ang-1, but has context-dependent effects on its activation. Maisonpierre, P. C., et al., Science 277 (1997) 55-60.

Corneal angiogenesis assays have shown that both ANG-1 and ANG-2 had similar effects, acting synergistically with VEGF to promote growth of new blood vessels. Asahara, T., et al., Circ. Res. 83 (1998) 233-40. The possibility that there was a dose-dependent endothelial response was raised by the observation that in vitro at high concentration, ANG-2 can also be pro-angiogenic. Kim, I., et al., Oncogene 19 (2000) 4549-52. At high concentration, ANG-2 acts as an apoptosis survival factor for endothelial cells during serum deprivation apoptosis through activation of Tie2 via PI-3 Kinase and Akt pathway. Kim, I., et al., Oncogene 19 (2000) 4549-52.

Other in vitro experiments suggested that during sustained exposure, the effects of ANG-2 may progressively shift from that of an antagonist to an agonist of Tie2, and at later time points, it may contribute directly to vascular tube formation and neovessel stabilization. Teichert-Kuliszewska, K., et al., Cardiovasc. Res. 49 (2001) 659-70. Furthermore, if ECs were cultivated on fibrin gel, activation of Tie2 with ANG-2 was also observed, perhaps suggesting that the action of ANG-2 could depend on EC differentiation state. Teichert-Kuliszewska, K., et al., Cardiovasc. Res. 49 (2001) 659-70. In microvascular EC cultured in a three-dimensional collagen gel, ANG-2 can also induce Tie2 activation and promote formation of capillary-like structures. Mochizuki, Y., et al., J. Cell. Sci. 115 (2002) 175-83. Use of a 3-D spheroidal coculture as an in-vitro model of vessel maturation demonstrated that direct contact between ECs and mesenchymal cells abrogates responsiveness to VEGF, whereas the presence of VEGF and ANG-2 induced sprouting. Korff, T., et al., Faseb J. 15 (2001) 447-57. Etoh, T. H. et al. demonstrated that ECs that constitutively express Tie2, the expression of MMP-1, -9 and u-PA were strongly upregulated by ANG-2 in the presence of VEGF. Etoh, T., et al., Cancer Res. 61 (2001) 2145-53. With an in vivo pupillary membrane model, Lobov, I. B. et al. showed that ANG-2 in the presence of endogenous VEGF promotes a rapid increase in capillary diameter, remodeling of the basal lamina, proliferation and migration of endothelial cells, and stimulates sprouting of new blood vessels. Lobov, I. B., et al., Proc. Natl. Acad. Sci. USA 99 (2002) 11205-10. By contrast, ANG-2 promotes endothelial cell death and vessel regression without endogenous VEGF. Lobov, I. B., et al., Proc. Natl. Acad. Sci. USA 99 (2002) 11205-10. Similarly, with an in vivo tumor model, Vajkoczy, P., et al. demonstrated that multicellular aggregates initiate vascular growth by angiogenic sprouting via the simultaneous expression of VEGFR-2 and ANG-2 by host and tumor endothelium. Vajkoczy, P., et al., J. Clin. Invest. 109 (2002) 777-85. This model illustrated that the established microvasculature of growing tumors is characterized by a continuous remodeling, putatively mediated by the expression of VEGF and ANG-2 (Vajkoczy, P., et al., J. Clin. Invest. 109 (2002) 777-85).

Knock-out mouse studies of Tie-2 and Angiopoietin-1 show similar phenotypes and suggest that Angiopoietin-1 stimulated Tie-2 phosphorylation mediates remodeling and stabilization of developing vessel, promoting blood vessel maturation during angiogenesis and maintenance of endothelial cell-support cell adhesion (Dumont, D. J., et al., Genes & Development, 8 (1994) 1897-1909; Sato, T. N., Nature, 376 (1995) 70-74; (Thurston, G., et al., Nature Medicine 6 (2000) 460-463). The role of Angiopoietin-1 is thought to be conserved in the adult, where it is expressed widely and constitutively (Hanahan, D., Science, 277 (1997) 48-50; Zagzag, D., et al., Exp Neurology 159 (1999) 391-400). In contrast, Angiopoietin-2 expression is primarily limited to sites of vascular remodeling where it is thought to block the constitutive stabilizing or maturing function of Angiopoietin-1, allowing vessels to revert to, and remain in, a plastic state which may be more responsive to sprouting signals (Hanahan, D., 1997; Holash, J., et al., Oncogene 18 (199) 5356-62; Maisonpierre, P. C., 1997). Studies of Angiopoietin-2 expression in pathological angiogenesis have found many tumor types to show vascular Angiopoietin-2 expression (Maisonpierre, P. C., et al., Science 277 (1997) 55-60). Functional studies suggest Angiopoietin-2 is involved in tumor angiogenesis and associate Angiopoietin-2 overexpression with increased tumor growth in a mouse xenograft model (Ahmad, S. A., et al., Cancer Res., 61 (2001) 1255-1259). Other studies have associated Angiopoietin-2 overexpression with tumor hypervascularity (Etoh, T., et al., Cancer Res. 61 (2001) 2145-53; Tanaka, F., et al., Cancer Res. 62 (2002) 7124-7129).

In recent years Angiopoietin-1, Angiopoietin-2 and/or Tie-2 have been proposed as possible anti-cancer therapeutic targets. For example U.S. Pat. No. 6,166,185, U.S. Pat. No. 5,650,490 and U.S. Pat. No. 5,814,464 each disclose anti-Tie-2 ligand and receptor antibodies. Studies using soluble Tie-2 were reported to decrease the number and size of tumors in rodents (Lin, 1997; Lin 1998). Siemeister, G., et al., Cancer Res. 59:3 (1999) 3185-91 generated human melanoma cell lines expressing the extracellular domain of Tie-2, injected these into nude mice and reported soluble Tie-2 to result in significant inhibition of tumor growth and tumor angiogenesis. Given both Angiopoietin-1 and Angiopoietin-2 bind to Tie-2, it is unclear from these studies whether Angiopoietin-1, Angiopoietin-2 or Tie-2 would be an attractive target for anti-cancer therapy. However, effective anti-Angiopoietin-2 therapy is thought to be of benefit in treating diseases such as cancer, in which progression is dependant on aberrant angiogenesis where blocking the process can lead to prevention of disease advancement (Folkman, J., Nature Medicine. 1 (1995) 27-31).

In addition some groups have reported the use of antibodies and peptides that bind to Angiopoietin-2. See, for example, U.S. Pat. No. 6,166,185 and US 2003/10124129. WO 03/030833, WO 2006/068953, WO 03/057134 or US 2006/0122370.

Study of the effect of focal expression of Angiopoietin-2 has shown that antagonizing the Angiopoietin-1/Tie-2 signal loosens the tight vascular structure thereby exposing ECs to activating signals from angiogenesis inducers, e.g. VEGF (Hanahan, D., Science, 277 (1997) 48-50). This pro-angiogenic effect resulting from inhibition of Angiopoietin-1 indicates that anti-Angiopoietin-1 therapy would not be an effective anti-cancer treatment.

ANG-2 is expressed during development at sites where blood vessel remodeling is occurring. Maisonpierre, P. C., et al., Science 277 (1997) 55-60. In adult individuals, ANG-2 expression is restricted to sites of vascular remodeling as well as in highly vascularized tumors, including glioma, Osada, H., et al., Int. J. Oncol. 18 (2001) 305-09); Koga, K., et al., Cancer Res. 61 (2001) 6248-54, hepatocellular carcinoma, Tanaka, S., et al., J. Clin. Invest. 103 (1999) 341-45, gastric carcinoma, Etoh, T., et al., Cancer Res. 61 (2001) 2145-53; Lee, J. H., et al., Int. J. Oncol. 18 (2001) 355-61, thyroid tumor, Bunone, G., et al., Am J Pathol 155 (1999) 1967-76 non-small cell lung cancer, Wong, M. P., et al., Lung Cancer 29 (2000) 11-22, and cancer of colon, Ahmad, S. A., et al., Cancer 92 (2001) 1138-43, and prostate Wurmbach, J. H., et al., Anticancer Res. 20 (2000) 5217-20. Some tumor cells are found to express ANG-2. For example, Tanaka, S., et al., J. Clin. Invest. 103 (1999) 341-45 detected ANG-2 mRNA in 10 out of 12 specimens of human hepatocellular carcinoma (HCC). Ellis' group reported that ANG-2 is expressed ubiquitously in tumor epithelium. Ahmad, S. A., et al., Cancer 92 (2001) 1138-43. Other investigators reported similar findings. Chen, L., et al., J. Tongji Med. Univ. 21 (2001) 228-35. By detecting ANG-2 mRNA levels in archived human breast cancer specimens, Sfiligoi, C., et al., Int. J. Cancer 103 (2003) 466-74 reported that ANG-2 mRNA is significantly associated with auxiliary lymph node invasion, short disease-free time and poor overall survival. Tanaka, F., et al., Cancer Res. 62 (2002) 7124-29 reviewed a total of 236 patients of non-small cell lung cancer (NSCLC) with pathological stage-I to -IIIA, respectively. Using immunohistochemistry, they found that 16.9% of the NSCLC patients were ANG-2 positive. The microvessel density for ANG-2 positive tumor is significantly higher than that of ANG-2 negative. Such an angiogenic effect of ANG-2 was seen only when VEGF expression was high. Moreover, positive expression of ANG-2 was a significant factor to predict a poor postoperative survival. Tanaka, F., et al., Cancer Res. 62 (2002) 7124-7129. However, they found no significant correlation between Ang-1 expression and the microvessel density. Tanaka, F., et al., Cancer Res. 62 (2002) 7124-7129. These results suggest that ANG-2 is an indicator of poor prognosis patients with several types of cancer.

Recently, using an ANG-2 knockout mouse model, Yancopoulos' group reported that ANG-2 is required for postnatal angiogenesis. Gale, N. W., et al., Dev. Cell 3 (2002) 411-23. They showed that the developmentally programmed regression of the hyaloid vasculature in the eye does not occur in the ANG-2 knockout mice and their retinal blood vessels fail to sprout out from the central retinal artery. Gale, N. W., et al., Dev. Cell 3 (2002) 411-23. They also found that deletion of ANG-2 results in profound defects in the patterning and function of the lymphatic vasculature. Gale, N. W., et al., Dev. Cell 3 (2002) 411-23. Genetic rescue with Ang-1 corrects the lymphatic, but not the angiogenesis defects. Gale, N. W., et al., Dev. Cell 3 (2002) 411-23.

Peters and his colleagues reported that soluble Tie2, when delivered either as recombinant protein or in a viral expression vector, inhibited in vivo growth of murine mammary carcinoma and melanoma in mouse models. Lin, P., et al., Proc. Natl. Acad. Sci. USA 95 (1998) 8829-34; Lin, P., et al., J. Clin. Invest. 100 (1997) 2072-78. Vascular densities in the tumor tissues so treated were greatly reduced. In addition, soluble Tie2 blocked angiogenesis in the rat corneal stimulated by tumor cell conditioned media. Lin, P., et al., J. Clin. Invest. 100 (1997) 2072-78.

Furthermore, Isner and his team demonstrated that addition of ANG-2 to VEGF promoted significantly longer and more circumferential neovascularity than VEGF alone. Asahara, T., et al., Circ. Res. 83 (1998) 233-40. Excess soluble Tie2 receptor precluded modulation of VEGF-induced neovascularization by ANG-2. Asahara, T., et al., Circ. Res. 83 (1998) 233-40. Siemeister, G., et al., Cancer Res. 59:3 (1999) 3185-91 showed with nude mouse xenografts that overexpression of the extracellular ligand-binding domains of either Flt-1 or Tie2 in the xenografts results in significant inhibition of pathway could not be compensated by the other one, suggesting that the VEGF receptor pathway and the Tie2 pathway should be considered as two independent mediators essential for the process of in vivo angiogenesis. Siemeister, G., et al., Cancer Res. 59:3 (1999) 3185-91. This is proven by a more recent publication by White, R., R., et al., Proc. Natl. Acad. Sci. USA 100 (2003) 5028-33. In their study, it was demonstrated that a nuclease-resistant RNA aptamer that specifically binds and inhibits ANG-2 significantly inhibited neovascularization induced by bFGF in the rat corneal micropocket angiogenesis model.

Bispecific Antibodies

A wide variety of recombinant antibody formats have been developed in the recent past, e.g. tetravalent bispecific antibodies by fusion of, e.g., an IgG antibody format and single chain domains (see e.g. Coloma, M. J., et al., Nature Biotech 15 (1997) 159-163; WO 2001/077342; and Morrison, S. L., Nature Biotech 25 (2007) 1233-1234).

Also several other new formats wherein the antibody core structure (IgA, IgD, IgE, IgG or IgM) is no longer retained such as dia-, tria- or tetrabodies, minibodies, several single chain formats (scFv, Bis-scFv), which are capable of binding two or more antigens, have been developed (Holliger, P., et al., Nature Biotech 23 (2005) 1126-1136; Fischer, N., Leger, 0., Pathobiology 74 (2007) 3-14; Shen, J., et al., Journal of Immunological Methods 318 (2007) 65-74; Wu, C., et al., Nature Biotech. 25 (2007) 1290-1297).

All such formats use linkers either to fuse the antibody core (IgA, IgD, IgE, IgG or IgM) to a further binding protein (e.g. scFv) or to fuse e.g. two Fab fragments or scFvs (Fischer, N., Léger, O., Pathobiology 74 (2007) 3-14). It has to be kept in mind that one may want to retain effector functions, such as e.g. complement-dependent cytotoxicity (CDC) or antibody dependent cellular cytotoxicity (ADCC), which are mediated through the Fc receptor binding, by maintaining a high degree of similarity to naturally occurring antibodies.

In WO 2007/024715 are reported dual variable domain immunoglobulins as engineered multivalent and multispecific binding proteins. A process for the preparation of biologically active antibody dimers is reported in U.S. Pat. No. 6,897,044. Multivalent $F_V$ antibody construct having at least four variable domains which are linked with each over via peptide linkers are reported in U.S. Pat. No. 7,129,330. Dimeric and multimeric antigen binding structures are reported in US 2005/0079170. Tri- or tetra-valent monospecific antigen-binding protein comprising three or four Fab fragments bound to each other covalently by a connecting structure, which protein is not a natural immunoglobulin are reported in U.S. Pat. No. 6,511,663. In WO 2006/020258 tetravalent bispecific antibodies are reported that can be efficiently expressed in prokaryotic and eukaryotic cells, and are useful in therapeutic and diagnostic methods. A method of separating or preferentially synthesizing dimers which are linked via at least one interchain disulfide linkage from dimers which are not linked via at least one interchain disulfide linkage from a mixture comprising the two types of polypeptide dimers is reported in US 2005/0163782. Bispecific tetravalent receptors are reported in U.S. Pat. No. 5,959,083. Engineered antibodies with three or more functional antigen binding sites are reported in WO 2001/077342.

Multispecific and multivalent antigen-binding polypeptides are reported in WO 1997/001580. WO 1992/004053 reports homoconjugates, typically prepared from monoclonal antibodies of the IgG class which bind to the same antigenic determinant are covalently linked by synthetic cross-linking Oligomeric monoclonal antibodies with high avidity for antigen are reported in WO 1991/06305 whereby the oligomers, typically of the IgG class, are secreted having two or more immunoglobulin monomers associated together to form tetravalent or hexavalent IgG molecules. Sheep-derived antibodies and engineered antibody constructs are reported in U.S. Pat. No. 6,350,860, which can be used to treat diseases wherein interferon gamma activity is pathogenic. In US 2005/0100543 are reported targetable constructs that are multivalent carriers of bi-specific antibodies, i.e., each molecule of a targetable construct can serve as a carrier of two or more bi-specific antibodies. Genetically engineered bispecific tetravalent antibodies are reported in WO 1995/009917. In WO 2007/109254 stabilized binding molecules that consist of or comprise a stabilized scFv are reported.

Combination of VEGF and ANG-2 Inhibitors

WO 2007/068895 refers to a combination of an ANG-2 antagonist and a VEGF, KDR and/or FLTL antagonists. WO 2007/089445 refers to ANG-2 and VEGF inhibitor combinations.

WO 2003/106501 refers to fusion proteins binding to Angiopoietin and containing a multimerization domain. WO 2008/132568 relates to fusion proteins binding to Angiopoietin and VEGF. WO 2003/020906 relates to multivalent protein conjugates with multiple ligand-binding domains of receptors.

WO 2009/136352 relates to anti-angiogenic compounds.

SUMMARY OF THE INVENTION

The invention is directed to a bispecific, bivalent antibody comprising a first antigen-binding site that specifically binds to human VEGF and a second antigen-binding site that specifically binds to human ANG-2, characterized in that
 i) said first antigen-binding site comprises as heavy chain variable domain (VH) the SEQ ID NO: 1, and as light chain variable domain (VL) the SEQ ID NO: 2; and
 ii) said second antigen-binding site comprises as heavy chain variable domain (VH) the SEQ ID NO: 3, and as light chain variable domain (VL) the SEQ ID NO: 4.

In one aspect of the invention the bispecific antibody according to the invention is characterized in comprising
 a) the heavy chain and the light chain of a first full length antibody that specifically binds to VEGF; and
 b) the modified heavy chain and modified light chain of a full length antibody that specifically binds to ANG-2, wherein the constant domains CL and CH1 are replaced by each other.

In one embodiment such bispecific, bivalent antibody is characterized in comprising
 a) as heavy chain of the first full length antibody the amino acid sequence of SEQ ID NO: 7, and as light chain of the first full length antibody the amino acid sequence of SEQ ID NO: 5, and
 b) as modified heavy chain of the second full length antibody the amino acid sequence of SEQ ID NO: 8, and as modified light chain of the second full length antibody the amino acid sequence of SEQ ID NO: 6.

In one embodiment such bispecific, bivalent antibody is characterized in comprising
 a) as heavy chain of the first full length antibody the amino acid sequence of SEQ ID NO: 11, and as light chain of the first full length antibody the amino acid sequence of SEQ ID NO: 9, and
 b) as modified heavy chain of the second full length antibody the amino acid sequence of SEQ ID NO: 12, and as modified light chain of the second full length antibody the amino acid sequence of SEQ ID NO: 10.

In one embodiment such bispecific, bivalent antibody is characterized in comprising
 a) as heavy chain of the first full length antibody the amino acid sequence of SEQ ID NO: 15, and as light chain of the first full length antibody the amino acid sequence of SEQ ID NO: 13, and
 b) as modified heavy chain of the second full length antibody the amino acid sequence of SEQ ID NO: 16, and as modified light chain of the second full length antibody the amino acid sequence of SEQ ID NO: 14.

Still further aspects of the invention are a pharmaceutical composition comprising said bispecific antibody, said composition for the treatment of cancer, the use of said bispecific antibody for the manufacture of a medicament for the treatment of cancer, a method of treatment of patient suffering from cancer by administering said bispecific antibody to a patient in the need of such treatment.

Still further aspects of the invention are a pharmaceutical composition comprising said bispecific antibody, said composition for the treatment of vascular diseases, the use of said bispecific antibody for the manufacture of a medicament for the treatment of vascular diseases, a method of treatment of patient suffering from vascular diseases by administering said bispecific antibody to a patient in the need of such treatment.

A further aspect of the invention is a nucleic acid molecule encoding a chain of a bispecific antibody according to the invention.

The invention further provides expression vectors containing said nucleic acid according to the invention capable of expressing said nucleic acid in a prokaryotic or eukaryotic host cell, and host cells containing such vectors for the recombinant production of a bispecific antibody according to the invention.

The invention further comprises a prokaryotic or eukaryotic host cell comprising a vector according to the invention.

The invention further comprises a method for the production of a bispecific antibody according to the invention, characterized by expressing a nucleic acid according to the invention in a prokaryotic or eukaryotic host cell and recovering said bispecific antibody from said cell or the cell culture supernatant. The invention further comprises the antibody obtained by such method for the production of a bispecific antibody.

Accordingly one embodiment of the invention is a bispecific, bivalent antibody comprising a first antigen-binding site that specifically binds to human VEGF and a second antigen-binding site that specifically binds to human ANG-2, characterized in comprising the amino acid sequences of SEQ ID NO: 5, of SEQ ID NO: 6, of SEQ ID NO: 7, and of SEQ ID NO: 8.

Accordingly one embodiment of the invention is a bispecific, bivalent antibody comprising a first antigen-binding site that specifically binds to human VEGF and a second antigen-binding site that specifically binds to human ANG-2, characterized in comprising the amino acid sequences of SEQ ID NO: 9, of SEQ ID NO: 10, of SEQ ID NO: 11, and of SEQ ID NO: 12.

Accordingly one embodiment of the invention is a bispecific, bivalent antibody comprising a first antigen-binding site that specifically binds to human VEGF and a second antigen-binding site that specifically binds to human ANG-2, characterized in comprising the amino acid sequences of SEQ ID NO: 13, of SEQ ID NO: 14, of SEQ ID NO: 15, and of SEQ ID NO: 16.

The bispecific, bivalent antibodies according to the invention show benefits for human patients in need of a VEGF and ANG-2 targeting therapy. The antibodies according to the invention have highly valuable properties causing a benefit for a patient suffering from such a disease, especially suffering from cancer. The bispecific antibodies according to the invention are highly effective in tumor growth and/or inhibition of tumor angiogenesis or vascular diseases. The bispecific, bivalent antibodies according to the invention The bispecific, bivalent <VEGF-ANG-2> antibodies according to the invention show valuable pharmacokinetic/-dynamic properties like e.g. stability, good (i.e. slow) clearance (e.g. at low doses).

The bispecific antibodies according to the invention are highly effective in
a) tumor growth inhibition (e.g. with the bispecific antibodies according to the invention tumor stasis could be achieved already at lower concentrations compared to the combination of the two monospecific antibodies (e.g. in the Colo205 and the KPL-4 tumor models of Example 9 and 10, tumor stasis was already achieved with 10 mg/kg XMAb1 compared to the combination of 10 mg/kg of ANG2i-LC06+10 mg/kg of Avastin), and/or
b) inhibition of tumor angiogenesis or vascular diseases (e.g. maximal antiangiogenic effects with the bispecific antibodies according to the invention could already be achieved at lower concentrations compared to the combination of the two monospecific antibodies (e.g. in the mouse corneal angiogenesis assay of Example 8, the maximal antiangiogenic effect was already achieved with 10 mg/kg XMAb1 compared to the combination of 10 mg/kg of ANG2i-LC06+10 mg/kg of Avastin).

DESCRIPTION OF THE FIGURES

FIG. 4 ELISA principle for quantification of binding active mAb<Ang2/VEGF> antibodies FIG. 5 Calibration curve of ELISA for quantification of binding active <Ang2/VEGF> XMab1 antibodies FIG. 6 Mouse corneal angiogenesis assay—inhibition of vessel outgrowth from the limbus towards the VEGF gradient by administration of a bispecific antibody according to the invention.

DETAILED DESCRIPTION OF THE INVENTION

The invention is directed to a bispecific, bivalent antibody comprising a first antigen-binding site that specifically binds to human VEGF and a second antigen-binding site that specifically binds to human ANG-2. characterized in that
  i) said first antigen-binding site comprises as heavy chain variable domain (VH) the SEQ ID NO: 1, and as light chain variable domain (VL) the SEQ ID NO: 2; and
  ii) said second antigen-binding site comprises as heavy chain variable domain (VH) the SEQ ID NO: 3, and as light chain variable domain (VL) the SEQ ID NO: 4.

In one aspect of the invention the bispecific antibody according to the invention is characterized in comprising
  a) the heavy chain and the light chain of a first full length antibody that specifically binds to VEGF;
  b) the modified heavy chain and modified light chain of a full length antibody that specifically binds to ANG-2, wherein the constant domains CL and CH1 are replaced by each other.

Figure 1:
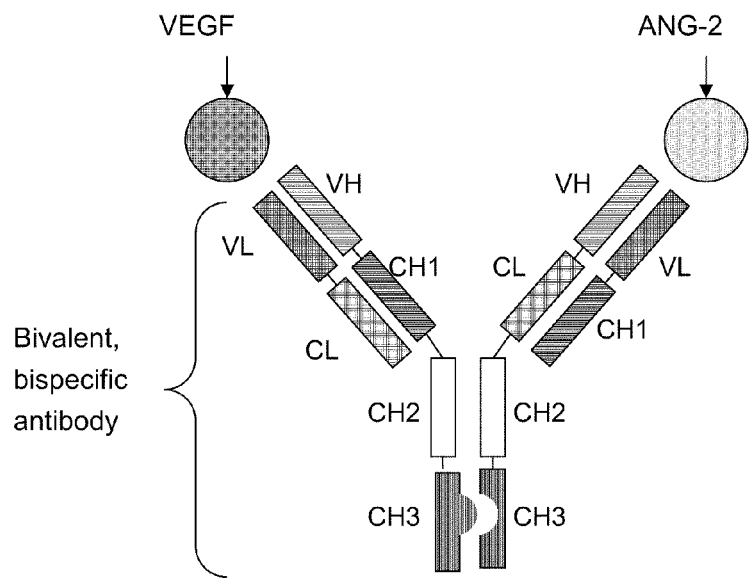
FIG. 1 Exemplary bivalent bispecific antibody format for XMab examples including Knobs-into-Holes modified CH3 domains FIG. 2a Exemplary bivalent bispecific antibody format for OAscFab examples including Knobs-into-Holes modified CH3 domains FIG. 2b Exemplary bivalent bispecific antibody format for example OAscXFab1 including Knobs-into-Holes modified CH3 domains FIG. 2c Exemplary bivalent bispecific antibody format for examples OAscXFab2 and OAscXFab3 including Knobs-into-Holes modified CH3 domains FIG. 3 Simultaneous binding of <VEGF-Ang-2> XMab1 to VEGF (1. Step) followed by binding to hAng-2 (second step)

This bispecific, bivalent antibody format for the bispecific antibody specifically binding to human vascular endothelial growth factor (VEGF) and human angiopoietin-2 (ANG-2) is described in WO 2009/080253 (see exemplary scheme in including Knobs-into-Holes modified CH3 domains in FIG. 1). The antibodies based on this bispecific, bivalent antibody format are named XMab in the examples of the current invention.

In one embodiment such bispecific, bivalent antibody is characterized in comprising
  a) as heavy chain of the first full length antibody the amino acid sequence of SEQ ID NO: 7, and as light chain of the first full length antibody the amino acid sequence of SEQ ID NO: 5, and
  b) as modified heavy chain of the second full length antibody the amino acid sequence of SEQ ID NO: 8, and as modified light chain of the second full length antibody the amino acid sequence of SEQ ID NO: 6.

In one embodiment such bispecific, bivalent antibody is characterized in comprising
  a) as heavy chain of the first full length antibody the amino acid sequence of SEQ ID NO: 11, and as light chain of the first full length antibody the amino acid sequence of SEQ ID NO: 9, and b) as modified heavy chain of the second full length antibody the amino acid sequence of SEQ ID NO: 12, and as modified light chain of the second full length antibody the amino acid sequence of SEQ ID NO: 10.

In one embodiment such bispecific, bivalent antibody is characterized in comprising
  a) as heavy chain of the first full length antibody the amino acid sequence of SEQ ID NO: 15, and as light chain of the first full length antibody the amino acid sequence of SEQ ID NO: 13, and
  b) as modified heavy chain of the second full length antibody the amino acid sequence of SEQ ID NO: 16, and as modified light chain of the second full length antibody the amino acid sequence of SEQ ID NO: 14.

In one embodiment such bispecific, bivalent antibody is characterized in comprising
  a) as heavy chain of the first full length antibody the amino acid sequence of SEQ ID NO: 19, and as light chain of the first full length antibody the amino acid sequence of SEQ ID NO: 17, and
  b) as modified heavy chain of the second full length antibody the amino acid sequence of SEQ ID NO: 20, and as modified light chain of the second full length antibody the amino acid sequence of SEQ ID NO: 18.

In one embodiment such bispecific, bivalent antibody is characterized in comprising
  a) as heavy chain of the first full length antibody the amino acid sequence of SEQ ID NO: 23, and as light chain of the first full length antibody the amino acid sequence of SEQ ID NO: 21, and
  b) as modified heavy chain of the second full length antibody the amino acid sequence of SEQ ID NO: 24, and as modified light chain of the second full length antibody the amino acid sequence of SEQ ID NO: 22.

In one embodiment such bispecific, bivalent antibody is characterized in comprising
  a) as heavy chain of the first full length antibody the amino acid sequence of SEQ ID NO: 27, and as light chain of the first full length antibody the amino acid sequence of SEQ ID NO: 25, and
  b) as modified heavy chain of the second full length antibody the amino acid sequence of SEQ ID NO: 28, and as modified light chain of the second full length antibody the amino acid sequence of SEQ ID NO: 26.

Accordingly one embodiment of the invention is a bispecific, bivalent antibody comprising a first antigen-binding site that specifically binds to human VEGF and a second antigen-binding site that specifically binds to human ANG-2, characterized in comprising the amino acid sequences of SEQ ID NO: 5, of SEQ ID NO: 6, of SEQ ID NO: 7, and of SEQ ID NO: 8.

Accordingly one embodiment of the invention is a bispecific, bivalent antibody comprising a first antigen-binding site that specifically binds to human VEGF and a second antigen-binding site that specifically binds to human ANG-2, characterized in comprising the amino acid sequences of SEQ ID NO: 9, of SEQ ID NO: 10, of SEQ ID NO: 11, and of SEQ ID NO: 12.

Accordingly one embodiment of the invention is a bispecific, bivalent antibody comprising a first antigen-binding site that specifically binds to human VEGF and a second antigen-binding site that specifically binds to human ANG-2, characterized in comprising the amino acid sequences of SEQ ID NO: 13, of SEQ ID NO: 14, of SEQ ID NO: 15, and of SEQ ID NO: 16.

Accordingly one embodiment of the invention is a bispecific, bivalent antibody comprising a first antigen-binding site that specifically binds to human VEGF and a second antigen-binding site that specifically binds to human ANG-2, characterized in comprising the amino acid sequences of SEQ ID NO: 17, of SEQ ID NO: 18, of SEQ ID NO: 19, and of SEQ ID NO: 20.

Accordingly one embodiment of the invention is a bispecific, bivalent antibody comprising a first antigen-binding site that specifically binds to human VEGF and a second antigen-binding site that specifically binds to human ANG-2, characterized in comprising the amino acid sequences of SEQ ID NO: 21, of SEQ ID NO: 22, of SEQ ID NO: 23, and of SEQ ID NO: 24.

Accordingly one embodiment of the invention is a bispecific, bivalent antibody comprising a first antigen-binding site that specifically binds to human VEGF and a second antigen-binding site that specifically binds to human ANG-2, characterized in comprising the amino acid sequences of SEQ ID NO: 25, of SEQ ID NO: 26, of SEQ ID NO: 27, and of SEQ ID NO: 28.

In another aspect of the invention the bispecific antibody according to the invention is characterized in comprising
  a) the heavy chain and the light chain of a first full length antibody that specifically binds to VEGF;
  b) the heavy chain and the light chain of a second full length antibody that specifically binds to ANG-2, wherein the N-terminus of the heavy chain is connected to the C-terminus of the light chain via a peptide linker.

Figure 2A:
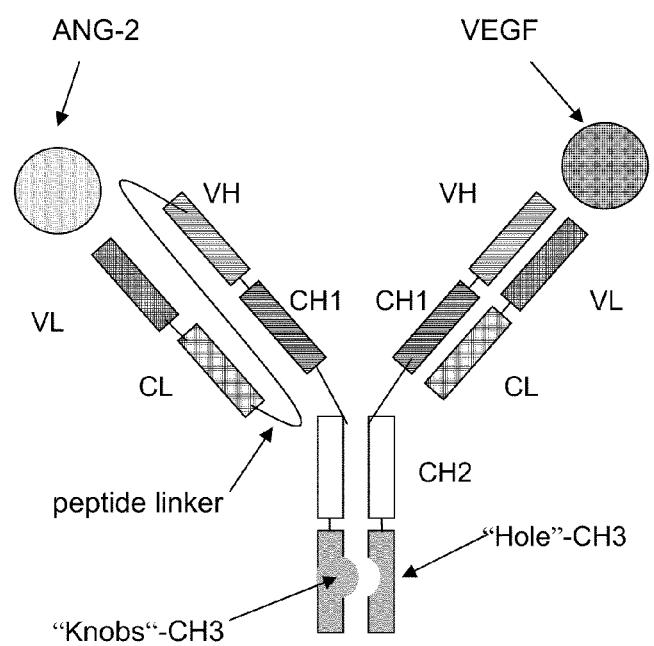

An exemplary scheme of this bispecific, bivalent antibody format for this bispecific antibody specifically binding to human vascular endothelial growth factor (VEGF) and human angiopoietin-2 (ANG-2) is shown in FIG. 2a including Knobs-into. Holes modified CH3 domains. The antibodies based on this bispecific, bivalent antibody format are named OAscFab in the examples of the current invention.

In one embodiment such bispecific, bivalent antibody is characterized in comprising
  a) as heavy chain of the first full length antibody the amino acid sequence of SEQ ID NO: 30, and as light chain of the first full length antibody the amino acid sequence of SEQ ID NO: 31, and
  b) as heavy chain of the second full length antibody connected to the light chain of the second full length antibody via a peptide linker the amino acid sequence of SEQ ID NO: 29.

In one embodiment such bispecific, bivalent antibody is characterized in comprising
  a) as heavy chain of the first full length antibody the amino acid sequence of SEQ ID NO: 33, and as light chain of the first full length antibody the amino acid sequence of SEQ ID NO: 34, and
  b) as heavy chain of the second full length antibody connected to the light chain of the second full length antibody via a peptide linker the amino acid sequence of SEQ ID NO: 32.

In one embodiment the antibody heavy chain variable domain (VH) and the antibody light chain variable domain (VL) of the heavy and light chain of the second full length antibody are disulfide stabilized by introduction of a disulfide bond between the following positions: heavy chain variable domain position 44 to light chain variable domain position 100 (numbering always according to EU index of Kabat; (Kabat, E. A., et al., Sequences of Proteins of Immunological Interest, 5th ed., Public Health Service, National Institutes of Health, Bethesda, Md. (1991))). Such further disulfide stabilization is achieved by the introduction of a disulfide bond between the variable domains VH and VL of the second full length antibody heavy and light chain. Techniques to introduce unnatural disulfide bridges for stabilization are described e.g. in WO 94/029350, Rajagopal, V., et al, Prot. Engin. (1997) 1453-59; Kobayashi, et al., Nuclear Medicine & Biology, Vol. 25 (1998) 387-393; or Schmidt, M., et al., Oncogene 18 (1999) 1711-1721.

Thus in one embodiment such bispecific, bivalent antibody is characterized in comprising a disulfide bond between the variable domains of the second full length antibody heavy and light chain is between heavy chain variable domain position 44 and light chain variable domain position 100, and comprises
- a) as heavy chain of the first full length antibody the amino acid sequence of SEQ ID NO: 36, and as light chain of the first full length antibody the amino acid sequence of SEQ ID NO: 37, and
- b) as heavy chain of the second full length antibody connected to the light chain of the second full length antibody via a peptide linker the amino acid sequence of SEQ ID NO: 35.

In another aspect of the invention the bispecific antibody according to the invention is characterized in comprising
- a) the heavy chain and the light chain of a first full length antibody that specifically binds to VEGF;
- b) the heavy chain and the light chain of a second full length antibody that specifically binds to ANG-2,
  wherein the N-terminus of the heavy chain is connected to the C-terminus of the light chain via a peptide linker; and
  wherein the variable domains VL and VH are replaced by each other.

Figure 2B:
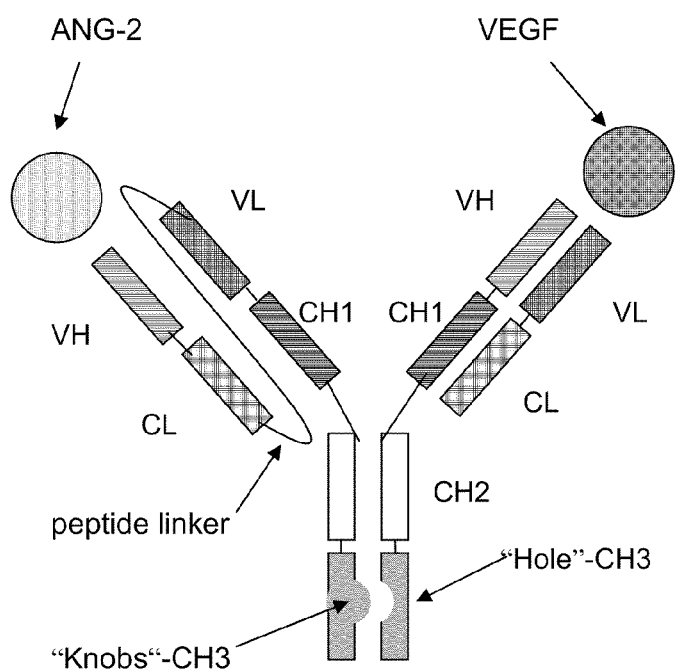

An exemplary scheme of this bispecific, bivalent antibody format for this bispecific antibody specifically binding to human vascular endothelial growth factor (VEGF) and human angiopoietin-2 (ANG-2) is shown in FIG. 2b including Knobs-into. Holes modified CH3 domains. The antibodies based on this bispecific, bivalent antibody format are named in the examples OAscXFab1.

In one embodiment such bispecific antibody is characterized in comprising
- a) as heavy chain of the first full length antibody the SEQ ID NO: 39, and as light chain of the first full length antibody the SEQ ID NO: 40, and
- b) as heavy chain of the second full length antibody connected to the light chain of the second full length antibody via a peptide linker the SEQ ID NO: 38.

In another aspect of the invention the bispecific antibody according to the invention is characterized in comprising
- a) the heavy chain and the light chain of a first full length antibody that specifically binds to VEGF;
- b) the heavy chain and the light chain of a second full length antibody that specifically binds to ANG-2,
  wherein the N-terminus of the heavy chain is connected to the C-terminus of the light chain via a peptide linker; and
  wherein the constant domains CL and CH1 are replaced by each other.

Figure 2C:
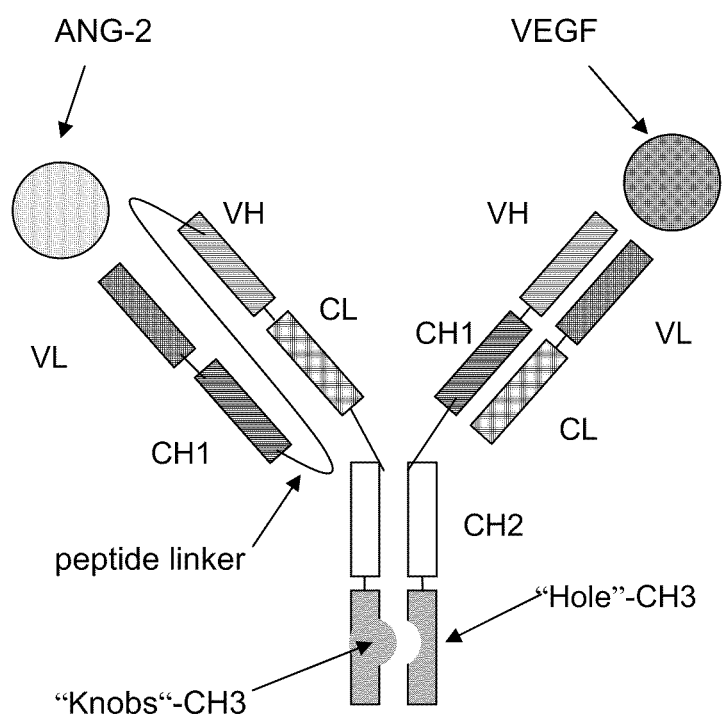

An exemplary scheme of this bispecific, bivalent antibody format for this bispecific antibody specifically binding to human vascular endothelial growth factor (VEGF) and human angiopoietin-2 (ANG-2) is shown in FIG. 2c including Knobs-into-Holes modified CH3 domains. The antibodies based on this bispecific, bivalent antibody format are named in the examples OAscXFab2 and OAscXFab3.

In one embodiment such bispecific antibody is characterized in comprising
- a) as heavy chain of the first full length antibody the SEQ ID NO: 42, and as light chain of the first full length antibody the SEQ ID NO: 43, and
- b) as heavy chain of the second full length antibody connected to the light chain of the second full length antibody via a peptide linker the SEQ ID NO: 41.

In one embodiment such bispecific antibody is characterized in comprising
- a) as heavy chain of the first full length antibody the SEQ ID NO: 45, and as light chain of the first full length antibody the SEQ ID NO: 46, and
- b) as heavy chain of the second full length antibody connected to the light chain of the second full length antibody via a peptide linker the SEQ ID NO: 44.

Accordingly one embodiment of the invention is a bispecific, bivalent antibody comprising a first antigen-binding site that specifically binds to human VEGF and a second antigen-binding site that specifically binds to human ANG-2, characterized in comprising the amino acid sequences of SEQ ID NO: 29, of SEQ ID NO: 30, and of SEQ ID NO: 31.

Accordingly one embodiment of the invention is a bispecific, bivalent antibody comprising a first antigen-binding site that specifically binds to human VEGF and a second antigen-binding site that specifically binds to human ANG-2, characterized in comprising the amino acid sequences of SEQ ID NO: 32, of SEQ ID NO: 33, and of SEQ ID NO: 34.

Accordingly one embodiment of the invention is a bispecific, bivalent antibody comprising a first antigen-binding site that specifically binds to human VEGF and a second antigen-binding site that specifically binds to human ANG-2, characterized in comprising the amino acid sequences of SEQ ID NO: 35, of SEQ ID NO: 36, and of SEQ ID NO: 37.

Accordingly one embodiment of the invention is a bispecific, bivalent antibody comprising a first antigen-binding site that specifically binds to human VEGF and a second antigen-binding site that specifically binds to human ANG-2, characterized in comprising the amino acid sequences of SEQ ID NO: 38, of SEQ ID NO: 39, and of SEQ ID NO: 40.

Accordingly one embodiment of the invention is a bispecific, bivalent antibody comprising a first antigen-binding site that specifically binds to human VEGF and a second antigen-binding site that specifically binds to human ANG-2, characterized in comprising the amino acid sequences of SEQ ID NO: 41, of SEQ ID NO: 42, and of SEQ ID NO: 43.

Accordingly one embodiment of the invention is a bispecific, bivalent antibody comprising a first antigen-binding site that specifically binds to human VEGF and a second antigen-binding site that specifically binds to human ANG-2, characterized in comprising the amino acid sequences of SEQ ID NO: 44, of SEQ ID NO: 45, and of SEQ ID NO: 46.

Preferably the CH3 domains of the bispecific, bivalent antibody according to the invention is altered by the "knob-into-holes" technology which is described in detail with several examples in e.g. WO 96/027011, Ridgway J. B., et al., Protein Eng 9 (1996) 617-621; and Merchant, A. M., et al., Nat Biotechnol 16 (1998) 677-681. In this method the interaction surfaces of the two CH3 domains are altered to increase the heterodimerisation of both heavy chains containing these two CH3 domains. Each of the two CH3 domains (of the two heavy chains) can be the "knob", while the other is the "hole". The introduction of a disulfide bridge stabilizes the heterodimers (Merchant, A. M, et al., Nature Biotech 16 (1998) 677-681; Atwell, S., et al. J. Mol. Biol. 270 (1997) 26-35) and increases the yield.

In a preferred aspect of the invention all bispecific antibodies according to the invention are characterized in that the CH3 domain of one heavy chain and the CH3 domain of the other heavy chain each meet at an interface which comprises an original interface between the antibody CH3 domains;

wherein said interface is altered to promote the formation of the bispecific antibody, wherein the alteration is characterized in that:

a) the CH3 domain of one heavy chain is altered,
so that within the original interface the CH3 domain of one heavy chain that meets the original interface of the CH3 domain of the other heavy chain within the bispecific antibody,
an amino acid residue is replaced with an amino acid residue having a larger side chain volume, thereby generating a protuberance within the interface of the CH3 domain of one heavy chain which is positionable in a cavity within the interface of the CH3 domain of the other heavy chain
and
b) the CH3 domain of the other heavy chain is altered,
so that within the original interface of the second CH3 domain that meets the original interface of the first CH3 domain within the bispecific antibody
an amino acid residue is replaced with an amino acid residue having a smaller side chain volume, thereby generating a cavity within the interface of the second CH3 domain within which a protuberance within the interface of the first CH3 domain is positionable.

Thus the antibody according to invention is preferably characterized in that
   the CH3 domain of the heavy chain of the full length antibody of a) and the CH3 domain of the heavy chain of the full length antibody of b) each meet at an interface which comprises an alteration in the original interface between the antibody CH3 domains;
   wherein i) in the CH3 domain of one heavy chain
   an amino acid residue is replaced with an amino acid residue having a larger side chain volume, thereby generating a protuberance within the interface of the CH3 domain of one heavy chain which is positionable in a cavity within the interface of the CH3 domain of the other heavy chain
   and wherein
   ii) in the CH3 domain of the other heavy chain
   an amino acid residue is replaced with an amino acid residue having a smaller side chain volume, thereby generating a cavity within the interface of the second CH3 domain within which a protuberance within the interface of the first CH3 domain is positionable.

Preferably said amino acid residue having a larger side chain volume is selected from the group consisting of arginine (R), phenylalanine (F), tyrosine (Y), tryptophan (W).

Preferably said amino acid residue having a smaller side chain volume is selected from the group consisting of alanine (A), serine (S), threonine (T), valine (V).

In one aspect of the invention both CH3 domains are further altered by the introduction of cysteine (C) as amino acid in the corresponding positions of each CH3 domain such that a disulfide bridge between both CH3 domains can be formed.

In one embodiment, the bispecific antibody comprises a T366W mutation in the CH3 domain of the "knobs chain" and T366S, L368A, Y407V mutations in the CH3 domain of the "hole chain". An additional interchain disulfide bridge between the CH3 domains can also be used (Merchant, A. M, et al., Nature Biotech 16 (1998) 677-681) e.g. by introducing a Y349C mutation into the CH3 domain of the "knobs chain" and a E356C mutation or a S354C mutation into the CH3 domain of the "hole chain".

In another embodiment, the bispecific antibody according to the invention comprises Y349C, T366W mutations in one of the two CH3 domains and E356C, T366S, L368A, Y407V mutations in the other of the two CH3 domains. In a another preferred embodiment the bispecific antibody comprises Y349C, T366W mutations in one of the two CH3 domains and S354C, T366S, L368A, Y407V mutations in the other of the two CH3 domains (the additional Y349C mutation in one CH3 domain and the additional E356C or S354C mutation in the other CH3 domain forming a interchain disulfide bridge) (numbering always according to EU index of Kabat; (Kabat, E. A., et al., Sequences of Proteins of Immunological Interest, 5th ed., Public Health Service, National Institutes of Health, Bethesda, Md. (1991))). But also other knobs-in-holes technologies as described by EP 1 870 459 A1, can be used alternatively or additionally. Thus another example for the bispecific antibody are R409D; K370E mutations in the CH3 domain of the "knobs chain" and D399K; E357K mutations in the CH3 domain of the "hole chain" (numbering always according to EU index of Kabat; (Kabat, E. A., et al., Sequences of Proteins of Immunological Interest, 5th ed., Public Health Service, National Institutes of Health, Bethesda, Md. (1991))).

In another embodiment the bispecific antibody comprises a T366W mutation in the CH3 domain of the "knobs chain" and T366S, L368A, Y407V mutations in the CH3 domain of the "hole chain" and additionally R409D; K370E mutations in the CH3 domain of the "knobs chain" and D399K; E357K mutations in the CH3 domain of the "hole chain".

In another embodiment the bispecific antibody comprises Y349C, T366W mutations in one of the two CH3 domains and S354C, T366S, L368A, Y407V mutations in the other of the two CH3 domains or said trivalent, bispecific antibody comprises Y349C, T366W mutations in one of the two CH3 domains and S354C, T366S, L368A, Y407V mutations in the other of the two CH3 domains and additionally R409D; K370E mutations in the CH3 domain of the "knobs chain" and D399K; E357K mutations in the CH3 domain of the "hole chain".

In one embodiment of the invention the bispecific antibody according to the invention is characterized in having one or more of the following properties (determined in assays as described in Examples 3 to 7):
   the bispecific, bivalent antibody binds to VEGF with a KD value of the binding affinity of 5 nM or less;
   the bispecific, bivalent antibody binds to ANG-2 with a KD value of the binding affinity of 5 nM or less;
   the bispecific, bivalent antibody inhibits ANG-2-induced Tie2 phosphorylation in HEK293 cells transfected with Tie2 with an IC50 of 15 nM or less, (in one embodiment with an IC50 of 10 nM or less);
   the bispecific, bivalent antibody inhibits ANG-2 binding to Tie2 with an IC50 of 20 nM or less, (in one embodiment with an IC50 of 15 nM or less);
   the bispecific, bivalent antibody inhibits VEGF binding to VEGF receptor with an IC50 of 20 nM or less, (in one embodiment with an IC50 of 15 nM or less);
   the bispecific, bivalent antibody inhibits VEGF-induced proliferation of HUVEC cells with an with an IC50 of 10 nM or less, (in one embodiment with an IC50 of 5 nM or less).

In one embodiment the bispecific, bivalent antibody is characterized in comprising
a first antigen-binding site that specifically binds to human VEGF and a second antigen-binding site that specifically binds to human ANG-2, characterized in that
   i) said first antigen-binding site comprises as heavy chain variable domain (VH) the SEQ ID NO: 1, and as light chain variable domain (VL) the SEQ ID NO: 2; and ii) said second antigen-binding site comprises as heavy chain variable domain (VH) the SEQ ID NO: 3, and as light chain variable domain (VL) the SEQ ID NO: 4;

and having one or more of the following properties (determined in assays as described in Examples 3 to 7):
- the bispecific, bivalent antibody binds to VEGF with a KD value of the binding affinity of 5 nM or less;
- the bispecific, bivalent antibody binds to ANG-2 with a KD value of the binding affinity of 5 nM or less;
- the bispecific, bivalent antibody inhibits ANG-2-induced Tie2 phosphorylation in HEK293 cells transfected with Tie2 with an IC50 of 15 nM or less, (in one embodiment with an IC50 of 10 nM or less);
- the bispecific, bivalent antibody inhibits ANG-2 binding to Tie2 with an IC50 of 20 nM or less, (in one embodiment with an IC50 of 15 nM or less);
- the bispecific, bivalent antibody inhibits VEGF binding to VEGF receptor with an IC50 of 20 nM or less, (in one embodiment with an IC50 of 15 nM or less);
- the bispecific, bivalent antibody inhibits VEGF-induced proliferation of HUVEC cells with an with an IC50 of 10 nM or less, (in one embodiment with an IC50 of 5 nM or less).

In one aspect of the invention such bispecific antibody according to the invention is characterized in comprising
  a) the heavy chain and the light chain of a first full length antibody that specifically binds to VEGF;
  b) the modified heavy chain and modified light chain of a full length antibody that specifically binds to ANG-2, wherein the constant domains CL and CH$_1$ are replaced by each other;

and having one or more of the following properties (determined in assays as described in Examples 3 to 7):
- the bispecific, bivalent antibody binds to VEGF with a KD value of the binding affinity of 5 nM or less;
- the bispecific, bivalent antibody binds to ANG-2 with a KD value of the binding affinity of 5 nM or less;
- the bispecific, bivalent antibody inhibits ANG-2-induced Tie2 phosphorylation in HEK293 cells transfected with Tie2 with an IC50 of 15 nM or less, (in one embodiment with an IC50 of 10 nM or less);
- the bispecific, bivalent antibody inhibits ANG-2 binding to Tie2 with an IC50 of 20 nM or less, (in one embodiment with an IC50 of 15 nM or less);
- the bispecific, bivalent antibody inhibits VEGF binding to VEGF receptor with an IC50 of 20 nM or less, (in one embodiment with an IC50 of 15 nM or less);
- the bispecific, bivalent antibody inhibits VEGF-induced proliferation of HUVEC cells with an with an IC50 of 10 nM or less, (in one embodiment with an IC50 of 5 nM or less).

In one embodiment the bispecific, bivalent antibody is characterized in comprising
a first antigen-binding site that specifically binds to human VEGF and a second antigen-binding site that specifically binds to human ANG-2, characterized in that
  i) said first antigen-binding site comprises as heavy chain variable domain (VH) the SEQ ID NO: 1 with no more than 1 amino acid residue substitutions in the CDRs, and as light chain variable domain (VL) the SEQ ID NO: 2 with no more than 1 amino acid residue substitutions in the CDRs; and
  ii) said second antigen-binding site comprises as heavy chain variable domain (VH) the SEQ ID NO: 3 with no more than 1 amino acid residue substitutions in the CDRs, and as light chain variable domain (VL) the SEQ ID NO: 4 with no more than 1 amino acid residue substitutions in the CDRs.

In one embodiment the bispecific, bivalent antibody is characterized in comprising
a first antigen-binding site that specifically binds to human VEGF and a second antigen-binding site that specifically binds to human ANG-2, characterized in that
  i) said first antigen-binding site comprises as heavy chain variable domain (VH) the SEQ ID NO: 1 with no more than 1 amino acid residue substitutions in the CDRs, and as light chain variable domain (VL) the SEQ ID NO: 2 with no more than 1 amino acid residue substitutions in the CDRs; and
  ii) said second antigen-binding site comprises as heavy chain variable domain (VH) the SEQ ID NO: 3 with no more than 1 amino acid residue substitutions in the CDRs, and as light chain variable domain (VL) the SEQ ID NO: 4 with no more than 1 amino acid residue substitutions in the CDRs;

and having one or more of the following properties (determined in assays as described in Examples 3 to 7):
- the bispecific, bivalent antibody binds to VEGF with a KD value of the binding affinity of 5 nM or less;
- the bispecific, bivalent antibody binds to ANG-2 with a KD value of the binding affinity of 5 nM or less;
- the bispecific, bivalent antibody inhibits ANG-2-induced Tie2 phosphorylation in HEK293 cells transfected with Tie2 with an IC50 of 15 nM or less, (in one embodiment with an IC50 of 10 nM or less);
- the bispecific, bivalent antibody inhibits ANG-2 binding to Tie2 with an IC50 of 20 nM or less, (in one embodiment with an IC50 of 15 nM or less);
- the bispecific, bivalent antibody inhibits VEGF binding to VEGF receptor with an IC50 of 20 nM or less, (in one embodiment with an IC50 of 15 nM or less);
- the bispecific, bivalent antibody inhibits VEGF-induced proliferation of HUVEC cells with an with an IC50 of 10 nM or less, (in one embodiment with an IC50 of 5 nM or less).

In one aspect of the invention the bispecific antibody according to the invention is characterized in comprising
  a) the heavy chain and the light chain of a first full length antibody that specifically binds to VEGF,
    and wherein the heavy chain of the first full length antibody comprises the amino acid sequence of SEQ ID NO:7 with no more than 1 amino acid residue substitutions in the CDRs, and the light chain of the first full length antibody comprises the amino acid sequence of SEQ ID NO: 5 with no more than 1 amino acid residue substitutions in the CDRs, and
  b) the modified heavy chain and modified light chain of a full length antibody that specifically binds to ANG-2, wherein the constant domains CL and CH$_1$ are replaced by each other,
    and wherein the modified heavy chain of the second full length antibody comprises the amino acid sequence of SEQ ID NO: 8 with no more than 1 amino acid residue substitutions in the CDRs, and the modified light chain of the second full length antibody comprises the amino acid sequence of SEQ ID NO: 6 with no more than 1 amino acid residue substitutions in the CDRs.

In one aspect of the invention the bispecific antibody according to the invention is characterized in comprising
  a) the heavy chain and the light chain of a first full length antibody that specifically binds to VEGF, and wherein the heavy chain of the first full length antibody comprises the amino acid sequence of SEQ ID NO:7 with no more than 1 amino acid residue substitutions in the CDRs, and the light chain of the first full length antibody comprises the amino acid sequence of SEQ ID NO: 5 with no more than 1 amino acid residue substitutions in the CDRs, and b) the modified heavy chain and modified light chain of a full length antibody that specifically binds to ANG-2, wherein the constant domains CL and $CH_1$ are replaced by each other, and wherein the modified heavy chain of the second full length antibody comprises the amino acid sequence of SEQ ID NO: 8 with no more than 1 amino acid residue substitutions in the CDRs, and the modified light chain of the second full length antibody comprises the amino acid sequence of SEQ ID NO: 6 with no more than 1 amino acid residue substitutions in the CDRs;

and having one or more of the following properties (determined in assays as described in Examples 3 to 7):

the bispecific, bivalent antibody binds to VEGF with a KD value of the binding affinity of 5 nM or less;

the bispecific, bivalent antibody binds to ANG-2 with a KD value of the binding affinity of 5 nM or less;

the bispecific, bivalent antibody inhibits ANG-2-induced Tie2 phosphorylation in HEK293 cells transfected with Tie2 with an 1050 of 15 nM or less, (in one embodiment with an 1050 of 10 nM or less);

the bispecific, bivalent antibody inhibits ANG-2 binding to Tie2 with an 1050 of 20 nM or less, (in one embodiment with an 1050 of 15 nM or less);

the bispecific, bivalent antibody inhibits VEGF binding to VEGF receptor with an 1050 of 20 nM or less, (in one embodiment with an 1050 of 15 nM or less);

the bispecific, bivalent antibody inhibits VEGF-induced proliferation of HUVEC cells with an with an 1050 of 10 nM or less, (in one embodiment with an 1050 of 5 nM or less).

As used herein, "antibody" refers to a binding protein that comprises antigen-binding sites. The terms "binding site" or "antigen-binding site" as used herein denotes the region(s) of an antibody molecule to which a ligand actually binds. The term "antigen-binding site" comprises an antibody heavy chain variable domains (VH) and an antibody light chain variable domains (VL) (pair of VH/VL).).

Antibody specificity refers to selective recognition of the antibody for a particular epitope of an antigen. Natural antibodies, for example, are monospecific.

"Bispecific antibodies" according to the invention are antibodies which have two different antigen-binding specificities. Antibodies of the present invention are specific for two different antigens, VEGF as first antigen and ANG-2 as second antigen.

The term "monospecific" antibody as used herein denotes an antibody that has one or more binding sites each of which bind to the same epitope of the same antigen.

The term "valent" as used within the current application denotes the presence of a specified number of binding sites in an antibody molecule. As such, the terms "bivalent", "tetravalent", and "hexavalent" denote the presence of two binding site, four binding sites, and six binding sites, respectively, in an antibody molecule. The bispecific antibodies according to the invention are "bivalent".

The term "VEGF" as used herein refers to human vascular endothelial growth factor (VEGF/VEGF-A) (SEQ ID NO: 47) which is described e.g. in Leung, D. W., et al., Science 246 (1989) 1306-9; Keck, P. J., et al., Science 246 (1989) 1309-12 and Connolly, D. T., et al., J. Biol. Chem. 264 (1989) 20017-24. VEGF is involved in the regulation of normal and abnormal angiogenesis and neovascularization associated with tumors and intraocular disorders (Ferrara, N., et al., Endocr. Rev. 18 (1997) 4-25; Berkman, R. A., et al., J. Clin. Invest. 91 (1993) 153-159; Brown, L. F., et al., Human Pathol. 26 (1995) 86-91; Brown, L. F., et al., Cancer Res. 53 (1993) 4727-4735; Mattern, J., et al., Brit. J. Cancer. 73 (1996) 931-934; and Dvorak, H. F., et al., Am. J. Pathol. 146 (1995) 1029-1039). VEGF is a homodimeric glycoprotein that has been isolated from several sources. VEGF shows highly specific mitogenic activity for endothelial cells.

The term "ANG-2" as used herein refers to human angiopoietin-2 (ANG-2) (alternatively abbreviated with ANGPT2 or ANG2) (SEQ ID NO: 48) which is described e.g. in Maisonpierre, P. C., et al, Science 277 (1997) 55-60 and Cheung, A. H., et al., Genomics 48 (1998) 389-91. The angiopoietins-1 and -2 were discovered as ligands for the Ties, a family of tyrosine kinases that is selectively expressed within the vascular endothelium. Yancopoulos, G. D., et al., Nature 407 (2000) 242-48. There are now four definitive members of the angiopoietin family. Angiopoietin-3 and -4 (Ang-3 and Ang-4) may represent widely diverged counterparts of the same gene locus in mouse and man. Kim, I., et al., FEBS Let, 443 (1999) 353-56; Kim, I., et al., J Biol Chem 274 (1999) 26523-28. ANG-1 and ANG-2 were originally identified in tissue culture experiments as agonist and antagonist, respectively (see for ANG-1: Davis, S., et al., Cell 87 (1996) 1161-69; and for ANG-2: Maisonpierre, P. C., et al., Science 277 (1997) 55-60) All of the known angiopoietins bind primarily to Tie2, and both Ang-1 and -2 bind to Tie2 with an affinity of 3 nM (Kd). Maisonpierre, P. C., et al., Science 277 (1997) 55-60.

An antigen-binding sites of the bispecific antibody of the invention contain six complementarity determining regions (CDRs) which contribute in varying degrees to the affinity of the binding site for antigen. There are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences. Also included within the scope of the invention are functional antigen binding sites comprised of fewer CDRs (i.e., where binding specificity is determined by three, four or five CDRs). For example, less than a complete set of 6 CDRs may be sufficient for binding. In some cases, a VH or a VL domain will be sufficient.

The antibodies of the invention further comprise immunoglobulin constant regions of one or more immunoglobulin classes. Immunoglobulin classes include IgG, IgM, IgA, IgD, and IgE isotypes and, in the case of IgG and IgA, their subtypes.

The terms "monoclonal antibody" or "monoclonal antibody composition" as used herein refer to a preparation of antibody molecules of a single amino acid composition.

The term "chimeric antibody" refers to an antibody comprising a variable region, i.e., binding region, from one source or species and at least a portion of a constant region derived from a different source or species, usually prepared by recombinant DNA techniques. Chimeric antibodies comprising a murine variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies.". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See, e.g., Morrison, S. L., et al., Proc. Natl. Acad. Sci. USA 81 (1984) 6851-6855; U.S. Pat. No. 5,202,238 and U.S. Pat. No. 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See, e.g., Riechmann, L., et al., Nature 332 (1988) 323-327; and Neuberger, M. S., et al., Nature 314 (1985) 268-270. Particularly preferred CDRs correspond to those representing sequences recognizing the antigens noted above for chimeric antibodies. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Brueggemann, M., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole, A., et al. and Boerner, P., et al. are also available for the preparation of human monoclonal antibodies (Cole, A., et al., Monoclonal Antibodies and Cancer Therapy, Liss, A. L., p. 77 (1985); and Boerner, P., et al., J. Immunol. 147 (1991) 86-95). As already mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation).

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The "variable domain" (variable domain of a light chain (VL), variable domain of a heavy chain (VH) as used herein denotes each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions play a particularly important role in the binding specificity/affinity of the antibodies according to the invention and therefore provide a further object of the invention.

The terms "hypervariable region" or "antigen-binding portion of an antibody" when used herein refer to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. CDRs on each chain are separated by such framework amino acids. Especially, CDR3 of the heavy chain is the region which contributes most to antigen binding. CDR and FR regions are determined according to the standard definition of Kabat, E. A., et al., Sequences of Proteins of Immunological Interest, 5th ed., Public Health Service, National Institutes of Health, Bethesda, Md. (1991) (includes the numbering according to the EU Index of Kabat, (abbreviated as numbering according to Kabat herein below)).

As used herein, the term "binding" or "specifically binding" refers to the binding of the antibody to an epitope of the antigen (either human VEGF or human ANG-2) in an in vitro assay, preferably in an plasmon resonance assay (BIAcore, GE-Healthcare Uppsala, Sweden) (Example 3) with purified wild-type antigen. The affinity of the binding is defined by the terms ka (rate constant for the association of the antibody from the antibody/antigen complex), $k_D$ (dissociation constant), and $K_D$ ($k_D$/ka). In one embodiment binding or specifically binding means a binding affinity ($K_D$) of $10^{-8}$ mol/l or less, preferably $10^{-9}$ M to $10^{-13}$ mol/l.

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

In certain embodiments, an antibody is said to specifically bind an antigen when it preferentially recognizes its target antigen in a complex mixture of proteins and/or macromolecules.

The term "full length antibody" denotes an antibody consisting of two "full length antibody heavy chains" and two "full length antibody light chains" (see FIG. 1). A "full length antibody heavy chain" is a polypeptide consisting in N-terminal to C-terminal direction of an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3), abbreviated as VH-CH1-HR—CH2-CH$_3$; and optionally an antibody heavy chain constant domain 4 (CH4) in case of an antibody of the subclass IgE. Preferably the "full length antibody heavy chain" is a polypeptide consisting in N-terminal to C-terminal direction of VH, CH1, HR, CH2 and CH3. A "full length antibody light chain" is a polypeptide consisting in N-terminal to C-terminal direction of an antibody light chain variable domain (VL), and an antibody light chain constant domain (CL), abbreviated as VL-CL. The antibody light chain constant domain (CL) can be δ (kappa) or λ (lambda). The two full length antibody chains are linked together via inter-polypeptide disulfide bonds between the CL domain and the CH1 domain and between the hinge regions of the full length antibody heavy chains. Examples of typical full length antibodies are natural antibodies like IgG (e.g. IgG 1 and IgG2), IgM, IgA, IgD, and IgE. The full length antibodies according to the invention can be from a single species e.g. human, or they can be chimerized or humanized antibodies. The full length antibodies according to the invention comprise two antigen binding sites each formed by a pair of VH and VL, which both specifically bind to the same antigen. The C-terminus of the heavy or light chain of said full length antibody denotes the last amino acid at the C-terminus of said heavy or light chain. The N-terminus of the heavy or light chain of said full length antibody denotes the last amino acid at the N-terminus of said heavy or light chain.

The term "peptide linker" as used within the invention denotes a peptide with amino acid sequences, which is preferably of synthetic origin. These peptides according to invention are used to connect the C-terminus of the light chain to the N-terminus of heavy chain of the second full length antibody (that specifically binds to a second antigen) via a peptide linker. The peptide linker within the second full length antibody heavy and light chain is a peptide with an amino acid sequence with a length of at least 30 amino acids, preferably with a length of 32 to 50 amino acids. In one the peptide linker is a peptide with an amino acid sequence with a length of 32 to 40 amino acids. In one embodiment said linker is (G×S)n with G=glycine, S=serine, (x=3, n=8, 9 or 10 and m=0, 1, 2 or 3) or (x=4 and n=6, 7 or 8 and m=0, 1, 2 or 3), preferably with x=4, n=6 or 7 and m=0, 1, 2 or 3, more preferably with x=4, n=7 and m=2. In one embodiment said linker is (G$_4$S)$_6$G$_2$.

The term "constant region" as used within the current applications denotes the sum of the domains of an antibody other than the variable region. The constant region is not involved directly in binding of an antigen, but exhibits various effector functions. Depending on the amino acid sequence of the constant region of their heavy chains, antibodies are divided in the classes: IgA, IgD, IgE, IgG and IgM, and several of these may be further divided into subclasses, such as IgG1, IgG2, IgG3, and IgG4, IgA1 and IgA2. The heavy chain constant regions that correspond to the different classes of antibodies are called α, δ, ε, γ, and μ, respectively. The light chain constant regions which can be found in all five antibody classes are called κ (kappa) and λ (lambda).

The term "constant region derived from human origin" as used in the current application denotes a constant heavy chain region of a human antibody of the subclass IgG1, IgG2, IgG3, or IgG4 and/or a constant light chain kappa or lambda region. Such constant regions are well known in the state of the art and e.g. described by Kabat, E. A., (see e.g. Johnson, G., and Wu, T. T., Nucleic Acids Res. 28 (2000) 214-218; Kabat, E. A., et al., Proc. Natl. Acad. Sci. USA 72 (1975) 2785-2788).

Preferably the bispecific, bivalent antibodies according to the invention have a constant region of human IgG1 subclass.

While antibodies of the IgG4 subclass show reduced Fc receptor (FcγRIIIa) binding, antibodies of other IgG subclasses show binding. However Pro238, Asp265, Asp270, Asn297 (loss of Fc carbohydrate), Pro329, Leu234, Leu235, Gly236, Gly237, Ile253, Ser254, Lys288, Thr307, Gln311, Asn434, and His435 are residues which, if altered, provide also reduced Fc receptor binding (Shields, R. L., et al., J. Biol. Chem. 276 (2001) 6591-6604; Lund, J., et al., FASEB J. 9 (1995) 115-119; Morgan, A., et al., Immunology 86 (1995) 319-324; EP 0 307 434).

In one embodiment an antibody according to the invention has a reduced FcR binding compared to an IgG1 antibody and the bispecific, bivalent antibody is in regard to FcR binding of IgG4 subclass or of IgG1 subclass with a mutation in S228, L234, L235 and/or D265, and/or contains the PVA236 mutation. In one embodiment the mutations in the bispecific bivalent antibody are in IgG4 S228P and L235E and in IgG1 L234A and L235A.

Another aspect of the invention a bispecific, bivalent antibody characterized in comprising
a) the heavy chain and the light chain of a first full length antibody that specifically binds to a first antigen;
b) the heavy chain and the light chain of a second full length antibody that specifically binds to a second antigen,
wherein the N-terminus of the heavy chain is connected to the C-terminus of the light chain via a peptide linker; and
wherein the variable domains VL and VH or the constant domains CL and CH1 are replaced by each other.

Preferably the CH3 domains of this bispecific, bivalent antibody format is altered by the "knob-into-holes" technology which is described in detail with several examples in e.g. WO 96/027011, Ridgway J. B., et al., Protein Eng 9 (1996) 617-621; and Merchant, A. M., et al., Nat Biotechnol 16 (1998) 677-681. In this method the interaction surfaces of the two CH3 domains are altered to increase the heterodimerisation of both heavy chains containing these two CH3 domains. Each of the two CH3 domains (of the two heavy chains) can be the "knob", while the other is the "hole". The introduction of a disulfide bridge stabilizes the heterodimers (Merchant, A. M, et al., Nature Biotech 16 (1998) 677-681; Atwell, S., et al. J. Mol. Biol. 270 (1997) 26-35) and increases the yield. For further details and embodiments see above.

Another aspect of the invention a bispecific, bivalent antibody characterized in comprising
a) the heavy chain and the light chain of a first full length antibody that specifically binds to a first antigen;
b) the heavy chain and the light chain of a second full length antibody that specifically binds to a second antigen,
wherein the N-terminus of the heavy chain is connected to the C-terminus of the light chain via a peptide linker; and
wherein the variable domains VL and VH are replaced by each other.

An exemplary scheme of this bispecific, bivalent antibody format is shown in FIG. 2b including Knobs-into-Holes modified CH3 domains. The antibodies based on this bispecific, bivalent antibody format are named in the examples OAscXFab1.

In one embodiment such bispecific antibody is characterized in comprising
  a) as heavy chain of the first full length antibody the SEQ ID NO: 39, and as light chain of the first full length antibody the SEQ ID NO: 40, and
  b) as heavy chain of the second full length antibody connected to the light chain of the second full length antibody via a peptide linker the SEQ ID NO: 38.

Another aspect of the invention a bispecific, bivalent antibody characterized in comprising
  a) the heavy chain and the light chain of a first full length antibody that specifically binds to a first antigen;
  b) the heavy chain and the light chain of a second full length antibody that specifically binds to a second antigen,
    wherein the N-terminus of the heavy chain is connected to the C-terminus of the light chain via a peptide linker; and
    wherein the constant domains CL and CH1 are replaced by each other.

An exemplary scheme of this bispecific, bivalent antibody format is shown in FIG. 2c including Knobs-into-Holes modified CH3 domains. The antibodies based on this bispecific, bivalent antibody format are named in the examples OAscXFab2 and OAscXFab3.

In one embodiment such bispecific antibody is characterized in comprising
  a) as heavy chain of the first full length antibody the SEQ ID NO: 42, and as light chain of the first full length antibody the SEQ ID NO: 43, and
  b) as heavy chain of the second full length antibody connected to the light chain of the second full length antibody via a peptide linker the SEQ ID NO: 41.

In one embodiment such bispecific antibody is characterized in comprising
  a) as heavy chain of the first full length antibody the SEQ ID NO: 45, and as light chain of the first full length antibody the SEQ ID NO: 46, and
  b) as heavy chain of the second full length antibody connected to the light chain of the second full length antibody via a peptide linker the SEQ ID NO: 44.

The antibody according to the invention is produced by recombinant means. Thus, one aspect of the current invention is a nucleic acid encoding the antibody according to the invention and a further aspect is a cell comprising said nucleic acid encoding an antibody according to the invention. Methods for recombinant production are widely known in the state of the art and comprise protein expression in prokaryotic and eukaryotic cells with subsequent isolation of the antibody and usually purification to a pharmaceutically acceptable purity. For the expression of the antibodies as aforementioned in a host cell, nucleic acids encoding the respective modified light and heavy chains are inserted into expression vectors by standard methods. Expression is performed in appropriate prokaryotic or eukaryotic host cells like CHO cells, NS0 cells, SP2/0 cells, HEK293 cells, COS cells, PER.C6 cells, yeast, or E. coli cells, and the antibody is recovered from the cells (supernatant or cells after lysis). General methods for recombinant production of antibodies are well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-160; Werner, R. G., Drug Res. 48 (1998) 870-880.

Accordingly one embodiment of the invention is a method for the preparation of a bispecific antibody according to the invention, comprising the steps of a) transforming a host cell with vectors comprising nucleic acid molecules encoding said antibody;
  b) culturing the host cell under conditions that allow synthesis of said antibody molecule; and
  c) recovering said antibody molecule from said culture.

The bispecific antibodies are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

Amino acid sequence variants (or mutants) of the bispecific antibody are prepared by introducing appropriate nucleotide changes into the antibody DNA, or by nucleotide synthesis. Such modifications can be performed, however, only in a very limited range. For example, the modifications do not alter the above mentioned antibody characteristics such as the IgG isotype and antigen binding, but may improve the yield of the recombinant production, protein stability or facilitate the purification.

The term "host cell" as used in the current application denotes any kind of cellular system which can be engineered to generate the antibodies according to the current invention. In one embodiment HEK293 cells and CHO cells are used as host cells. As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

Expression in NS0 cells is described by, e.g., Barnes, L. M., et al., Cytotechnology 32 (2000) 109-123; Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A preferred transient expression system (HEK 293) is described by Schlaeger, E.-J., and Christensen, K., in Cytotechnology 30 (1999) 71-83 and by Schlaeger, E.-J., in J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

Purification of antibodies is performed in order to eliminate cellular components or other contaminants, e.g. other cellular nucleic acids or proteins, by standard techniques, including alkaline/SDS treatment, CsCl banding, column chromatography, agarose gel electrophoresis, and others well known in the art. See Ausubel, F., et al., ed. Current Protocols in Molecular Biology, Greene Publishing and Wiley Interscience, New York (1987). Different methods are well established and widespread used for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102).

It has now been found that the bispecific antibodies against human VEGF and human ANG-2 according to the current invention have valuable characteristics such as high stability and valuable pharmacokinetic/pharmacodynamic properties like e.g. good (i.e. slow) clearance (e.g. at low doses).

The bispecific, bivalent antibodies according to the invention show benefits for human patients in need of a VEGF and ANG-2 targeting therapy.

Furthermore they have biological or pharmacological activity and show in vivo tumor growth inhibition and/or inhibition of tumor angiogenesis.

The bispecific antibodies according to the invention are highly effective in
  a) tumor growth inhibition (e.g. with the bispecific antibodies according to the invention tumor stasis could be achieved already at lower concentrations compared to the combination of the two monospecific antibodies (e.g in the COLO205 and the KPL4 tumor models of Example 9 and 10, tumor stasis was already achieved with 10 mg/kg XMAb1 compared to the combination of 10 mg/kg of ANG2i-LC06+10 mg/kg of Avastin), and/or
  b) inhibition of tumor angiogenesis or vascular diseases (e.g. maximal antiangiogenic effects with the bispecific antibodies according to the invention could already be achieved at lower concentrations compared to the combination of the two monospecific antibodies (e.g. in the mouse corneal angiogenesis assay of Example 8, the maximal antiangiogenic effect was already achieved with 10 mg/kg XMAb1 compared to the combination of 10 mg/kg of ANG2i-LC06+10 mg/kg of Avastin).

Finally the bivalent bispecific against human VEGF and human ANG-2 according to the current invention may have a valuable efficacy/toxicity profile and may provide benefits for a patient in the need of an anti-VEGF and anti-ANG-2 therapy.

One aspect of the invention is a pharmaceutical composition comprising an antibody according to the invention. Another aspect of the invention is the use of an antibody according to the invention for the manufacture of a pharmaceutical composition. A further aspect of the invention is a method for the manufacture of a pharmaceutical composition comprising an antibody according to the invention. In another aspect, the present invention provides a composition, e.g. a pharmaceutical composition, containing an antibody according to the present invention, formulated together with a pharmaceutical carrier.

One embodiment of the invention is the bispecific antibody according to the invention for the treatment of cancer.

Another aspect of the invention is said pharmaceutical composition for the treatment of cancer.

Another aspect of the invention is the use of an antibody according to the invention for the manufacture of a medicament for the treatment of cancer.

Another aspect of the invention is method of treatment of patient suffering from cancer by administering an antibody according to the invention to a patient in the need of such treatment.

Another aspect of the invention is said pharmaceutical composition for the prevention of metastasis.

The invention comprises the bispecific antibody according to the invention for the prevention of metastasis.

Another aspect of the invention is the use of a bispecific antibody according to the invention for the manufacture of a medicament for the prevention of metastasis.

Another aspect of the invention is a method of prevention metastasis in patient suffering from primary cancer by administering a bispecific according to the invention to a patient in the need of such preventative treatment.

We could show highly efficient prevention of spontaneous metastasis/secondary tumors in vivo in a orthotopic and a subcutaneous cancer model (see Example 9) in contrast to experimental model where the tumor cells are injected i.v. This is similar to the clinical situation wherein cells disseminate from a primary tumor and metastase to secondary organ like lung or liver (where secondary tumors).

The term "metastasis" according to the invention refers to the transmission of cancerous cells from the primary tumor to one or more sites elsewhere in a patient where then secondary tumors develop. Means to determine if a cancer has metastasized are known in the art and include bone scan, chest X-ray, CAT scan, MRI scan, and tumor marker tests.

The term "prevention of metastasis" or "prevention of secondary tumors" as used herein have the same meaning and refers a prophylactic agent against metastasis in patient suffering from cancer in this way inhibiting or reducing a further transmission of cancerous cells from the primary tumor to one or more sites elsewhere in a patient. This means that the metastasis of the primary, tumor or cancer is prevented, delayed, or reduced and thus the development of secondary tumors is prevented, delayed, or reduced. Preferably the metastasis i.e. secondary tumors of the lung are prevented or reduced, which means that metastatic transmission of cancerous cells from the primary tumor to the lung is prevented or reduced.

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A composition of the present invention can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion.

The term cancer as used herein refers to proliferative diseases, such as lymphomas, lymphocytic leukemias, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, including refractory versions of any of the above cancers, or a combination of one or more of the above cancers.

Another aspect of the invention is the bispecific antibody according to the invention or said pharmaceutical composition as anti-angiogenic agent. Such anti-angiogenic agent can be used for the treatment of cancer, especially solid tumors, and other vascular diseases.

One embodiment of the invention is the bispecific antibody according to the invention for the treatment of vascular diseases.

Another aspect of the invention is said pharmaceutical composition for the treatment of vascular diseases.

Another aspect of the invention is the use of an antibody according to the invention for the manufacture of a medicament for the treatment of vascular diseases.

Another aspect of the invention is method of treatment of patient suffering from vascular diseases by administering an antibody according to the invention to a patient in the need of such treatment.

The term "vascular diseases" includes Cancer, Inflammatory diseases, Atherosclerosis, Ischemia, Trauma, Sepsis, COPD, Asthma, Diabetes, AMD, Retinopathy, Stroke, Adipositas, Acute lung injury, Hemorrhage, Vascular leak e.g. Cytokine induced, Allergy, Graves' Disease, Hashimoto's Autoimmune Thyroiditis, Idiopathic Thrombocytopenic Purpura, Giant Cell Arteritis, Rheumatoid Arthritis, Systemic Lupus Erythematosus (SLE), Lupus Nephritis, Crohn's Disease, Multiple Sclerosis, Ulcerative Colitis, especially to solid tumors, intraocular neovascular syndromes such as proliferative retinopathies or age-related macular degeneration (AMD), rheumatoid arthritis, and psoriasis (Folkman, J., et al., J. Biol. Chem. 267 (1992) 10931-10934; Klagsbrun, M., et al., Annu Rev. Physiol. 53 (1991) 217-239; and Garner, A., Vascular diseases, In: Pathobiology of ocular disease, A dynamic approach, Garner, A., and Klintworth, G. K., (eds.), 2nd edition, Marcel Dekker, New York (1994), pp 1625-1710).

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers.

It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

The term "transformation" as used herein refers to process of transfer of a vectors/nucleic acid into a host cell. If cells without formidable cell wall barriers are used as host cells, transfection is carried out e.g. by the calcium phosphate precipitation method as described by Graham, F. L., van der Eb, A. J., Virology 52 (1973) 546-467. However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride as described by Cohen, S, N., et al., PNAS. 69 (1972) 2110-2114.

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

The following examples, sequence listing and figures are provided to aid the understanding of the present invention, the true scope of which is set forth in the appended claims. It is understood that modifications can be made in the procedures set forth without departing from the spirit of the invention.

Description of the Sequence Listing (Amino Acid Sequences)
SEQ ID NO:1 variable heavy chain domain VH of <VEGF> bevacizumab
SEQ ID NO:2 variable light chain domain VL of <VEGF> bevacizumab
SEQ ID NO:3 variable heavy chain domain VH of <ANG-2> E6Q
SEQ ID NO:4 variable light chain domain VL of <ANG-2> E6Q
SEQ ID NO: 5 XMab1—<VEGF> light chain
SEQ ID NO: 6 XMab1—<ANG2> light chain
SEQ ID NO: 7 XMab1—<VEGF> heavy chain
SEQ ID NO: 8 XMab1—<ANG2> heavy chain
SEQ ID NO: 9 XMab2—<VEGF> light chain
SEQ ID NO: 10 XMab2—<ANG2> light chain
SEQ ID NO: 11 XMab2—<VEGF> heavy chain
SEQ ID NO: 12 XMab2—<ANG2> heavy chain
SEQ ID NO: 13 XMab3—<VEGF> light chain
SEQ ID NO: 14 XMab3—<ANG2> light chain
SEQ ID NO: 15 XMab3—<VEGF> heavy chain
SEQ ID NO: 16 XMab3—<ANG2> heavy chain
SEQ ID NO: 17 XMab4—<VEGF> light chain
SEQ ID NO: 18 XMab4—<ANG2> light chain
SEQ ID NO: 19 XMab4—<VEGF> heavy chain
SEQ ID NO: 20 XMab4—<ANG2> heavy chain
SEQ ID NO: 21 XMab5—<VEGF> light chain
SEQ ID NO: 22 XMab5—<ANG2> light chain
SEQ ID NO: 23 XMab5—<VEGF> heavy chain
SEQ ID NO: 24 XMab5—<ANG2> heavy chain
SEQ ID NO: 25 XMab6—<VEGF> light chain
SEQ ID NO: 26 XMab6—<ANG2> light chain
SEQ ID NO: 27 XMab6—<VEGF> heavy chain
SEQ ID NO: 28 XMab6—<ANG2> heavy chain
SEQ ID NO: 29 OAscFab1—<ANG2> peptide connected heavy chain and light chain
SEQ ID NO: 30 OAscFab1—<VEGF> heavy chain
SEQ ID NO: 31 OAscFab1—<VEGF> light chain
SEQ ID NO: 32 OAscFab2—<ANG2> peptide connected heavy chain and light chain
SEQ ID NO: 33 OAscFab2—<VEGF> heavy chain
SEQ ID NO: 34 OAscFab2—<VEGF> light chain
SEQ ID NO: 35 OAscFab3—<ANG2> peptide connected heavy chain and light chain
SEQ ID NO: 36 OAscFab3—<VEGF> heavy chain
SEQ ID NO: 37 OAscFab3—<VEGF> light chain
SEQ ID NO:38 OAscXFab1—<ANG2> peptide connected heavy chain and light chain
SEQ ID NO: 39 OAscXFab1—<VEGF> heavy chain
SEQ ID NO: 40 OAscXFab1—<VEGF> light chain
SEQ ID NO: 41 OAscXFab2—<ANG2> peptide connected heavy chain and light chain
SEQ ID NO: 42 OAscXFab2—<VEGF> heavy chain
SEQ ID NO: 43 OAscXFab2—<VEGF> light chain
SEQ ID NO: 44 OAscXFab3—<ANG2> peptide connected heavy chain and light chain
SEQ ID NO: 45 OAscXFab3—<VEGF> heavy chain
SEQ ID NO: 46 OAscXFab3—<VEGF> light chain
SEQ ID NO: 47 Human vascular endothelial growth factor (VEGF)
SEQ ID NO: 48 Human angiopoietin-2 (ANG-2)

Experimental Procedures

EXAMPLES

Materials & General Methods

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, Md. (1991). Amino acids of antibody chains are numbered and referred to according to EU numbering (Edelman, G. M., et al., Proc. Natl. Acad. Sci. USA 63 (1969) 78-85; Kabat, E. A., et al., Sequences of Proteins of Immunological Interest, 5th ed., Public Health Service, National Institutes of Health, Bethesda, Md., (1991)).

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

Gene Synthesis

Desired gene segments can be prepared from oligonucleotides made by chemical synthesis. The gene segments, which are flanked by singular restriction endonuclease cleavage sites, were assembled by annealing and ligation of oligonucleotides including PCR amplification and subsequently cloned via the indicated restriction sites e.g. KpnI/SacI or AscI/PacI into a pPCRScript (Stratagene) based pGA4 cloning vector. The DNA sequences of the subcloned gene fragments were confirmed by DNA sequencing.

Gene synthesis fragments were ordered according to given specifications at Geneart (Regensburg, Germany). All gene segments encoding light and heavy 30 chains of Ang-2/VEGF bispecific antibodies were synthesized with a 5'-end DNA sequence coding for a leader peptide (MGWSCIILFLVATAT-GVHS) (SEQ ID NO:49), which targets proteins for secretion in eukaryotic cells, and unique restriction sites at the 5' and 3' ends of the synthesized gene. DNA sequences carrying disulfide stabilized "knobs-into-hole" modified heavy chains were designed with S354C and T366W mutations in the "knobs" heavy chain and Y349C, T366S, L368A and Y407V mutations in the "hole" heavy chain.

DNA Sequence Determination

DNA sequences were determined by double strand sequencing performed at MediGenomix GmbH (Martinsried, Germany) or Sequiserve GmbH (Vaterstetten, Germany).

DNA and Protein Sequence Analysis and Sequence Data Management

The GCG's (Genetics Computer Group, Madison, Wis.) software package version 10.2 and Infomax's Vector NT1 Advance suite version 8.0 was used for sequence creation, mapping, analysis, annotation and illustration.

Expression Vectors

For the expression of the described antibodies variants of expression plasmids for transient expression (e.g. in HEK293 EBNA or HEK293-F) cells or for stable expression (e.g. in CHO cells) based either on a cDNA organization with a CMV-Intron A promoter or on a genomic organization with a CMV promoter (e.g. FIG. 2B) were applied.

Beside the antibody expression cassette the vectors contained:
  an origin of replication which allows replication of this plasmid in *E. coli*, and
  a β-lactamase gene which confers ampicillin resistance in *E. coli*.

The transcription unit of the antibody gene is composed of the following elements:
  unique restriction site(s) at the 5' end
  the immediate early enhancer and promoter from the human cytomegalovirus,
  followed by the Intron A sequence in the case of the cDNA organization,
  a 5'-untranslated region of a human antibody gene,
  a immunoglobulin heavy chain signal sequence,
  the human antibody chain (heavy chain, modified heavy chain or light chain) either as cDNA or as genomic organization with an the immunoglobulin exon-intron organization
  a 3' untranslated region with a polyadenylation signal sequence, and
  unique restriction site(s) at the 3' end.

For transient and stable transfections larger quantities of the plasmids were prepared by plasmid preparation from transformed *E. coli* cultures (Nucleobond AX, Macherey-Nagel).

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

Transient Transfections in HEK293-F System

Recombinant immunoglobulin variants were expressed by transient transfection of human embryonic kidney 293-F cells using the FreeStyle™ 293 Expression System according to the manufacturer's instruction (Invitrogen, USA). Briefly, suspension FreeStyle™ 293-F cells were cultivated in FreeStyle™ 293 Expression medium at 37° C./8% $CO_2$ and the cells were seeded in fresh medium at a density of $1-2\times10^6$ viable cells/ml on the day of transfection. DNA-293Fectin™ complexes were prepared in Opti-MEM® I medium (Invitrogen, USA) using 325 µl of 293Fectin™ (Invitrogen, Germany) and 250 µg of heavy and light chain plasmid DNA in a 1:1 molar ratio for a 250 ml final transfection volume for monospecific parent antibodies. "Knobs-into-hole" DNA-293fectin complexes with two heavy chains and one light chain were prepared in Opti-MEM® I medium (Invitrogen, USA) using 325 µl of 293Fectin™ (Invitrogen, Germany) and 250 µg of "Knobs-into-hole" heavy chain 1 and 2 and light chain plasmid DNA generally in a 1:1:1 molar ratio for a 250 ml final transfection volume (OAscFab and OAscXFab). For expression yield optimization the ratio can be varied. XMab DNA-293fectin complexes were prepared in Opti-MEM® I medium (Invitrogen, USA) using 325 µl of 293Fectin™ (Invitrogen, Germany) and 250 µg of "Knobs-into-hole" heavy chain 1 and 2 and light chain plasmid DNA in a 1:1:1:1 molar ratio for a 250 ml final transfection volume. For expression yield optimization the ratio can be varied. Antibody containing cell culture supernatants were harvested 7 days after transfection by centrifugation at 14000 g for 30 minutes and filtered through a sterile filter (0.22 µm). Supernatants were stored at −20° C. until purification.

Protein Determination

The protein concentration of purified antibodies and derivatives was determined by determining the optical density (OD) at 280 nm, using the molar extinction coefficient calculated on the basis of the amino acid sequence according to Pace, C. N., et. al., Protein Science 4 (1995) 2411-1423.

Antibody Concentration Determination in Supernatants

The concentration of antibodies and derivatives in cell culture supernatants was estimated by immunoprecipitation with Protein A Agarose-beads (Roche). 60 µL Protein A Agarose beads are washed three times in TBS-NP40 (50 mM Tris, pH 7.5, 150 mM NaCl, 1% Nonidet-P40). Subsequently, 1-15 mL cell culture supernatant are applied to the Protein A Agarose beads pre-equilibrated in TBS-NP40. After incubation for at 1 h at room temperature the beads are washed on an Ultrafree-MC-filter column (Amicon] once with 0.5 mL TBS-NP40, twice with 0.5 mL 2× phosphate buffered saline (2×PBS, Roche) and briefly four times with 0.5 mL 100 mM Na-citrate pH 5.0. Bound antibody is eluted by addition of 35 µl NuPAGE® LDS Sample Buffer (Invitrogen). Half of the sample is combined with NuPAGE® Sample Reducing Agent or left unreduced, respectively, and heated for 10 min at 70° C. Consequently, 20 µl are applied to an 4-12% NuPAGE® Bis-Tris SDS-PAGE (Invitrogen) (with MOPS buffer for non-reduced SDS-PAGE and MES buffer with NuPAGE® Antioxidant running buffer additive (Invitrogen) for reduced SDS-PAGE) and stained with Coomassie Blue.

The concentration of antibodies and derivatives in cell culture supernatants was measured by Protein A-HPLC chromatography. Briefly, cell culture supernatants containing antibodies and derivatives that bind to Protein A were applied to a HiTrap Protein A column (GE Healthcare) in 50 mM K2HPO4, 300 mM NaCl, pH 7.3 and eluted from the matrix with 550 mM acetic acid, pH 2.5 on a Dionex HPLC-System.

The eluted protein was quantified by UV absorbance and integration of peak areas. A purified standard IgG1 antibody served as a standard.

Alternatively, the concentration of antibodies and derivatives in cell culture supernatants was measured by Sandwich-IgG-ELISA. Briefly, StreptaWell High Bind Strepatavidin A-96 well microtiter plates (Roche) were coated with 100 μL/well biotinylated anti-human IgG capture molecule F(ab')2<h-Fcgamma> BI (Dianova) at 0.1 μg/mL for 1 h at room temperature or alternatively over night at 4° C. and subsequently washed three times with 200 μL/well PBS, 0.05% Tween (PBST, Sigma). 100 μL/well of a dilution series in PBS (Sigma) of the respective antibody containing cell culture supernatants was added to the wells and incubated for 1-2 h on a microtiterplate shaker at room temperature. The wells were washed three times with 200 μL/well PBST and bound antibody was detected with 100 μl F(ab')2<hFcgamma>POD (Dianova) at 0.1 μg/mL as detection antibody for 1-2 h on a microtiterplate shaker at room temperature. Unbound detection antibody was washed away three times with 200 μL/well PBST and the bound detection antibody was detected by addition of 100 μL ABTS/well. Determination of absorbance was performed on a Tecan Fluor Spectrometer at a measurement wavelength of 405 nm (reference wavelength 492 nm).

Purification of Bispecific Antibodies

Bispecific antibodies were purified from cell culture supernatants by affinity chromatography using Protein A-Sepharose™ (GE Healthcare, Sweden) and Superdex200 size exclusion chromatography. Briefly, sterile filtered cell culture supernatants were applied on a HiTrap ProteinA HP (5 ml) column equilibrated with PBS buffer (10 mM $Na_2HPO_4$, 1 mM $KH_2PO_4$, 137 mM NaCl and 2.7 mM KCl, pH 7.4). Unbound proteins were washed out with equilibration buffer. Antibody and antibody variants were eluted with 0.1 M citrate buffer, pH 2.8, and the protein containing fractions were neutralized with 0.1 ml 1 M Tris, pH 8.5. Then, the eluted protein fractions were pooled, concentrated with an Amicon Ultra centrifugal filter device (MWCO: 30 K, Millipore) to a volume of 3 ml and loaded on a Superdex200 HiLoad 120 ml 16/60 gel filtration column (GE Healthcare, Sweden) equilibrated with 20 mM Histidin, 140 mM NaCl, pH 6.0. Fractions containing purified bispecific antibodies with less than 5% high molecular weight aggregates were pooled and stored as 1.0 mg/ml aliquots at −80° C.

SDS-PAGE

The NuPAGE® Pre-Cast gel system (Invitrogen) was used according to the manufacturer's instruction. In particular, 4-20% NuPAGE® Novex® TRIS-Glycine Pre-Cast gels and a Novex® TRIS-Glycine SDS running buffer were used. (see e.g. FIG. 3). Reducing of samples was achieved by adding NuPAGE® sample reducing agent prior to running the gel.

Analytical Size Exclusion Chromatography

Size exclusion chromatography for the determination of the aggregation and oligomeric state of antibodies was performed by HPLC chromatography. Briefly, Protein A purified antibodies were applied to a Tosoh TSKgel G3000SW column in 300 mM NaCl, 50 mM KH2PO4/K2HPO4, pH 7.5 on an Agilent HPLC 1100 system or to a Superdex 200 column (GE Healthcare) in 2×PBS on a Dionex HPLC-System. The eluted protein was quantified by UV absorbance and integration of peak areas. BioRad Gel Filtration Standard 151-1901 served as a standard. (see e.g. FIG. 4).

Mass Spectrometry

The total deglycosylated mass of crossover antibodies was determined and confirmed via electrospray ionization mass spectrometry (ESI-MS). Briefly, 100 μg purified antibodies were deglycosylated with 50 mU N-Glycosidase F (PN-GaseF, ProZyme) in 100 mM KH2PO4/K2HPO4, pH 7 at 37° C. for 12-24 h at a protein concentration of up to 2 mg/ml and subsequently desalted via HPLC on a Sephadex G25 column (GE Healthcare). The mass of the respective heavy and light chains was determined by ESI-MS after deglycosylation and reduction. In brief, 50 μg antibody in 115 μl were incubated with 60 μl 1M TCEP and 50 μl 8 M Guanidine-hydrochloride subsequently desalted. The total mass and the mass of the reduced heavy and light chains was determined via ESI-MS on a Q-Star Elite MS system equipped with a NanoMate source.

Generation of HEK293-Tie2 Cell Line

In order to determine the interference of Angiopoietin-2 antibodies with ANGPT2 stimulated Tie2 phosphorylation and binding of ANGPT2 to Tie2 on cells a recombinant HEK293-Tie cell line was generated. Briefly, a pcDNA3 based plasmid (RB22-pcDNA3 Topo hTie2) coding for full-length human Tie2 (SEQ ID 108) under control of a CMV promoter and a Neomycin resistance marker was transfected using Fugene (Roche Applied Science) as transfection reagent into HEK293 cells (ATCC) and resistant cells were selected in DMEM 10% FCS, 500 μg/ml G418. Individual clones were isolated via a cloning cylinder, and subsequently analyzed for Tie2 expression by FACS. Clone 22 was identified as clone with high and stable Tie2 expression even in the absence of G418 (HEK293-Tie2 clone22). HEK293-Tie2 clone22 was subsequently used for cellular assays: ANGPT2 induced Tie2 phosphorylation and ANGPT2 cellular ligand binding assay.

ANGPT2 Induced Tie2 Phosphorylation Assay

Inhibition of ANGPT2 induced Tie2 phosphorylation by ANGPT2 antibodies was measured according to the following assay principle. HEK293-Tie2 clone22 was stimulated with ANGPT2 for 5 minutes in the absence or presence of ANGPT2 antibody and P-Tie2 was quantified by a sandwich ELISA. Briefly, 2×105 HEK293-Tie2 clone 22 cells per well were grown over night on a Poly-D-Lysine coated 96 well-microtiter plate in 100 μl DMEM, 10% FCS, 500 μg/ml Geneticin. The next day a titration row of ANGPT2 antibodies was prepared in a microtiter plate (4-fold concentrated, 75 μl final volume/well, duplicates) and mixed with 75 μl of an ANGPT2 (R&D systems #623-AN] dilution (3.2 μg/ml as 4-fold concentrated solution). Antibodies and ANGPT2 were pre-incubated for 15 min at room temperature. 100 μl of the mix were added to the HEK293-Tie2 clone 22 cells (pre-incubated for 5 min with 1 mM NaV3O4, Sigma #S6508) and incubated for 5 min at 37° C. Subsequently, cells were washed with 200 μl ice-cold PBS+1 mM NaV3O4 per well and lysed by addition of 120 μl lysis buffer (20 mM Tris, pH 8.0, 137 mM NaCl, 1% NP-40, 10% glycerol, 2 mM EDTA, 1 mM NaV3O4, 1 mM PMSF and 10 μg/ml Aprotinin) per well on ice. Cells were lysed for 30 min at 4° C. on a microtiter plate shaker and 100 μl lysate were transferred directly into a p-Tie2 ELISA microtiter plate (R&D Systems, R&D #DY990) without previous centrifugation and without total protein determination. P-Tie2 amounts were quantified according to the manufacturer's instructions and IC50 values for inhibition were determined using XLfit4 analysis plug-in for Excel (Dose-response one site, model 205). IC50 values can be compared within on experiment but might vary from experiment to experiment.

VEGF Induced HUVEC Proliferation Assay

VEGF induced HUVEC (Human Umbilical Vein Endothelial Cells, Promocell #C-12200) proliferation was chosen to measure the cellular function of VEGF antibodies. Briefly, 5000 HUVEC cells (low passage number, ≤5 passages) per 96 well were incubated in 100 μl starvation medium (EBM-2

Endothelial basal medium 2, Promocell # C-22211, 0.5% FCS, Penicilline/Streptomycine) in a collagen I-coated BD Biocoat Collagen I 96-well microtiter plate (BD #354407/35640 over night. Varying concentrations of antibody were mixed with rhVEGF (30 ngl/ml final concentration, BD #354107) and pre-incubated for 15 minutes at room temperature. Subsequently, the mix was added to the HUVEC cells and they were incubated for 72 h at 37° C., 5% CO2. On the day of analysis the plate was equilibrated to room temperature for 30 min and cell viability/proliferation was determined using the CellTiter-Glo™ Luminescent Cell Viability Assay kit according to the manual (Promega, # G7571/2/3). Luminescence was determined in a spectrophotometer.

Example 1a

Expression & Purification of Bispecific, Bivalent Domain Exchanged <VEGF-ANG-2> Antibody Molecules XMab According the procedures described in the materials and methods above, the bispecific, bivalent domain exchanged <VEGF-ANG-2> antibody molecules XMab1, XMab1 and XMab3 were expressed and purified. The VH and VL of <VEGF> part (SEQ ID NO:1 and SEQ ID NO:2) are based on bevacizumab. The VH of <ANG2> part (SEQ ID NO:3) was derived by a E6Q mutation (the original amino acid glutamic acid (E) at position 6 was replaced by glutamine (Q)) of the VH sequence of ANG2i-LC06 (which is described in the PCT application No. PCT/EP2009/007182 (WO2010/040508)—and which is further maturated fragment of a sequence obtained via phage display). The VL of <ANG2> part (SEQ ID NO:4) was derived from the VL sequences ANG2i-LC06 (see PCT application No. PCT/EP2009/007182 (WO2010/040508)). The bispecific, bivalent domain exchanged <VEGF-ANG-2> antibody molecules XMab1, XMab2 and XMab3 were expressed and purified. The relevant light and heavy chain amino acid sequences of these bispecific, bivalent antibodies are given in SEQ ID NO: 5-8 (XMab1), in SEQ ID NO: 9-12 (XMab2), and in SEQ ID NO: 13-16 (XMab3). For an exemplary structure see FIG. 1.

| Key data | XMab1 | XMab2 | XMab3 |
|---|---|---|---|
| Expression (Yield) | 32 μg/mL | 10 μg/mL | 39 μg/mL |
| Purification (Yield, Prot. A. homog.) | 31 mg/L, 64% | 8 μg/mL, 80% | — |

The bispecific, bivalent <VEGF-ANG-2> antibodies XMab4, XMab5 and XMab6 (with the relevant light and heavy chain amino acid sequences given in SEQ ID NO: 17-20 (XMab4), in SEQ ID NO: 21-24 (XMab5), and in SEQ ID NO: 25-28 (XMab6)) are expressed and purified analogously.

Binding affinities and other properties were or are determined as described.

Example 1b

Expression & Purification Bispecific, Bivalent <VEGF-ANG-2> Antibody Molecules OAscFab According to the procedures described in the materials and methods above, the bispecific, bivalent <VEGF-ANG-2> antibody molecules OAscFab1, OAscFab2, OAscFab3 were expressed and purified. The VH and VL of <VEGF> part (SEQ ID NO:1 and SEQ ID NO:2) are based on bevacizumab. The VH of <ANG2> E6Q part (SEQ ID NO:3) was derived by a E6Q mutation (the original amino acid glutamic acid (E) at position 6 was replaced by glutamine (Q)) of the VH sequences ANG2i-LC06 (which is described in the PCT application No. PCT/EP2009/007182 (WO2010/040508)—and which is further maturated fragment of a sequence obtained via phage display). The VL of <ANG2> E6Q part (SEQ ID NO:4) was derived from the VL sequence of ANG2i-LC06 (see PCT application No. PCT/EP2009/007182 (WO2010/040508) (WO2010/040508)). The relevant light and heavy chain amino acid sequences of these bispecific, bivalent antibodies are given in SEQ ID NO: 29-31 (OAscFab1), in SEQ ID NO: 32-34 (OAscFab2), and in SEQ ID NO: 35-37 (OAscFab3). For an exemplary structure see FIG. 2a. Expression of OAscFab1, OAscFab1, OAscFab2 and OAscFab3 was confirmed by Western blot. Purification of OAscFab2 and OAscFab3 led to the following yields.

| Antibody | Supernatant | Protein A Yield | Protein A Mono. | SEC Yield | SEC Monomer |
|---|---|---|---|---|---|
| OAscFab2 | 0.5 L | 36.0 mg | 86% | 21.7 mg | >95% |
| OAscFab3 | 0.5 L | 29.3 mg | 85% | 17.7 mg | >95% |

Binding affinities and other properties are determined as described.

Example 1c

Expression & Purification Bispecific, Bivalent Domain Exchanged <VEGF-ANG-2> Antibody Molecules OAscXFab According the procedures described in the materials and methods above, the bispecific, bivalent domain exchanged <VEGF-ANG-2> antibody molecules OAscXFab1, OAscXFab2, OAscXFab3, were expressed and purified. The VH and VL of <VEGF> part (SEQ ID NO:1 and SEQ ID NO:2) are based on bevacizumab. The VH of <ANG2> E6Q part (SEQ ID NO:3) was derived by a E6Q mutation (the original amino acid glutamic acid (E) at position 6 was replaced by glutamine (Q)) of the VH sequences ANG2i-LC06 (which is described in the PCT application No. PCT/EP2009/007182 (WO2010/040508)—and which is further maturated fragment of a sequence obtained via phage display). The VL of <ANG2> E6Q part (SEQ ID NO:4) was derived from the VL sequence of ANG2i-LC06 (see PCT application No. PCT/EP2009/007182 (WO2010/040508)). The relevant light and heavy chain amino acid sequences of these bispecific, bivalent antibodies are given in SEQ ID NO: 38-40 (OAscXFab1), in SEQ ID NO: 41-43 (OAscXFab2), and in SEQ ID NO: 44-46 (OAscXFab3). For an exemplary structure see FIG. 2b (OAscXFab1) and FIG. 2c (OAscXFab2, OAscXFab3). Expression was confirmed by Western blot.

| Key data | OAscXFab1 | OAscXFab2 | OAscXFab3 |
|---|---|---|---|
| Expression (Yield) | 23 μg/mL | 23 μg/mL | 26 μg/mL |

Binding affinities and other properties are determined as described.

Example 2

Stability of Bispecific Antibodies

Denaturation Temperature (SYPRO Orange Method)

To determine the temperature at which protein denaturation (i.e. temperature-induced loss of protein structure) occurs, a method was used that relies a hydrophobic fluorescent dye (SYPRO orange, Invitrogen) that exhibits strong fluorescence in hydrophobic environments. Upon protein denaturation, hydrophobic patches become exposed to the solvent, leading to an increased fluorescence. At temperatures above the denaturation temperature, fluorescence intensities decrease again, hence the temperature at which a maximum intensity is reached is defined as the denaturation temperature. The method is described by Ericsson, U. B., et al., Anal Biochem 357 (2006) 289-298 and He, F., et al., Journal of Pharmaceutical Sciences 99 (2010) 1707-1720.

Proteins samples at a concentration of approx. 1 mg/mL in 20 mM His/HisCl, 140 mM NaCl, pH 6.0 were mixed with SYPRO orange (5000× stock solution) to reach a final dilution of 1:5000. A volume of 20 μL was transferred into a 384 well-plate and temperature-dependent fluorescence was recorded in a LightCycler® 480 Real-Time PCR System (Roche Applied Sciences) at a heat rate of 0.36° C./min.

Aggregation Temperature by Dynamic Light Scattering (DLS)

The temperature at which thermally induced protein aggregation occurs was determined by dynamic light scattering (DLS). DLS yields information on the size distribution of macromolecules in solution, derived from fluctuations of scattered light intensities on a microsecond scale. When samples are heated up gradually, aggregation starts at a certain temperature, giving rise to growing particle sizes. The temperature at which particle sizes begin to increase is defined as the aggregation temperature. Aggregation and denaturation temperatures need not necessarily be identical since denaturation may not necessarily be a prerequisite for aggregation.

For aggregation temperature measurements, a DynaPro DLS platereader (Wyatt technologies) was used. Preceding the measurement, samples were filtered via 384-well filter plates (Millipore MultiScreen 384-well Filtration System, 0.45 μm) into optical 384 well plates (Corning #3540). A sample volume of 35 μL was used at a protein concentration of approx. 1 mg/mL in formulation buffer (20 mM citrate, 180 mM sucrose, 20 mM arginine, 0.02% polysorbate 20). Each well was covered with 20 μL paraffin oil (Sigma) to avoid evaporation. Samples were heated from 25° C. to 80° C. at a rate of 0.05° C./min and DLS data were acquired continuously for a maximum number of 15 samples per run.

Aggregation Rate Per DLS

DLS is a sensitive method for detecting aggregates of macromolecules in solution, since aggregates give rise to strong light scattering signals. Hence, the tendency of a molecule to aggregate can be followed over time by repeated acquisition of DLS data. To accelerate potential aggregation to practical rates, measurements were conducted at 50° C.

Sample preparation was performed as described above. DLS data were recorded for up to 100 hours. Aggregation rates (nm/day) were calculated as the slope of a linear fit of average diameters over time.

Stability in Formulation Buffer

To assess bispecific molecules for their stability with regard to aggregation/fragmentation, samples were incubated for 3 weeks at 40° C. in formulation buffer (20 mM citrate, 180 mM sucrose, 20 mM arginine, 0.02% polysorbate 20) at a protein concentration of approximately 1 mg/mL. A control sample was stored for 3 weeks at −80° C.

Size exclusion chromatography for the quantification of aggregates and low-molecular weight (LMW) species was performed by HPLC. An amount of 25-100 μg of protein was applied to a Tosoh TSKgel G3000SWXL column in 300 mM NaCl, 50 mM potassium phosphate, pH 7.5 on an Ultimate3000 HPLC system (Dionex). The eluted protein was quantified by UV absorbance at 280 nm.

Results

| Method | Stability of XMab1 (SEQ ID NO: 5-8) |
|---|---|
| Denaturation temperature (SYPRO orange method) | 71° C. |
| Aggregation temperature by Dynamic Light Scattering (DLS) | 65° C. |
| Aggregation rate per DLS | 0.04 nm/day |
| Stability in formulation buffer (difference between 40° C. and −80° C. after 3 weeks storage) | ΔHMW: 0.6 area % ΔLMW: 0.5 area % ΔMonomer: −1.2 area % |

Example 3

Binding Properties of Bispecific Antibody <VEGF-Ang-2>

A) Binding Properties Characterized by Surface Plasmon Resonance (SPR) Analysis

Simultaneous binding of both antigens was confirmed by applying Surface Plasmon Resonance (SPR) using a BIAcore T100 instrument (GE Healthcare Biosciences AB, Uppsala, Sweden). VEGF was immobilized to a CM5 Sensorchip using standard amine coupling chemistry. In a first step, <VEGF-Ang-2>XMAb was injected at a concentration of 10 μg/ml in HBS buffer (10 mM HEPES, 150 mM NaCl, 0.05% Tween 20, pH 7.4) at 25° C. After binding of the antibody to the immobilized VEGF, hAng-2 was injected at 10 μg/ml in a second step (FIG. 3)

In a further experiment the affinity and binding kinetics of <VEGF-Ang-2> XMab were determined. Briefly, goat<hIgG-Fcgamma> polyclonal antibodies were immobilized on a CM4 chip via amine coupling for presentation of the bispecific antibody against Ang-2 and VEGF. Binding was measured in HBS buffer at 25° C. or 37° C. Purified Ang-2-His (R&D systems or in house purified) or VEGF (R&D systems or in house purified) was added in various concentrations between 0.37 nM and 30 nM or between 3.7 nM and 200 nM in solution. Association was measured by an injection of 3 minutes; dissociation was measured by washing the chip surface with HBS buffer for 10 minutes and a KD value was estimated using a 1:1 Langmuir binding model. Due to heterogenity of the Ang-2 preparation no 1:1 binding could be observed. Therefore KD values are apparent values. The determined affinity of <VEGF-Ang-2> XMab to VEGF was extremely high, the calculated off-rate was out of Biacore specifications even at 37° C. In Table 1 the binding constants for both antigens are summarized.

TABLE 1

Kinetic parameters of <VEGF-Ang-2> XMab1 binding to Ang-2 and VEGF

| Analyte | Apparent ka (1/Ms) | Apparent kd (1/s) | Apparent KD (M) |
|---|---|---|---|
| Ang-2 | 2.7E+06 | 6.3E−04 | 2.4E−10 |
| VEGF | 1.2E+05 | <1E−06 | <1E−10 |

B) Assay for Quantification of Binding Active Bispecific <Ang2/VEGF> XMab1

Figure 5:
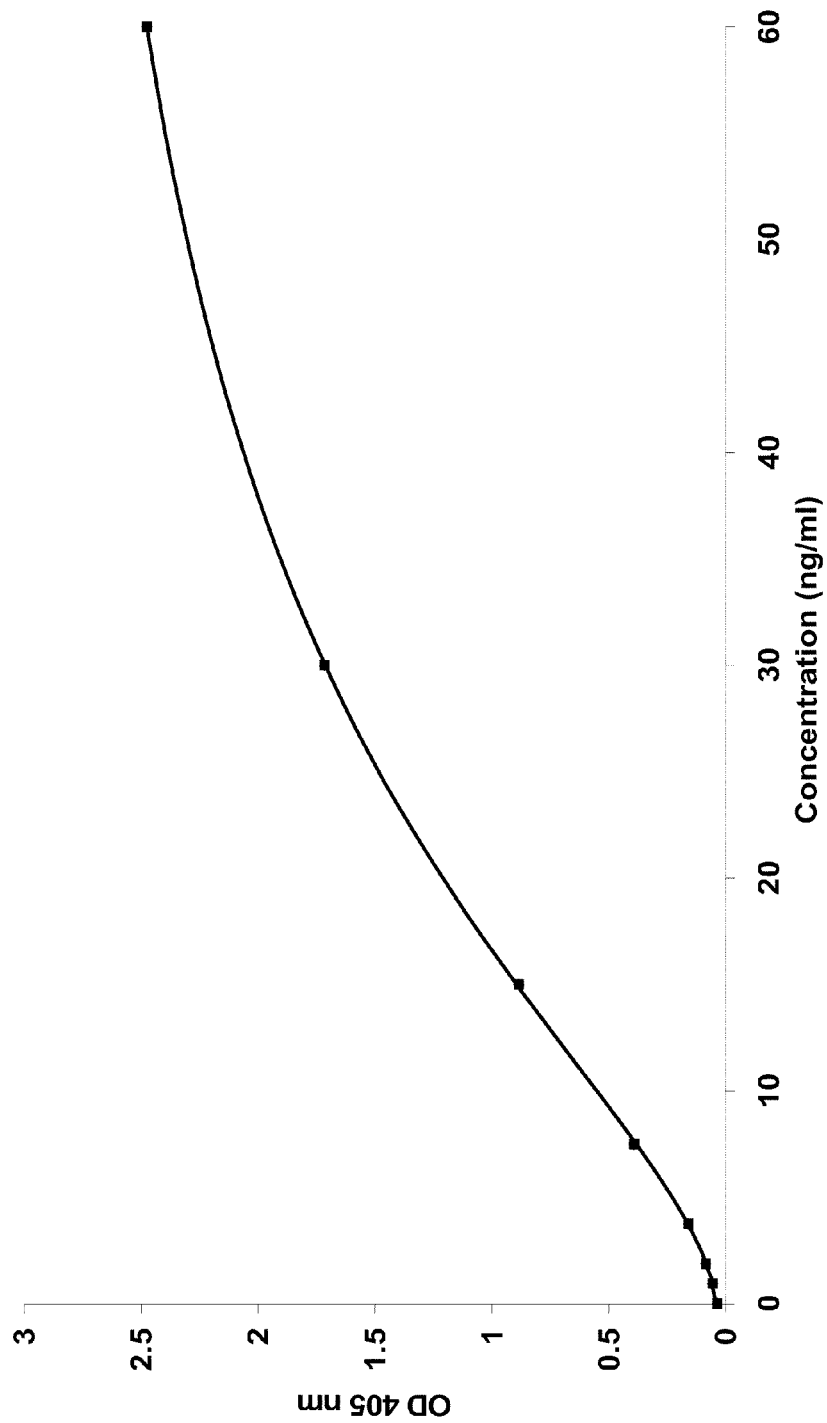

Additionally to the SPR analysis, an ELISA was established to quantify the amount of binding active bispecific mAb<Ang2/VEGF> antibodies. In this assay, hAng2 is directly coated to the wells of a maxisorp microtiter plate (MTP) in the first step. Meanwhile, the samples/reference standards (mAb<Ang2/VEGF>) were pre-incubated in the wells of another MTP with digoxigenylated VEGF. After pre-incubation and coating, excess of unbound Ang2 was removed by washing the Ang2 coated MTP. The pre-incubated mixture of <Ang2/VEGF> and VEGF-Dig was then transferred to the hAng2 coated MTP and incubated. After incubation, the excess of pre-incubation solution was removed by washing followed by incubation with a horseradish peroxidase labeled anti-digoxigenin antibody. The antibody-enzyme conjugate catalyzes the color reaction of the ABTS® substrate. The signal was measured by ELISA reader at 405 nm wavelength (reference wavelength: 490 nm ([405/490] nm)). Absorbance values of each sample were determined in duplicates. (A scheme exemplifying this test system is shown in FIG. 4 and Calibration curve of ELISA for quantification is shown in FIG. 5)

Example 4

Tie2 Phosphorylation

In order to confirm that the anti-ANGPT2 related activities are retained in the bispecific bivalent <VEGF-ANGPT2> antibody XMAb1 Tie2 phosphorylation assay was performed. The efficacy of XMAb1 was determined in the ANGPT2 stimulated Tie2 phosphorylation assay as described above.

It was shown that XMAb1 interferes with ANGPT2 stimulated Tie2 phosphorylation in the ANGPT2 stimulated Tie2 phosphorylation assay as described above. IC50 for XMAb1 was 7.4 nM +/−2.3.

Example 5

Inhibition of huANG-2 Binding to Tie-2 (ELISA)

The interaction ELISA was performed on 384 well microtiter plates (MicroCoat, DE, Cat. No. 464718) at RT. After each incubation step plates were washed 3 times with PBST. ELISA plates were coated with 5 µg/ml Tie-2 protein for 1 hour (h). Thereafter the wells were blocked with PBS supplemented with 0.2% Tween-20 and 2% BSA (Roche Diagnostics GmbH, DE) for 1 h. Dilutions of purified bispecific Xmab antibodies in PBS were incubated together with 0.2 µg/ml huAngiopoietin-2 (R&D Systems, UK, Cat. No. 623-AN) for 1 h at RT. After washing a mixture of 0.5 µg/ml biotinylated anti-Angiopoietin-2 clone BAM0981 (R&D Systems, UK) and 1:3000 diluted streptavidin HRP (Roche Diagnostics GmbH, DE, Cat. No. 11089153001) was added for 1 h. Thereafter the plates were washed 3 times with PBST. Plates are developed with freshly prepared ABTS reagent (Roche Diagnostics GmbH, DE, buffer #204 530 001, tablets #11 112 422 001) for 30 minutes at RT. Absorbance was measured at 405 nm and the IC50 was determined. XMab1 showed an inhibition of ANG-2 binding to Tie-2 with an IC50 of 12 nM.

Example 6

Inhibition of hVEGF Binding to hVEGF Receptor (ELISA)

The test was performed on 384 well microtiter plates (MicroCoat, DE, Cat. No. 464718) at RT. After each incubation step plates were washed 3 times with PBST. At the beginning, plates were coated with 1 µg/ml hVEGF-R protein (R&D Systems, UK, Cat. No. 321-FL) for 1 hour (h). Thereafter the wells were blocked with PBS supplemented with 0.2% Tween-20 and 2% BSA (Roche Diagnostics GmbH, DE) for 1 h. Dilutions of purified bispecific XMab antibodies in PBS were incubated together with 0.15 µg/ml huVEGF121 (R&D Systems, UK, Cat. No. 298-VS) for 1 h at RT. After washing a mixture of 0.5 µg/ml anti VEGF clone Mab923 (R&D Systems, UK) and 1:2000 horse radish peroxidase (HRP)-conjugated F(ab')2 anti mouse IgG (GE Healthcare, UK, Cat. No. NA9310V) was added for 1 h. Thereafter the plates were washed 6 times with PBST. Plates were developed with freshly prepared ABTS reagent (Roche Diagnostics GmbH, DE, buffer #204 530 001, tablets #11 112 422 001) for 30 minutes at RT. Absorbance was measured at 405 nm and the IC50 was determined. XMab1 showed an inhibition of Inhibition of VEGF binding to VEGF Receptor with an IC50 of 10 nM.

Example 7

HUVEC Proliferation

In order to confirm that the anti-VEGF related activities are retained in the bispecific bivalent <VEGF-ANG2> antibody XMAb1 VEGF-induced HUVEC proliferation assay was performed. It was shown that XMAb1 interferes with VEGF-induced HUVEC proliferation in a comparable manner as bevacizumab in the VEGF-induced HUVEC proliferation assay as described above. XMAb 1 interferes in a concentration dependent manner with VEGF-induced HUVEC proliferation comparable to the parental antibody bevacizumab (Avastin). IC50 was 1.1 nM for bevacizumab and 2.3 nM for XMAb.

Example 8

Mouse Cornea Micropocket Angiogenesis Assay 8 to 10 weeks old female Balb/c mice were purchased from Charles River, Sulzfeld, Germany. The protocol was modified according to the method described by Rogers, M. S., et al., Nat Protoc 2 (2007) 2545-2550. Briefly, micropockets with a width of about 500 µm were prepared under a microscope at approximately 1 mm from the limbus to the top of the cornea using a surgical blade and sharp tweezers in the anesthetized mouse. The disc (Nylaflo®, Pall Corporation, Michigan) with a diameter of 0.6 mm was implanted and the surface of the implantation area was smoothened. Discs were incubated in corresponding growth factor or in vehicle for at least 30 min. After 3, 5 and 7 days (or alternatively only after 3 days), eyes were photographed and vascular response was measured. The assay was quantified by calculating the percentage of the area of new vessels per total area of the cornea.

The discs were loaded with 300 ng VEGF or with PBS as a control and implanted for 7 days. The outgrowth of vessels from the limbus to the disc was monitored over time on day 3, 5 and 7. One day prior to disc implantation the antibodies (<Ang-2/VEGF> XMAb1, <hVEGF> Avastin (bevacizumab)) were administered intravenously at a dose of 10 mg/kg for Avastin and XMAb1. Animals in the control group received vehicle. The application volume was 10 ml/kg.

Figure 6:
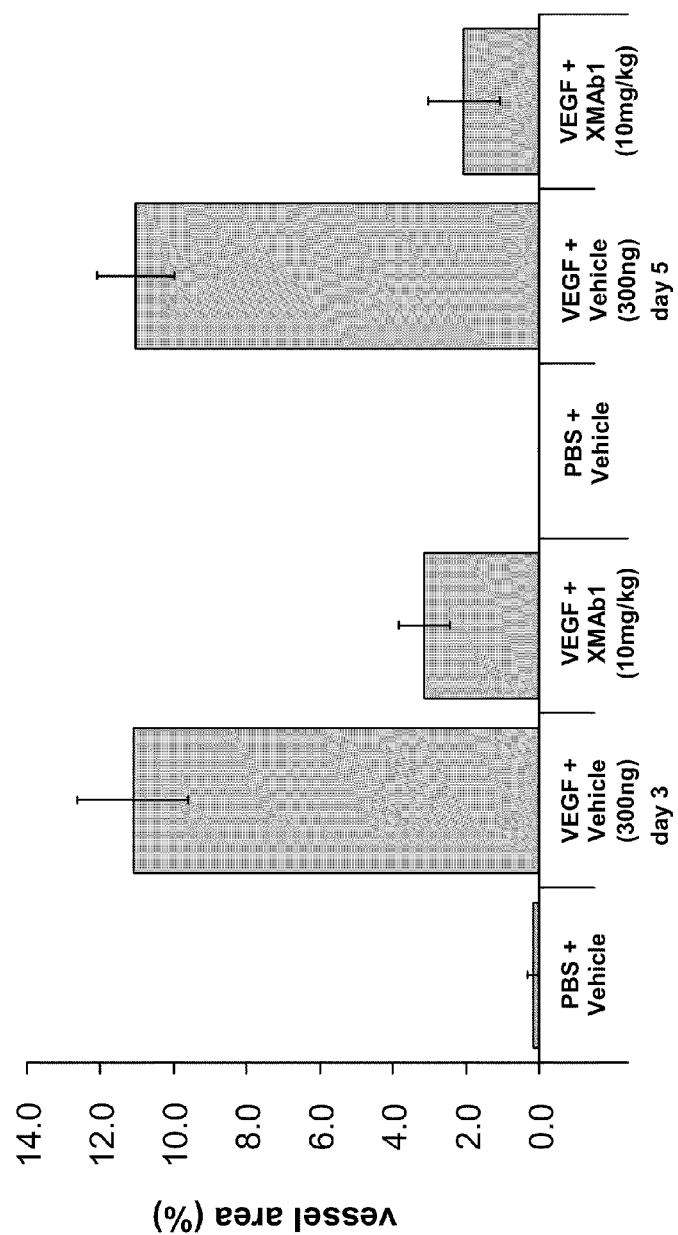

To test the effect of XMAb1 on VEGF-induced angiogenesis in vivo, we performed the mouse corneal angiogenesis assay. In this assay a VEGF soaked Nylaflo disc is implanted into a pocket of the avascular cornea at a fixed distance to the limbal vessels. Vessels immediately grow into the cornea towards the developing VEGF gradient. Our results demonstrate that systemic administration of the XMAb1 (10 mg/kg) almost completely inhibited the outgrowth of the vessel from the limbus towards the VEGF gradient from study day 3 to 5 (FIG. 6). In a further experiment, direct comparison studies were performed. The discs were loaded with 300 ng VEGF or with PBS as a control and implanted for 3 days. The outgrowth of vessels from the limbus to the disc was monitored over time on day 3. One day prior to disc implantation the antibodies (bispecific <Ang-2/VEGF> antibody XMAb1, parent <VEGF> antibody bevacizumab (Avastin), parent <Ang-2> antibody ANG2i-LC06, and the combination of <VEGF> antibody bevacizumab (Avastin) and <Ang-2> antibody ANG2i-LC06) were administered intravenously at a dose of 10 mg/kg for bevacizumab (Avastin), 10 mg/kg for XMAb1, 10 mg/kg for bevacizumab (Avastin), and 10 mg/kg for ANG2i-LC06. The combination of bevacizumab (Avastin) and ANG2i-LC06 was administered with 10 mg/kg for bevacizumab (Avastin) and 10 mg/kg for ANG2i-LC06. Animals in the control group received vehicle. The application volume was 10 ml/kg.

Figure 7:
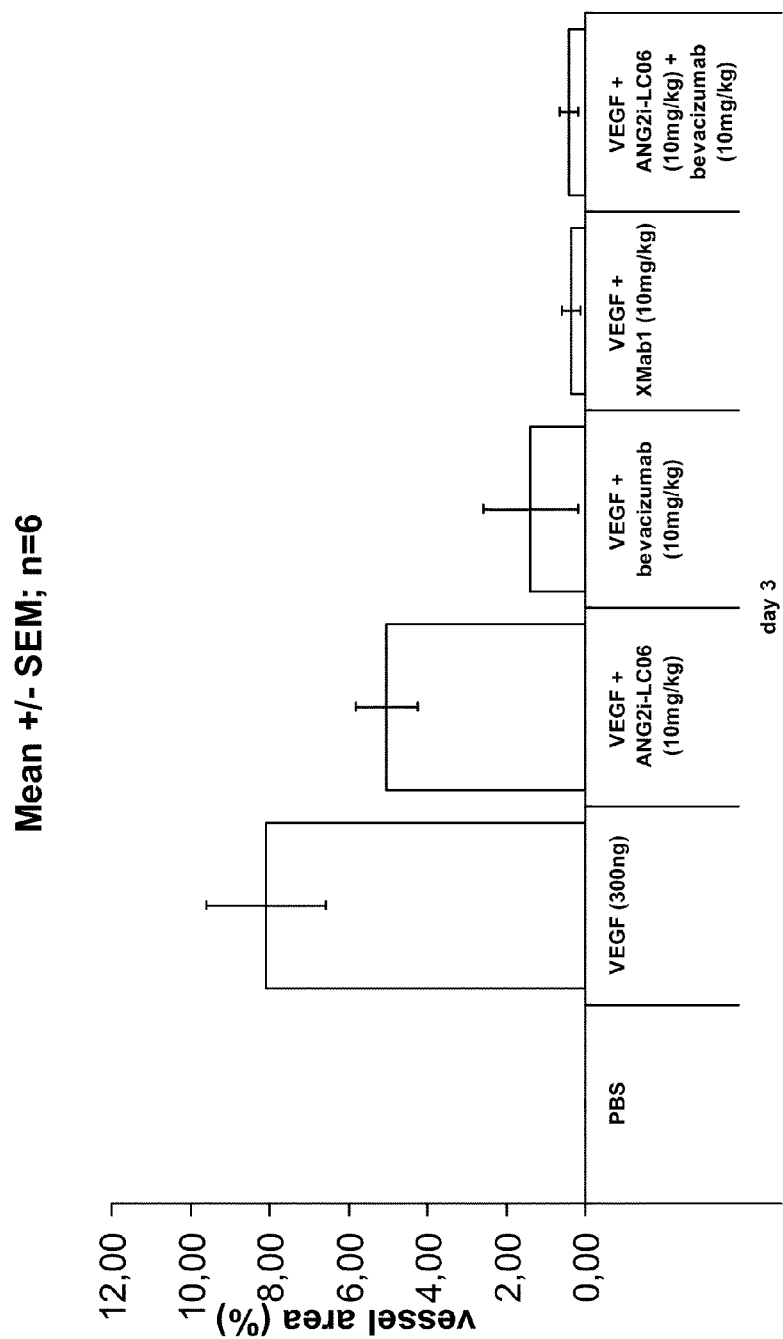
FIG. 7 Mouse corneal angiogenesis assay—inhibition of angiogenesis/vessel outgrowth from the limbus towards the VEGF gradient by administration of a bispecific antibody according to the invention—Comparison of the bispecific <Ang2/VEGF> antibody XMab1, the <Ang2> Mab ANG2i-LC06 (LC06), the <VEGF> Mab bevacizumab (Avastin) and the combination ANG2i-LC06 and <VEGF> Mab bevacizumab (Avastin).

Our results (see FIG. 7 and Table below) demonstrate that systemic administration of the XMAb1 (10 mg/kg) almost completely inhibited the outgrowth of the vessel from the limbus towards the VEGF gradient at study day 3 comparable to the combination of bevacizumab and ANG2i-LC06. Anti-Ang-2 monotherapy in contrast only slightly inhibited VEGF-induced angiogenesis (FIG. 7). The maximum effect could already be achieved at lower concentrations of 10 mg/kg XMAb1 compared to the combination of 10 mg/kg of ANG2i-LC06+10 mg/kg of bevacizumab (Avastin).

TABLE

Percent inhibition of VEGF-induced angiogenesis on day 3 in a Mouse cornea micropocket angiogenesis assay

|  |  | % inhibition of VEGF-induced angiogenesis |
|---|---|---|
| day 3 | VEGF (300 ng) | 0 |
|  | ANG2i-LC06 (10 mg/kg) | 38 |
|  | Bevacizumab (Avastin) (10 mg/kg) | 83 |
|  | XMab1 (10 mg/kg) | 96 |
|  | Ang2i-LC06 (10 mg/kg) + bevacizumab (Avastin) (10 mg/kg) | 95 |

Example 9

In Vivo Efficacy of Bispecific Antibody <VEGF-ANG-2> Antibody in Colo205 Xenograft Model in Scid Beige Mice Cell Lines and Culture Conditions:

Colo205 human colorectal cancer cells (ATCC No. CCL-222). Tumor cell line were routinely cultured in RPMI 1640 medium (PAA, Laboratories, Austria) supplemented with 10% fetal bovine serum (PAA Laboratories, Austria) and 2 mM L-glutamine, at 37° C. in a water-saturated atmosphere at 5% $CO_2$. Passage 2-5 is used for transplantation.

Animals:

Female SCID beige mice; age 4-5 weeks at arrival (purchased from Charles River Germany) were maintained under specific-pathogen-free condition with daily cycles of 12 h light/12 h darkness according to committed guidelines (GV-Solas; Felasa; TierschG). Experimental study protocol was reviewed and approved by local government. After arrival animals were maintained in the quarantine part of the animal facility for one week to get accustomed to new environment and for observation. Continuous health monitoring is carried out on regular basis. Diet food (Provimi Kliba 3337) and water (acidified pH 2.5-3) were provided ad libitum. Age of mice at start of the study is about 10 weeks.

Tumor Cell Injection:

At the day of injection, tumor cells were harvested (trypsin-EDTA) from culture flasks (Greiner) and transferred into 50 ml culture medium, washed once and resuspended in PBS. After an additional washing step with PBS and filtration (cell strainer; Falcon 100 μm) the final cell titer was adjusted to $2.5 \times 10^7$/ml. Tumor cell suspension was carefully mixed with transfer pipette to avoid cell aggregation. After this, cell suspension was filled into a 1.0 ml tuberculin syringe (Braun Melsungen) using a wide needle (1.10×40 mm); for injection needle size is changed (0.45×25 mm) and for every injection a new needle was used. Anesthesia was performed using a Stephens inhalation unit for small animals with preincubation chamber (plexiglas), individual mouse nose-mask (silicon) and not flammable or explosive anesthesia compound Isoflurane (cp-pharma) in a closed circulation system. Two days before injection coat of the animals was shaved and for cell injection skin of anaesthetized animals was carefully lifted up with an anatomic forceps and 100 μl cell suspension (=2.5× $10^6$ cells) was injected subcutaneously in the right flank of the animals.

Treatment of Animals

Treatment of animals started at day of randomization at a mean tumor volume of ~100 mm3, respectively. Mice were treated once weekly i.p. with the different compounds as indicated in following table.

| No of animals | Compound | Dose (mg/kg) | Route/Mode of administration |
|---|---|---|---|
| 10 | Xolair | 10 | i.p. once weekly |
| 10 | <VEGF> Avastin | 10 | i.p. once weekly |
| 10 | <ANG-2> Ang2i-LC06 | 10 | i.p. once weekly |
| 10 | Ang2i-LC06 + Avastin | 10 10 | i.p. once weekly i.p. once weekly |
| 10 | XMAb1 | 10 | i.p. once weekly |

Monitoring:

Animals were controlled 2× per week for their health status. Body weights were documented 2× per week after cell injection. The tumor dimensions were measured by caliper beginning on the staging day and subsequently 2 times per week during the whole treatment period. Tumor volume was calculated according to NCI protocol (Tumor weight=½ ab², where "a" and "b" are the long and the short diameters of the tumor, respectively). Termination criteria were the critical tumor mass (up to 1.7 g or Ø>1.5 cm), body weight loss more than 20% from baseline, tumor ulceration or poor general condition of the animals.

Figure 8:
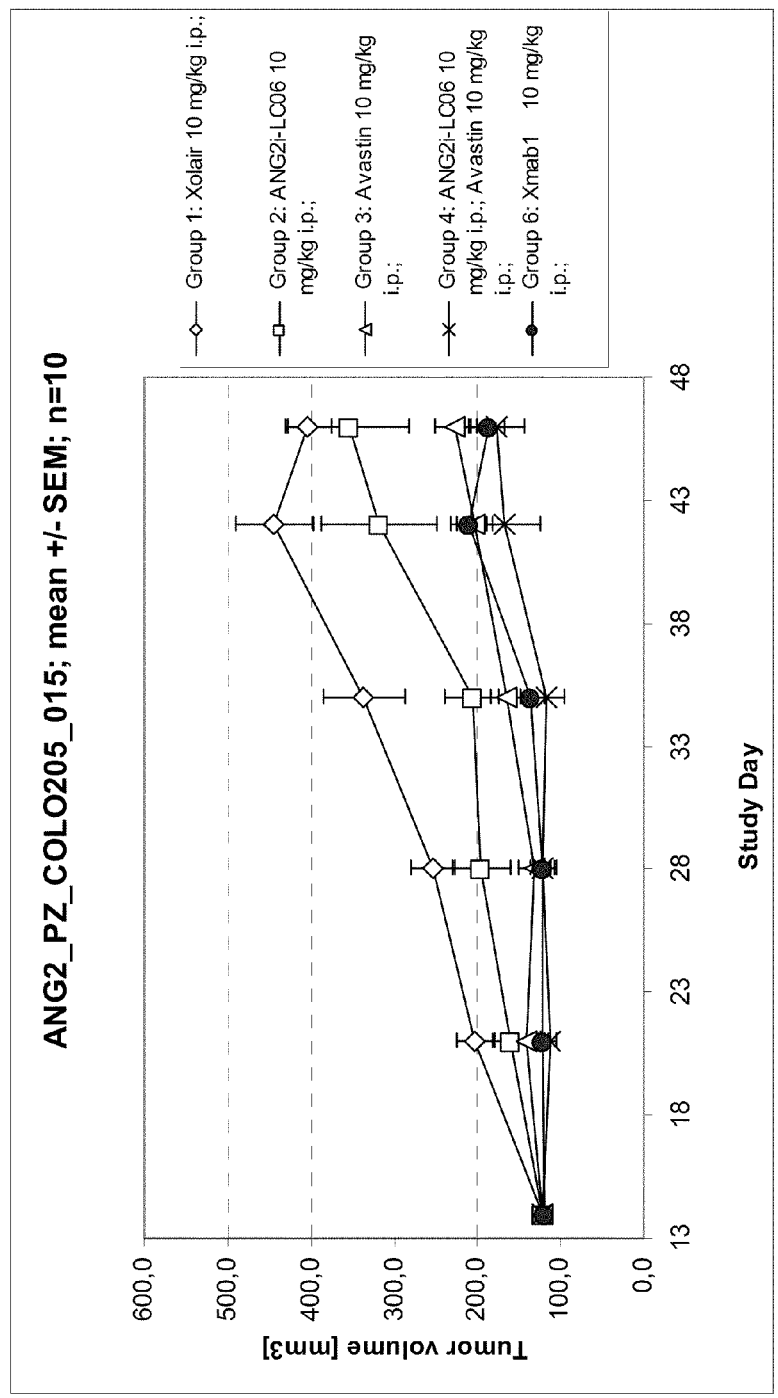
FIG. 8 In vivo tumor growth inhibition in mouse xenograft of human colorectal cancer Colo205 (small tumors) by a bispecific antibody according to the invention—Comparison of the bispecific <Ang2/VEGF> antibody XMab1, the <Ang2> Mab ANG2i-LC06 (LC06), the <VEGF> Mab bevacizumab (Avastin) and the combination ANG2i-LC06 and <VEGF> Mab bevacizumab (Avastin).

The results (see (FIG. 8) show that the bispecific bivalent <VEGF-ANG-2> antibody XMAb1 showed a higher tumor growth inhibition in xenograft tumor model Colo205 in Scid beige mice compared to the treatment with monospecific antibodies. The efficacy of the combination of ANG2i-LC06 and bevacizumab showed comparable results to the XMAb1. Maximal efficacy of XMAb1 was already reached with 10 mg/kg.

In a second experiment the effect of XMAb1 on bigger tumors was analyzed.

Treatment of Animals

Treatment of animals started at day of randomization at a mean tumor volume of ~400 mm3, respectively. Mice were treated once weekly i.p. with the different compounds as indicated in following table.

| No of animals | Compound | Dose (mg/kg) | Route/Mode of administration |
|---|---|---|---|
| 10 | Xolair | 10 | i.p. once weekly |
| 10 | <VEGF> Avastin | 10 | i.p. once weekly |
| 10 | <ANG-2> Ang2i-LC06 | 10 | i.p. once weekly |
| 10 | Ang2i-LC06 + Avastin | 10 10 | i.p. once weekly i.p. once weekly |
| 10 | XMAb1 | 10 | i.p. once weekly |

Monitoring:

Animals were controlled 2× per week for their health status. Body weights were documented 2× per week after cell injection. The tumor dimensions were measured by caliper beginning on the staging day and subsequently 2 times per week during the whole treatment period. Tumor volume is calculated according to NCI protocol (Tumor weight=½ ab², where "a" and "b" are the long and the short diameters of the tumor, respectively). Termination criteria were the critical tumor mass (up to 1.7 g or Ø>1.5 cm), body weight loss more than 20% from baseline, tumor ulceration or poor general condition of the animals.

Figure 9:
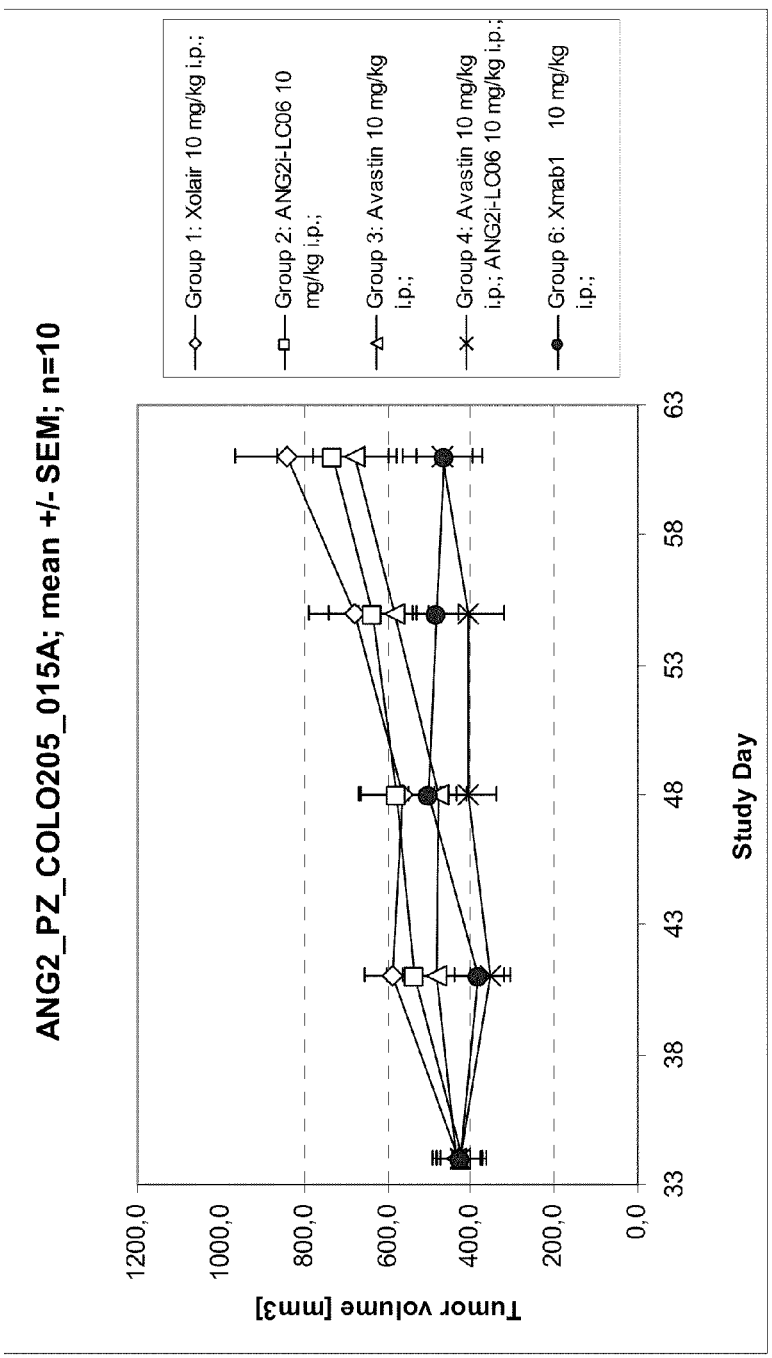
FIG. 9 In vivo tumor growth inhibition in mouse xenograft of human colorectal cancer Colo205 (large tumors) by a bispecific antibody according to the invention—Comparison of the bispecific <Ang2/VEGF> antibody XMab1, the <Ang2> Mab ANG2i-LC06 (LC06), the <VEGF> Mab bevacizumab (Avastin) and the combination ANG2i-LC06 and <VEGF> Mab bevacizumab (Avastin).

The results (see FIG. 9) show that the bispecific bivalent <VEGF-ANG-2> antibody XMAb1 showed a higher tumor growth inhibition in xenograft tumor model Colo205 in Scid beige mice compared to the treatment with monospecific antibodies which showed no efficacy in big tumors compared to the control. The efficacy of the combination of ANG2i-LC06 and bevacizumab showed comparable results to the XMAb1. Maximal efficacy of XMAb1 was already reached with 10 mg/kg.

Taken together the results demonstrate that independent of the tumor size XMAb1 shows superior efficacy compared to the treatment with monospecific antibodies.

Tumor stasis in these models could already be achieved at lower concentrations of 10 mg/kg XMAb1 compared to the combination of 10 mg/kg of ANG2i-LC06+10 mg/kg of Avastin.

Example 10

In Vivo Efficacy of Bispecific Antibody <VEGF-ANG-2> Antibody in Orthotopic KPL-4 Xenograft Model in Scid Beige Mice Tumor Cell Line The human breast cancer cell line KPL-4 ((Kurebayashi, J., et al., Br. J. Cancer 79 (1999) 707-17)) has been established from the malignant pleural effusion of a breast cancer patient with an inflammatory skin metastasis. Tumor cells were routinely cultured in DMEM medium (PAN Biotech, Germany) supplemented with 10% fetal bovine serum (PAN Biotech, Germany) and 2 mM L-glutamine (PAN Biotech, Germany) at 37° C. in a water-saturated atmosphere at 5% $CO_2$. Culture passage was performed with trypsin/EDTA 1× (PAN) splitting three times/week.

Mice

After arrival, female SCID beige mice (age 10-12 weeks; body weight 18-20 g) Charles River, Sulzfeld, Germany) were maintained in the quarantine part of the AALAAC approved animal facility for one week to get them accustomed to the new environment and for observation. Continuous health monitoring was carried out. The mice were kept under SPF-conditions according to the international guidelines (GV-Solas; Felasa; TierschG) with daily cycles of 12 h light/12 h darkness. Diet food (Kliba Provimi 3347) and water (filtered) were provided ad libitum. Experimental study protocol was reviewed and approved by the local government (Regierung von Oberbayern; registration no. 211.2531.2-22/2003).

Tumor Cell Injection

At the day of injection tumor cells were harvested (trypsin-EDTA) from culture flasks (Greiner TriFlask) and transferred into 50 ml culture medium, washed once and resuspended in PBS. After an additional washing step with PBS and filtration (cell strainer; Falcon 0 100 μm) the final cell titer was adjusted to $1.5 \times 10^8$/ml. Tumor cell suspension was carefully mixed with transfer pipette to avoid cell aggregation. Anesthesia is performed using a Stephens inhalation unit for small animals with preincubation chamber (plexiglas), individual mouse nose-mask (silicon) and not flammable or explosive anesthesia compound Isoflurane (Pharmacia-Upjohn, Germany) in a closed circulation system. Two days before injection coat of the animals were shaved. For i.m.f.p. injection cells were injected orthotopically at a volume of 20 μl into the right penultimate inguinal mammary fat pad of each anesthetized mouse. For the orthotopic implantation, the cell suspension was injected through the skin under the nipple using a using a Hamilton microliter syringe and a 30G×½" needle.

Treatment of Animals

Treatment of animals started at day of randomization at a mean tumor volume of ~80 mm3, respectively. Mice were treated once weekly i.p. with the different compounds as indicated in following table.

| No of animals | Compound | Dose (mg/kg) | Route/Mode of administration |
|---|---|---|---|
| 10 | Xolair | 10 | i.p. once weekly |
| 10 | <VEGF> Avastin | 10 | i.p. once weekly |
| 10 | <ANG-2> Ang2i-LC06 | 10 | i.p. once weekly |
| 10 | Ang2i-LC06 + Avastin | 10 10 | i.p. once weekly i.p. once weekly |
| 10 | XMAb1 | 10 | i.p. once weekly |

Monitoring of Tumor Growth

Animals were controlled 2× per week for their health status. Body weights were documented 2× per week after cell injection. The tumor dimensions were measured by caliper on the staging day, at beginning of treatment period 2 times per week. Tumor volume was calculated according to NCI protocol (B. Teicher; Anticancer drug development guide, Humana Press, 1997, Chapter 5, page 92) (Tumor weight=½ ab², where "a" and "b" are the long and the short diameters of the tumor, respectively).

Termination criteria were the critical tumor mass (up to 1.7 g or Ø>1.5 cm), body weight loss more than 20% from baseline, tumor ulceration or poor general condition of the animals.

Figure 10:
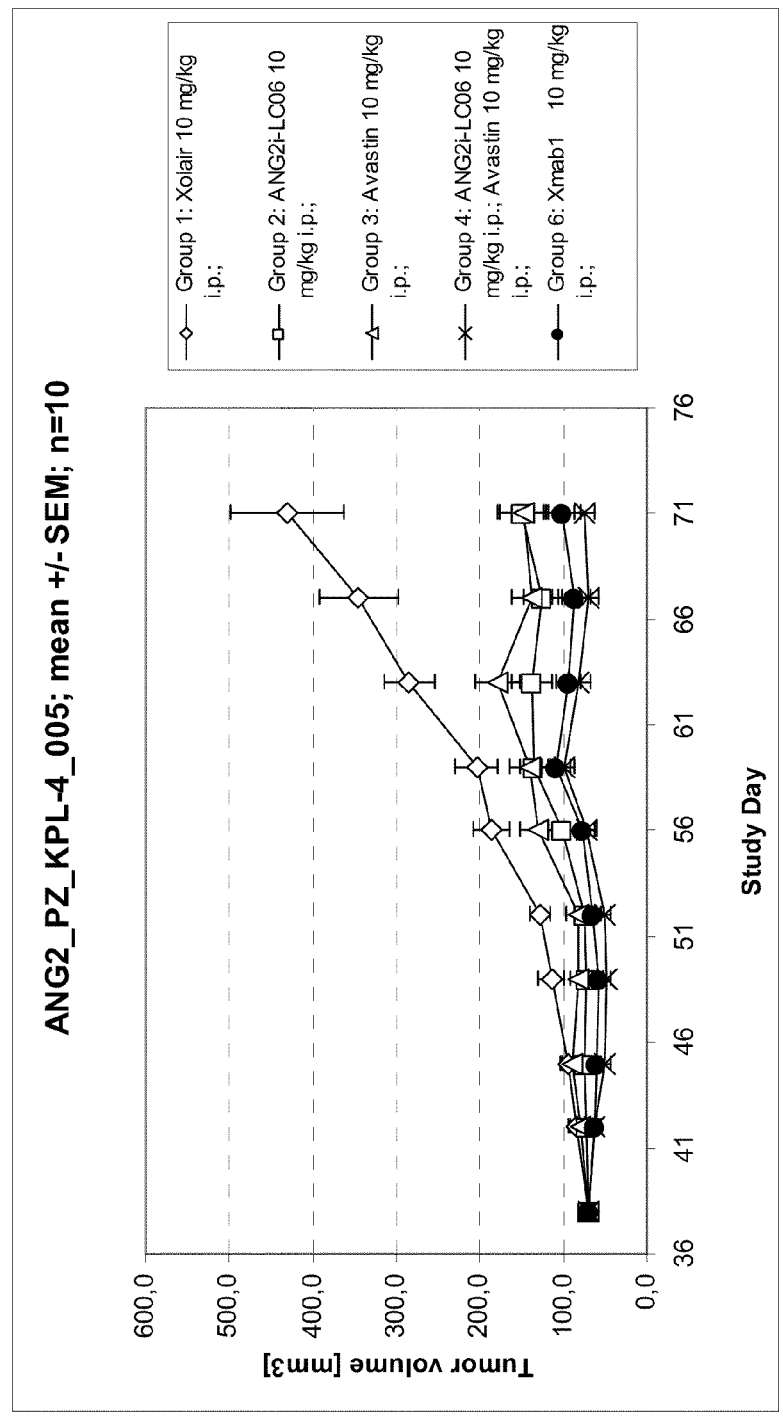
FIG. 10 In vivo tumor growth inhibition in mouse xenograft of human breast cancer KPL-4 (small tumors) by a bispecific antibody according to the invention—Comparison of the bispecific <Ang2/VEGF> antibody XMab1, the <Ang2> Mab ANG2i-LC06 (LC06), the <VEGF> Mab bevacizumab (Avastin) and the combination ANG2i-LC06 and <VEGF> Mab bevacizumab (Avastin).

The results (see FIG. 10) show that the bispecific bivalent <VEGF-ANG-2> antibody XMAb1 showed a higher tumor growth inhibition in xenograft tumor model Colo205 in Scid beige mice compared to the treatment with monospecific antibodies. The efficacy of the combination of ANG2i-LC06 and bevacizumab showed comparable results to the XMAb1. Maximal efficacy of XMAb1 was already reached with 10 mg/kg.

In a second experiment the effect of XMAb1 on bigger tumors was analyzed.

Treatment of Animals

Treatment of animals started at day of randomization at a mean tumor volume of ~160 mm3, respectively. Mice were treated once weekly i.p. with the different compounds as indicated in following table.

| No of animals | Compound | Dose (mg/kg) | Route/Mode of administration |
|---|---|---|---|
| 10 | Xolair | 10 | i.p. once weekly |
| 10 | <VEGF> Avastin | 10 | i.p. once weekly |
| 10 | <ANG-2> Ang2i-LC06 | 10 | i.p. once weekly |
| 10 | Ang2i-LC06 + Avastin | 10 10 | i.p. once weekly i.p. once weekly |
| 10 | XMAb1 | 10 | i.p. once weekly |

Monitoring:

Animals were controlled 2× per week for their health status. Body weights were documented 2× per week after cell injection. The tumor dimensions were measured by caliper on the staging day, at beginning of treatment period 2 times per week. Tumor volume was calculated according to NCI protocol (B. Teicher; Anticancer drug development guide, Humana Press, 1997, Chapter 5, page 92) (Tumor weight=½ ab², where "a" and "b" are the long and the short diameters of the tumor, respectively).

Termination criteria were the critical tumor mass (up to 1.7 g or Ø>1.5 cm), body weight loss more than 20% from baseline, tumor ulceration or poor general condition of the animals.

Figure 11:
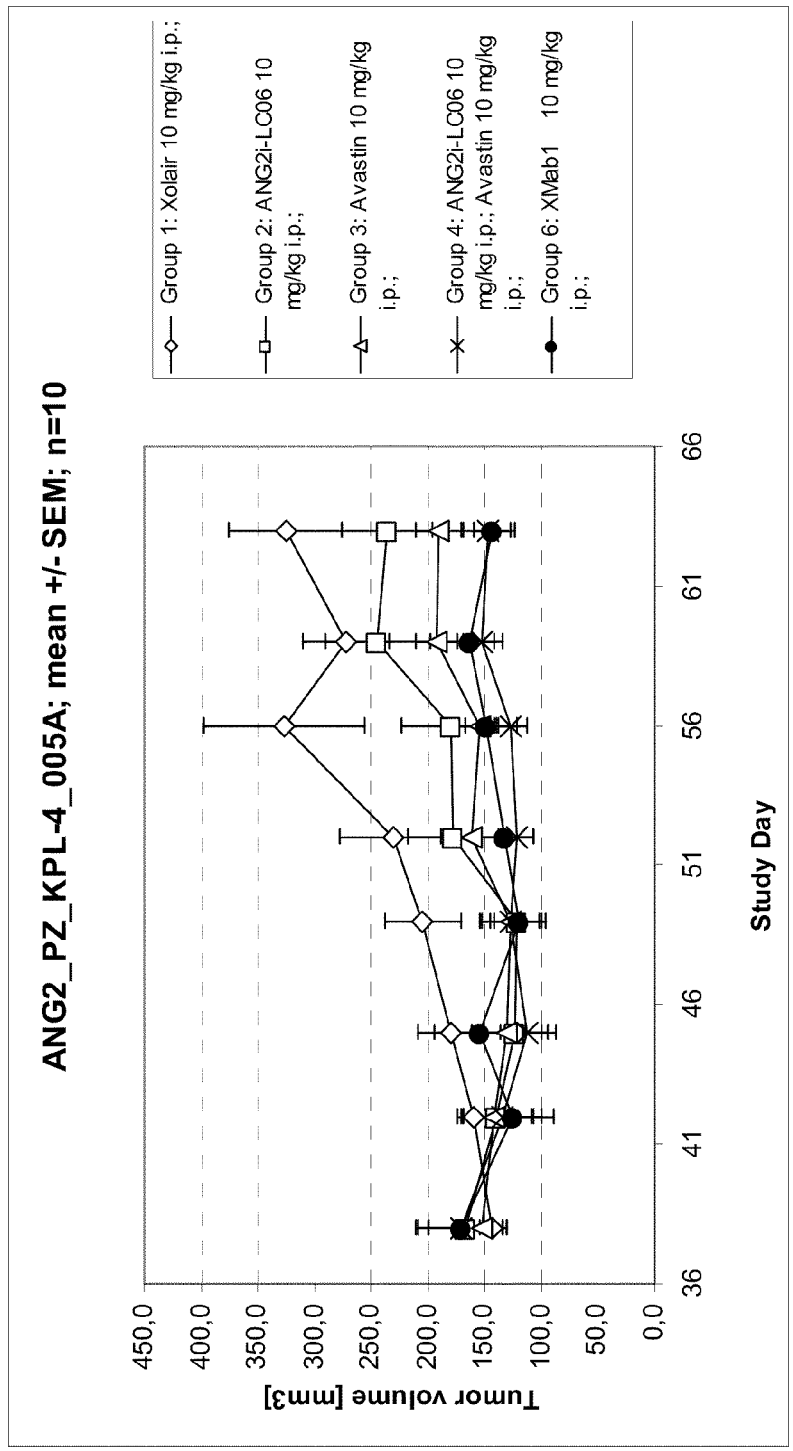
FIG. 11 In vivo tumor growth inhibition in mouse xenograft of human breast cancer KPL-4 (large tumors) by a bispecific antibody according to the invention—Comparison of the bispecific <Ang2/VEGF> antibody XMab1, the <Ang2> Mab ANG2i-LC06 (LC06), the <VEGF> Mab bevacizumab (Avastin) and the combination ANG2i-LC06 and <VEGF> Mab bevacizumab (Avastin).

The results (see FIG. 11) show that the bispecific bivalent <VEGF-ANG-2> antibody XMAb1 showed a higher tumor growth inhibition in xenograft tumor model Colo205 in Scid beige mice compared to the treatment with monospecific antibodies. The efficacy of the combination of ANG2i-LC06 and bevacizumab showed comparable results to the XMAb1. Maximal efficacy of XMAb1 was already reached with 10 mg/kg.

Taken together the results demonstrate that independent of the tumor size XMAb1 shows superior efficacy compared to the treatment with monospecific antibodies.

Tumor stasis in these models could be already achieved at lower concentrations of 10 mg/kg XMAb1 compared to the combination of 10 mg/kg of Ang21-LC06+10 mg/kg of Avastin.

Example 11

Effect of Treatment with XMAb1 on Micro-Vessel Density in s.c. Colo205 Xenograft Vascular density is assessed by counting all vessels of a tumor slide. Vessels were labeled with fluorescent anti-mouse CD34 antibody (clone MEC14.7) on paraffin-embedded sections. Vessels were quantified and microvessel density is calculated as vessels per mm². All results were expressed as mean±SEM. To define significant differences of experimental groups, Dunnetts-Method was used. p<0.05 was considered as statistically significant. The results show that total intratumoral MVD was decreased in treated tumors. Treatment with ANG2i-LC06 reduced MVD by 29%, bevacizumab by </=0%, bevacizumab+ANG2i-LC06 by 15% and XMAb1 by 28%.

Example 12

In vivo Efficacy of Bispecific Antibody <VEGF-ANG-2> Antibody in s.c. N87 Xenograft Model in Scid Beige Mice Tumor Cell Line The human gastric cancer cell line N87 cancer cells (NC1—N87 (ATCC No.CRL 5822)). Tumor cells were routinely cultured in RPMI1640 supplemented with 10% fetal bovine serum (PAN Biotech, Germany) and 2 mM L-glutamine (PAN Biotech, Germany) at 37° C. in a water-saturated atmosphere at 5% $CO_2$. Culture passage was performed with trypsin/EDTA 1× (PAN) splitting three times/week.

Mice

After arrival, female SCID beige mice (age 10-12 weeks; body weight 18-20 g) Charles River, Sulzfeld, Germany) were maintained in the quarantine part of the AALAAC approved animal facility for one week to get them accustomed to the new environment and for observation. Continuous health monitoring was carried out. The mice were kept under SPF-conditions according to the international guidelines (GV-Solas; Felasa; TierschG) with daily cycles of 12 h light/12 h darkness. Diet food (Kliba Provimi 3347) and water (filtered) were provided ad libitum. Experimental study protocol was reviewed and approved by the local government (Regierung von Oberbayern; registration no. 211.2531.2-22/2003).

Tumor Cell Injection

At the day of cell injection, cells were harvested from culture flasks (Greiner T 75), transferred into 50 ml culture medium, washed once and resuspended in PBS. After an additional washing with PBS the cell concentration was measured with a Vi-Cell™ (Cell Viability Analyzer, Beckman Coulter, Madison, Wis., U.S.A.). The tumor cell suspension (PBS) was mixed carefully (to reduce cell aggregation) and kept on ice. The cell suspension was filled into a 1.0 ml syringe. For injection, a needle size of 0.45×25 mm was used. To generate primary tumors, $5×10^6$ N87 tumor cells in a volume of 100 μl PBS were injected subcutaneously into the right flank of each mouse.

Treatment of Animals

Treatment of animals started at day of randomization at a mean tumor volume of ~130 mm3, respectively. Mice are treated once weekly i.p. with the different compounds as indicated in following table.

| No of animals | Compound | Dose (mg/kg) | Route/Mode of administration |
|---|---|---|---|
| 10 | Xolair | 10 | i.p. once weekly |
| 10 | <VEGF> Avastin | 10 | i.p. once weekly |
| 10 | <ANG-2> Ang2i-LC06 | 10 | i.p. once weekly |
| 10 | XMAb1 | 10 | i.p. once weekly |

Monitoring of Tumor Growth

Animals were controlled 1× per week for their health status. Body weights were documented 1× per week after cell injection. The tumor dimensions were measured by caliper on the staging day, at beginning of treatment period once per week. Tumor volume was calculated according to NCI protocol (B. Teicher; Anticancer drug development guide, Humana Press, 1997, Chapter 5, page 92) (Tumor weight=½ ab², where "a" and "b" are the long and the short diameters of the tumor, respectively).

Termination criteria were the critical tumor mass (up to 1.7 g or Ø>1.5 cm), body weight loss more than 20% from baseline, tumor ulceration or poor general condition of the animals.

Figure 12:
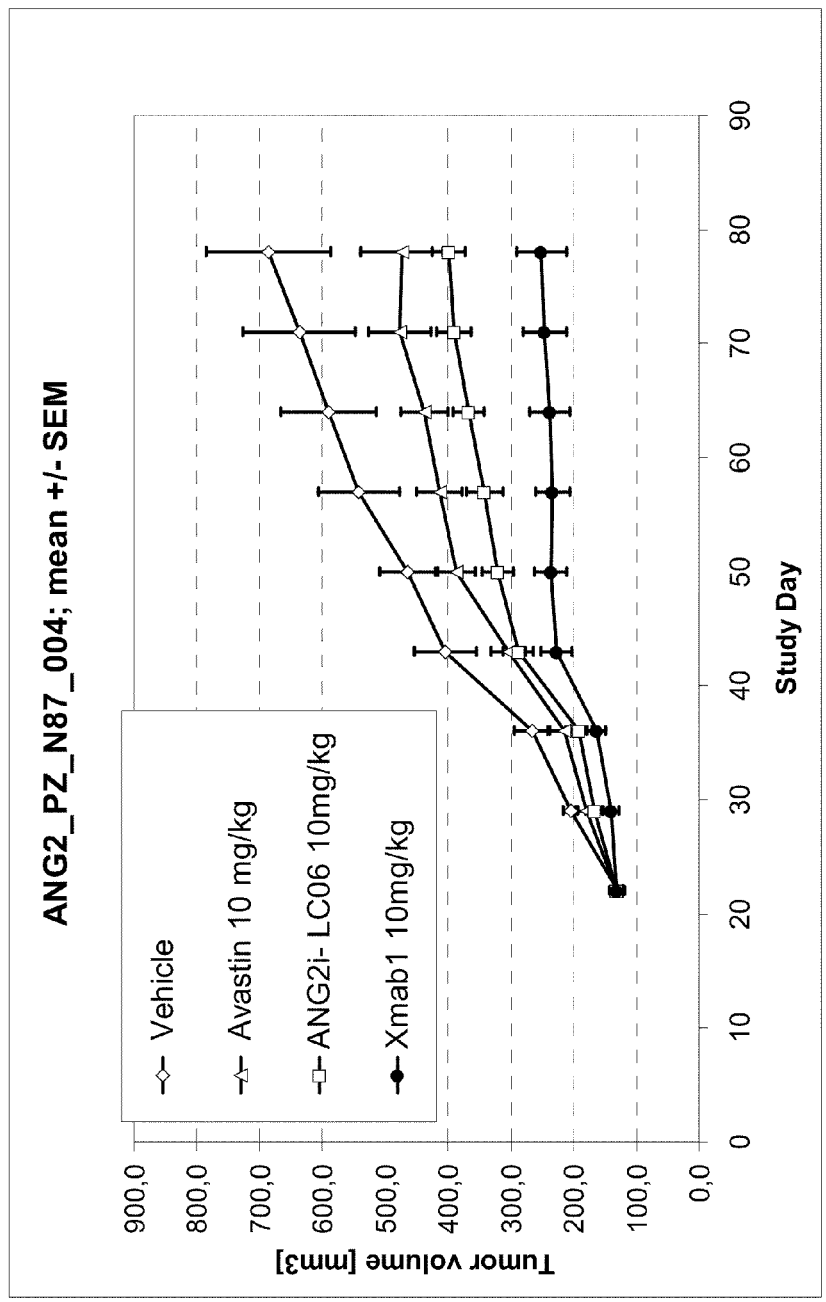
FIG. 12 In vivo tumor growth inhibition in mouse xenograft of gastric cancer N87 by a bispecific antibody according to the invention—Comparison of the bispecific <Ang2/VEGF> antibody XMab1, the <Ang2> Mab ANG2i-LC06 (LC06), the <VEGF> Mab bevacizumab (Avastin) and the combination ANG2i-LC06 and <VEGF> Mab bevacizumab (Avastin).

The results show that the bispecific bivalent <VEGF-ANG-2> antibody XMAb1 showed a higher tumor growth inhibition in xenograft tumor model Colo205 in Scid beige mice compared to the treatment with monospecific antibodies (FIG. 12).

The invention claimed is:

1. A purified bispecific, bivalent antibody comprising a first antigen-binding site that specifically binds to human VEGF and a second antigen-binding site that specifically binds to human ANG-2, wherein the antibody comprises the amino acid sequences of SEQ ID NO: 5, SEQ ID NO: 6, SEQ ID NO: 7, and SEQ ID NO: 8.

2. The purified bispecific antibody according to claim 1 for the treatment of colorectal cancer.

3. A pharmaceutical composition comprising the antibody of claim 1.

4. The bispecific antibody of claim 1, obtained by culturing a host cell comprising a nucleic acid encoding the bispecific antibody under conditions to express the bispecific antibody encoded by the nucleic acid; and then purifying the expressed bispecific antibody.

5. A purified bispecific, bivalent antibody comprising a first antigen-binding site that specifically binds to human VEGF and a second antigen-binding site that specifically binds to human ANG-2, wherein the antibody comprises the amino acid sequences of SEQ ID NO: 9, SEQ ID NO: 10, SEQ ID NO: 11, and SEQ ID NO: 12.

6. The purified bispecific antibody according to claim 5 for the treatment of colorectal cancer.

7. A pharmaceutical composition comprising the antibody of claim 5.

8. The bispecific antibody of claim 5, obtained by culturing a host cell comprising a nucleic acid encoding the bispecific antibody under conditions to express the bispecific antibody encoded by the nucleic acid; and then purifying the expressed bispecific antibody.

9. A purified bispecific, bivalent antibody comprising a first antigen-binding site that specifically binds to human VEGF and a second antigen-binding site that specifically binds to human ANG-2, wherein the antibody comprises the amino acid sequences of SEQ ID NO: 13, SEQ ID NO: 14, SEQ ID NO: 15, and SEQ ID NO: 16.

10. The purified bispecific antibody according to claim 9 for the treatment of colorectal cancer.

11. A pharmaceutical composition comprising the antibody of claim 9.

12. The bispecific antibody of claim 9, obtained by culturing a host cell comprising a nucleic acid encoding the bispecific antibody under conditions to express the bispecific antibody encoded by the nucleic acid; and then purifying the expressed bispecific antibody.

* * * * *

SEQUENCE LISTING

<160> NUMBER OF SEQ ID NOS: 49

<210> SEQ ID NO 1
<211> LENGTH: 123
<212> TYPE: PRT
<213> ORGANISM: Artificial
<220> FEATURE:
<223> OTHER INFORMATION: variable heavy chain domain VH of <VEGF>
      bevacizumab

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 2
<211> LENGTH: 107
<212> TYPE: PRT
<213> ORGANISM: Artificial
<220> FEATURE:
<223> OTHER INFORMATION: variable light chain domain VL of <VEGF>
      bevacizumab

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
            35                  40                  45

-continued

```
Tyr Phe Thr Ser Ser Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys
                100                 105

<210> SEQ ID NO 3
<211> LENGTH: 128
<212> TYPE: PRT
<213> ORGANISM: Artificial
<220> FEATURE:
<223> OTHER INFORMATION: variable heavy chain domain VH of <ANG-2> E6Q

<400> SEQUENCE: 3

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
                 20                  25                  30

Tyr Met His Trp Val Arg Gln Ala Pro Gly Gln Gly Leu Glu Trp Met
             35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Ser Pro Asn Pro Tyr Tyr Tyr Asp Ser Ser Gly Tyr Tyr Tyr
                100                 105                 110

Pro Gly Ala Phe Asp Ile Trp Gly Gln Gly Thr Met Val Thr Val Ser
            115                 120                 125

<210> SEQ ID NO 4
<211> LENGTH: 108
<212> TYPE: PRT
<213> ORGANISM: Artificial
<220> FEATURE:
<223> OTHER INFORMATION: variable light chain domain VL of < ANG-2> E6Q

<400> SEQUENCE: 4

Gln Pro Gly Leu Thr Gln Pro Pro Ser Val Ser Val Ala Pro Gly Gln
 1               5                  10                  15

Thr Ala Arg Ile Thr Cys Gly Gly Asn Asn Ile Gly Ser Lys Ser Val
                 20                  25                  30

His Trp Tyr Gln Gln Lys Pro Gly Gln Ala Pro Val Leu Val Val Tyr
             35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Tyr Val Phe Gly Thr Gly Thr Lys Val Thr Val Leu
                100                 105

<210> SEQ ID NO 5
```

```
<211> LENGTH: 214
<212> TYPE: PRT
<213> ORGANISM: Artificial
<220> FEATURE:
<223> OTHER INFORMATION: XMab1 -<VEGF> light chain

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 6
<211> LENGTH: 213
<212> TYPE: PRT
<213> ORGANISM: Artificial
<220> FEATURE:
<223> OTHER INFORMATION: XMab1 -<ANG2> light chain

<400> SEQUENCE: 6

Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu Ser Ser Ala Ser
```

```
                 100                 105                 110
Thr Lys Gly Pro Ser Val Phe Pro Leu Ala Pro Ser Ser Lys Ser Thr
                115                 120                 125
Ser Gly Gly Thr Ala Ala Leu Gly Cys Leu Val Lys Asp Tyr Phe Pro
            130                 135                 140
Glu Pro Val Thr Val Ser Trp Asn Ser Gly Ala Leu Thr Ser Gly Val
145                 150                 155                 160
His Thr Phe Pro Ala Val Leu Gln Ser Ser Gly Leu Tyr Ser Leu Ser
                165                 170                 175
Ser Val Val Thr Val Pro Ser Ser Leu Gly Thr Gln Thr Tyr Ile
            180                 185                 190
Cys Asn Val Asn His Lys Pro Ser Asn Thr Lys Val Asp Lys Lys Val
                195                 200                 205
Glu Pro Lys Ser Cys
            210

<210> SEQ ID NO 7
<211> LENGTH: 453
<212> TYPE: PRT
<213> ORGANISM: Artificial
<220> FEATURE:
<223> OTHER INFORMATION: XMab1 -<VEGF> heavy chain

<400> SEQUENCE: 7

Glu Val Gln Leu Val Glu Ser Gly Gly Gly Leu Val Gln Pro Gly Gly
1               5                   10                  15
Ser Leu Arg Leu Ser Cys Ala Ala Ser Gly Tyr Thr Phe Thr Asn Tyr
                20                  25                  30
Gly Met Asn Trp Val Arg Gln Ala Pro Gly Lys Gly Leu Glu Trp Val
            35                  40                  45
Gly Trp Ile Asn Thr Tyr Thr Gly Glu Pro Thr Tyr Ala Ala Asp Phe
        50                  55                  60
Lys Arg Arg Phe Thr Phe Ser Leu Asp Thr Ser Lys Ser Thr Ala Tyr
65                  70                  75                  80
Leu Gln Met Asn Ser Leu Arg Ala Glu Asp Thr Ala Val Tyr Tyr Cys
                85                  90                  95
Ala Lys Tyr Pro His Tyr Tyr Gly Ser Ser His Trp Tyr Phe Asp Val
                100                 105                 110
Trp Gly Gln Gly Thr Leu Val Thr Val Ser Ser Ala Ser Thr Lys Gly
                115                 120                 125
Pro Ser Val Phe Pro Leu Ala Pro Ser Ser Lys Ser Thr Ser Gly Gly
            130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
                195                 200                 205
Asn His Lys Pro Ser Asn Thr Lys Val Asp Lys Lys Val Glu Pro Lys
            210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
```

```
                    245                 250                 255
Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Cys Arg Asp Glu Leu Thr Lys Asn Gln
            355                 360                 365

Val Ser Leu Trp Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
            450

<210> SEQ ID NO 8
<211> LENGTH: 463
<212> TYPE: PRT
<213> ORGANISM: Artificial
<220> FEATURE:
<223> OTHER INFORMATION: XMab1 -<ANG2> heavy chain

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
            115                 120                 125

Ser Ala Ser Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
```

```
                145                 150                 155                 160
        Phe Tyr Pro Arg Glu Ala Lys Val Gln Trp Lys Val Asp Asn Ala Leu
                        165                 170                 175
        Gln Ser Gly Asn Ser Gln Glu Ser Val Thr Glu Gln Asp Ser Lys Asp
                        180                 185                 190
        Ser Thr Tyr Ser Leu Ser Ser Thr Leu Thr Leu Ser Lys Ala Asp Tyr
                        195                 200                 205
        Glu Lys His Lys Val Tyr Ala Cys Glu Val Thr His Gln Gly Leu Ser
                        210                 215                 220
        Ser Pro Val Thr Lys Ser Phe Asn Arg Gly Glu Cys Asp Lys Thr His
        225                 230                 235                 240
        Thr Cys Pro Pro Cys Pro Ala Pro Glu Leu Leu Gly Gly Pro Ser Val
                        245                 250                 255
        Phe Leu Phe Pro Pro Lys Pro Lys Asp Thr Leu Met Ile Ser Arg Thr
                        260                 265                 270
        Pro Glu Val Thr Cys Val Val Val Asp Val Ser His Glu Asp Pro Glu
                        275                 280                 285
        Val Lys Phe Asn Trp Tyr Val Asp Gly Val Glu Val His Asn Ala Lys
                        290                 295                 300
        Thr Lys Pro Arg Glu Glu Gln Tyr Asn Ser Thr Tyr Arg Val Val Ser
        305                 310                 315                 320
        Val Leu Thr Val Leu His Gln Asp Trp Leu Asn Gly Lys Glu Tyr Lys
                        325                 330                 335
        Cys Lys Val Ser Asn Lys Ala Leu Pro Ala Pro Ile Glu Lys Thr Ile
                        340                 345                 350
        Ser Lys Ala Lys Gly Gln Pro Arg Glu Pro Gln Val Cys Thr Leu Pro
                        355                 360                 365
        Pro Ser Arg Asp Glu Leu Thr Lys Asn Gln Val Ser Leu Ser Cys Ala
                        370                 375                 380
        Val Lys Gly Phe Tyr Pro Ser Asp Ile Ala Val Glu Trp Glu Ser Asn
        385                 390                 395                 400
        Gly Gln Pro Glu Asn Asn Tyr Lys Thr Thr Pro Pro Val Leu Asp Ser
                        405                 410                 415
        Asp Gly Ser Phe Phe Leu Val Ser Lys Leu Thr Val Asp Lys Ser Arg
                        420                 425                 430
        Trp Gln Gln Gly Asn Val Phe Ser Cys Ser Val Met His Glu Ala Leu
                        435                 440                 445
        His Asn His Tyr Thr Gln Lys Ser Leu Ser Leu Ser Pro Gly Lys
            450                 455                 460

<210> SEQ ID NO 9
<211> LENGTH: 214
<212> TYPE: PRT
<213> ORGANISM: Artificial
<220> FEATURE:
<223> OTHER INFORMATION: XMab2 -<VEGF> light chain

<400> SEQUENCE: 9

Asp Ile Gln Met Thr Gln Ser Pro Ser Ser Leu Ser Ala Ser Val Gly
1               5                   10                  15
Asp Arg Val Thr Ile Thr Cys Ser Ala Ser Gln Asp Ile Ser Asn Tyr
                20                  25                  30
Leu Asn Trp Tyr Gln Gln Lys Pro Gly Lys Ala Pro Lys Val Leu Ile
            35                  40                  45
Tyr Phe Thr Ser Ser Leu His Ser Gly Val Pro Ser Arg Phe Ser Gly
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 10
<211> LENGTH: 212
<212> TYPE: PRT
<213> ORGANISM: Artificial
<220> FEATURE:
<223> OTHER INFORMATION: XMab2 -<VEGF> heavy chain

<400> SEQUENCE: 10

Gln Pro Gly Leu Thr Gln Pro Pro Ser Val Ser Val Ala Pro Gly Gln
  1               5                  10                  15

Thr Ala Arg Ile Thr Cys Gly Gly Asn Asn Ile Gly Ser Lys Ser Val
             20                  25                  30

His Trp Tyr Gln Gln Lys Pro Gly Gln Ala Pro Val Leu Val Val Tyr
         35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Tyr Val Phe Gly Thr Gly Thr Lys Val Thr Val Leu Gly Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
```

Pro Lys Ser Cys
    210

<210> SEQ ID NO 11
<211> LENGTH: 453
<212> TYPE: PRT
<213> ORGANISM: Artificial
<220> FEATURE:
<223> OTHER INFORMATION: XMab2 -<VEGF> heavy chain

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro

```
                340             345             350
Gln Val Tyr Thr Leu Pro Pro Cys Arg Asp Glu Leu Thr Lys Asn Gln
            355             360             365

Val Ser Leu Trp Cys Leu Val Lys Gly Phe Tyr Pro Ser Asp Ile Ala
        370             375             380

Val Glu Trp Glu Ser Asn Gly Gln Pro Glu Asn Asn Tyr Lys Thr Thr
385             390             395             400

Pro Pro Val Leu Asp Ser Asp Gly Ser Phe Phe Leu Tyr Ser Lys Leu
            405             410             415

Thr Val Asp Lys Ser Arg Trp Gln Gln Gly Asn Val Phe Ser Cys Ser
            420             425             430

Val Met His Glu Ala Leu His Asn His Tyr Thr Gln Lys Ser Leu Ser
            435             440             445

Leu Ser Pro Gly Lys
    450

<210> SEQ ID NO 12
<211> LENGTH: 461
<212> TYPE: PRT
<213> ORGANISM: Artificial
<220> FEATURE:
<223> OTHER INFORMATION: XMab2 -<ANG2> heavy chain

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
            165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser Asp Lys Thr His Thr Cys
225                 230                 235                 240

Pro Pro Cys Pro Ala Pro Glu Leu Leu Gly Gly Pro Ser Val Phe Leu
```

```
            245                 250                 255
Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
            275                 280                 285

Phe Asn Trp Tyr Val Asp Gly Val Glu Val His Asn Ala Lys Thr Lys
            290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Cys Thr Leu Pro Pro Ser
            355                 360                 365

Arg Asp Glu Leu Thr Lys Asn Gln Val Ser Leu Ser Cys Ala Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Val Ser Lys Leu Thr Val Asp Lys Ser Arg Trp Gln
            420                 425                 430

Gln Gly Asn Val Phe Ser Cys Ser Val Met His Glu Ala Leu His Asn
            435                 440                 445

His Tyr Thr Gln Lys Ser Leu Ser Leu Ser Pro Gly Lys
450                 455                 460

<210> SEQ ID NO 13
<211> LENGTH: 214
<212> TYPE: PRT
<213> ORGANISM: Artificial
<220> FEATURE:
<223> OTHER INFORMATION: XMab3 -<VEGF> light chain

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

```
                145                 150                 155                 160
Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                    180                 185                 190

Ala Cys Glu Val Thr His Gln Gly Leu Ser Ser Pro Val Thr Lys Ser
                    195                 200                 205

Phe Asn Arg Gly Glu Cys
                210

<210> SEQ ID NO 14
<211> LENGTH: 213
<212> TYPE: PRT
<213> ORGANISM: Artificial
<220> FEATURE:
<223> OTHER INFORMATION: XMab3-<ANG2> light chain

<400> SEQUENCE: 14

Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu Ser Ser Ala Ser
                100                 105                 110

Thr Lys Gly Pro Ser Val Phe Pro Leu Ala Pro Ser Ser Lys Ser Thr
            115                 120                 125

Ser Gly Gly Thr Ala Ala Leu Gly Cys Leu Val Lys Asp Tyr Phe Pro
130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
                180                 185                 190

Cys Asn Val Asn His Lys Pro Ser Asn Thr Lys Val Asp Lys Lys Val
            195                 200                 205

Glu Pro Lys Ser Cys
            210

<210> SEQ ID NO 15
<211> LENGTH: 453
<212> TYPE: PRT
<213> ORGANISM: Artificial
<220> FEATURE:
<223> OTHER INFORMATION: XMab3 -<VEGF> heavy chain

<400> SEQUENCE: 15

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Tyr Thr Phe Thr Asn Tyr
        20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
        50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Cys Thr Leu Pro Pro Ser Arg Asp Glu Leu Thr Lys Asn Gln
        355                 360                 365

Val Ser Leu Ser Cys Ala Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Val Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
```

-continued

```
              435                 440                 445
Leu Ser Pro Gly Lys
    450

<210> SEQ ID NO 16
<211> LENGTH: 463
<212> TYPE: PRT
<213> ORGANISM: Artificial
<220> FEATURE:
<223> OTHER INFORMATION: XMab3 -<ANG2> heavy chain

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
```

```
                  340                 345                 350
Ser Lys Ala Lys Gly Gln Pro Arg Glu Pro Gln Val Tyr Thr Leu Pro
            355                 360                 365

Pro Cys Arg Asp Glu Leu Thr Lys Asn Gln Val Ser Leu Trp Cys Leu
        370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460

<210> SEQ ID NO 17
<211> LENGTH: 214
<212> TYPE: PRT
<213> ORGANISM: Artificial
<220> FEATURE:
<223> OTHER INFORMATION: XMab4 -<VEGF> light chain

<400> SEQUENCE: 17

Asp Ile Gln Met Thr Gln Ser Pro Ser Ser Leu Ser Ala Ser Val Gly
1               5                  10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 18
<211> LENGTH: 212
<212> TYPE: PRT
```

<213> ORGANISM: Artificial
<220> FEATURE:
<223> OTHER INFORMATION: XMab4-<ANG2> light chain

<400> SEQUENCE: 18

```
Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65              70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu Gly Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145             150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205

Pro Lys Ser Cys
    210
```

<210> SEQ ID NO 19
<211> LENGTH: 453
<212> TYPE: PRT
<213> ORGANISM: Artificial
<220> FEATURE:
<223> OTHER INFORMATION: XMab4 -<VEGF> heavy chain

<400> SEQUENCE: 19

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65              70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110
```

```
Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Cys Thr Leu Pro Pro Ser Arg Asp Glu Leu Thr Lys Asn Gln
        355                 360                 365

Val Ser Leu Ser Cys Ala Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Val Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 20
<211> LENGTH: 461
<212> TYPE: PRT
<213> ORGANISM: Artificial
<220> FEATURE:
<223> OTHER INFORMATION: XMab4 -<ANG2> heavy chain

<400> SEQUENCE: 20

Gln Val Gln Leu Val Gln Ser Gly Ala Glu Val Lys Lys Pro Gly Ala
1               5                   10                  15
```

-continued

Ser Val Lys Val Ser Cys Lys Ala Ser Gly Tyr Thr Phe Thr Gly Tyr
        20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser Asp Lys Thr His Thr Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Cys
        355                 360                 365

Arg Asp Glu Leu Thr Lys Asn Gln Val Ser Leu Trp Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn

His Tyr Thr Gln Lys Ser Leu Ser Leu Ser Pro Gly Lys
    450                 455                 460

<210> SEQ ID NO 21
<211> LENGTH: 214
<212> TYPE: PRT
<213> ORGANISM: Artificial
<220> FEATURE:
<223> OTHER INFORMATION: XMab5 -<VEGF> light chain

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 22
<211> LENGTH: 212
<212> TYPE: PRT
<213> ORGANISM: Artificial
<220> FEATURE:
<223> OTHER INFORMATION: XMab5 -<ANG2> light chain

<400> SEQUENCE: 22

Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

```
Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Tyr Val Phe Gly Gln Gly Thr Leu Val Thr Val Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205

Pro Lys Ser Cys
    210

<210> SEQ ID NO 23
<211> LENGTH: 453
<212> TYPE: PRT
<213> ORGANISM: Artificial
<220> FEATURE:
<223> OTHER INFORMATION: XMab5 -<VEGF> heavy chain

<400> SEQUENCE: 23

Glu Val Gln Leu Val Glu Ser Gly Gly Gly Leu Val Gln Pro Gly Gly
  1               5                  10                  15

Ser Leu Arg Leu Ser Cys Ala Ala Ser Gly Tyr Thr Phe Thr Asn Tyr
             20                  25                  30

Gly Met Asn Trp Val Arg Gln Ala Pro Gly Lys Gly Leu Glu Trp Val
         35                  40                  45

Gly Trp Ile Asn Thr Tyr Thr Gly Glu Pro Thr Tyr Ala Ala Asp Phe
     50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205
```

```
Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
        260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
        340                 345                 350

Gln Val Tyr Thr Leu Pro Pro Cys Arg Asp Glu Leu Thr Lys Asn Gln
            355                 360                 365

Val Ser Leu Trp Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
        420                 425                 430

Val Met His Glu Ala Leu His Asn His Tyr Thr Gln Lys Ser Leu Ser
            435                 440                 445

Leu Ser Pro Gly Lys
        450

<210> SEQ ID NO 24
<211> LENGTH: 461
<212> TYPE: PRT
<213> ORGANISM: Artificial
<220> FEATURE:
<223> OTHER INFORMATION: XMab5 -<ANG2> heavy chain

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
                100                 105                 110
```

```
Pro Gly Ala Phe Asp Ile Trp Gly Gly Thr Lys Val Thr Val Leu
            115                 120                 125

Gly Gln Pro Lys Ala Ala Pro Ser Val Thr Leu Phe Pro Pro Ser Ser
130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Pro Ser Lys Gln Ser Asn Asn
                180                 185                 190

Lys Tyr Ala Ala Ser Ser Tyr Leu Ser Leu Thr Pro Glu Gln Trp Lys
            195                 200                 205

Ser His Arg Ser Tyr Ser Cys Gln Val Thr His Glu Gly Ser Thr Val
210                 215                 220

Glu Lys Thr Val Ala Pro Thr Glu Cys Ser Asp Lys Thr His Thr Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
                260                 265                 270

Val Thr Cys Val Val Val Asp Val Ser His Glu Asp Pro Glu Val Lys
            275                 280                 285

Phe Asn Trp Tyr Val Asp Gly Val Glu Val His Asn Ala Lys Thr Lys
            290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
                340                 345                 350

Ala Lys Gly Gln Pro Arg Glu Pro Gln Val Cys Thr Leu Pro Pro Ser
            355                 360                 365

Arg Asp Glu Leu Thr Lys Asn Gln Val Ser Leu Ser Cys Ala Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Val Ser Lys Leu Thr Val Asp Lys Ser Arg Trp Gln
                420                 425                 430

Gln Gly Asn Val Phe Ser Cys Ser Val Met His Glu Ala Leu His Asn
            435                 440                 445

His Tyr Thr Gln Lys Ser Leu Ser Leu Ser Pro Gly Lys
            450                 455                 460

<210> SEQ ID NO 25
<211> LENGTH: 214
<212> TYPE: PRT
<213> ORGANISM: Artificial
<220> FEATURE:
<223> OTHER INFORMATION: XMab6 -<VEGF> light chain

<400> SEQUENCE: 25

Asp Ile Gln Met Thr Gln Ser Pro Ser Ser Leu Ser Ala Ser Val Gly
1               5                   10                  15
```

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 26
<211> LENGTH: 212
<212> TYPE: PRT
<213> ORGANISM: Artificial
<220> FEATURE:
<223> OTHER INFORMATION: XMab6 -<ANG2> light chain

<400> SEQUENCE: 26

Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Gln Gly Thr Leu Val Thr Val Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

```
Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205

Pro Lys Ser Cys
    210

<210> SEQ ID NO 27
<211> LENGTH: 453
<212> TYPE: PRT
<213> ORGANISM: Artificial
<220> FEATURE:
<223> OTHER INFORMATION: XMab6 -<VEGF> heavy chain

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300
```

```
Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Cys Thr Leu Pro Pro Ser Arg Asp Glu Leu Thr Lys Asn Gln
            355                 360                 365

Val Ser Leu Ser Cys Ala Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Val Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
            450

<210> SEQ ID NO 28
<211> LENGTH: 461
<212> TYPE: PRT
<213> ORGANISM: Artificial
<220> FEATURE:
<223> OTHER INFORMATION: XMab6 -<ANG2> heavy chain

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Asp Ser Ser Gly Tyr Tyr Tyr
            100                 105                 110

Pro Gly Ala Phe Asp Ile Trp Gly Gly Gly Thr Lys Val Thr Val Leu
        115                 120                 125

Gly Gln Pro Lys Ala Ala Pro Ser Val Thr Leu Phe Pro Pro Ser Ser
130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205
```

```
Ser His Arg Ser Tyr Ser Cys Gln Val Thr His Glu Gly Ser Thr Val
    210                 215                 220

Glu Lys Thr Val Ala Pro Thr Glu Cys Ser Asp Lys Thr His Thr Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Cys
        355                 360                 365

Arg Asp Glu Leu Thr Lys Asn Gln Val Ser Leu Trp Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460

<210> SEQ ID NO 29
<211> LENGTH: 706
<212> TYPE: PRT
<213> ORGANISM: Artificial
<220> FEATURE:
<223> OTHER INFORMATION: OAscFab1 -<ANG2> peptide connected heavy chain
      and light chain

<400> SEQUENCE: 29

Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu Arg Thr Val Ala
            100                 105                 110
```

```
Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys Gly Gly Gly Gly Ser Gly Gly Gly Gly
            210                 215                 220

Ser Gly Gly Gly Gly Ser Gly Gly Gly Gly Ser Gly Gly Gly Gly Ser
225                 230                 235                 240

Gly Gly Gly Gly Ser Gly Gly Gln Val Gln Leu Val Gln Ser Gly Ala
            245                 250                 255

Glu Val Lys Lys Pro Gly Ala Ser Val Lys Val Ser Cys Lys Ala Ser
            260                 265                 270

Gly Tyr Thr Phe Thr Gly Tyr Tyr Met His Trp Val Arg Gln Ala Pro
            275                 280                 285

Gly Gln Gly Leu Glu Trp Met Gly Trp Ile Asn Pro Asn Ser Gly Gly
            290                 295                 300

Thr Asn Tyr Ala Gln Lys Phe Gln Gly Arg Val Thr Met Thr Arg Asp
305                 310                 315                 320

Thr Ser Ile Ser Thr Ala Tyr Met Glu Leu Ser Arg Leu Arg Ser Asp
            325                 330                 335

Asp Thr Ala Val Tyr Tyr Cys Ala Arg Ser Pro Asn Pro Tyr Tyr Tyr
            340                 345                 350

Asp Ser Ser Gly Tyr Tyr Pro Gly Ala Phe Asp Ile Trp Gly Gln
            355                 360                 365

Gly Thr Met Val Thr Val Ser Ser Ala Ser Thr Lys Gly Pro Ser Val
            370                 375                 380

Phe Pro Leu Ala Pro Ser Ser Lys Ser Thr Ser Gly Gly Thr Ala Ala
385                 390                 395                 400

Leu Gly Cys Leu Val Lys Asp Tyr Phe Pro Glu Pro Val Thr Val Ser
            405                 410                 415

Trp Asn Ser Gly Ala Leu Thr Ser Gly Val His Thr Phe Pro Ala Val
            420                 425                 430

Leu Gln Ser Ser Gly Leu Tyr Ser Leu Ser Ser Val Val Thr Val Pro
            435                 440                 445

Ser Ser Ser Leu Gly Thr Gln Thr Tyr Ile Cys Asn Val Asn His Lys
450                 455                 460

Pro Ser Asn Thr Lys Val Asp Lys Lys Val Glu Pro Lys Ser Cys Asp
465                 470                 475                 480

Lys Thr His Thr Cys Pro Pro Cys Pro Ala Pro Glu Leu Leu Gly Gly
            485                 490                 495

Pro Ser Val Phe Leu Phe Pro Pro Lys Pro Lys Asp Thr Leu Met Ile
            500                 505                 510

Ser Arg Thr Pro Glu Val Thr Cys Val Val Val Asp Val Ser His Glu
            515                 520                 525
```

```
Asp Pro Glu Val Lys Phe Asn Trp Tyr Val Asp Gly Val Glu Val His
    530                 535                 540

Asn Ala Lys Thr Lys Pro Arg Glu Glu Gln Tyr Asn Ser Thr Tyr Arg
545                 550                 555                 560

Val Val Ser Val Leu Thr Val Leu His Gln Asp Trp Leu Asn Gly Lys
                565                 570                 575

Glu Tyr Lys Cys Lys Val Ser Asn Lys Ala Leu Pro Ala Pro Ile Glu
            580                 585                 590

Lys Thr Ile Ser Lys Ala Lys Gly Gln Pro Arg Glu Pro Gln Val Tyr
        595                 600                 605

Thr Leu Pro Pro Cys Arg Asp Glu Leu Thr Lys Asn Gln Val Ser Leu
610                 615                 620

Trp Cys Leu Val Lys Gly Phe Tyr Pro Ser Asp Ile Ala Val Glu Trp
625                 630                 635                 640

Glu Ser Asn Gly Gln Pro Glu Asn Asn Tyr Lys Thr Thr Pro Pro Val
                645                 650                 655

Leu Asp Ser Asp Gly Ser Phe Phe Leu Tyr Ser Lys Leu Thr Val Asp
            660                 665                 670

Lys Ser Arg Trp Gln Gln Gly Asn Val Phe Ser Cys Ser Val Met His
        675                 680                 685

Glu Ala Leu His Asn His Tyr Thr Gln Lys Ser Leu Ser Leu Ser Pro
690                 695                 700

Gly Lys
705

<210> SEQ ID NO 30
<211> LENGTH: 453
<212> TYPE: PRT
<213> ORGANISM: Artificial
<220> FEATURE:
<223> OTHER INFORMATION: OAscFab1 -<VEGF> heavy chain

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175
```

```
Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Cys Thr Leu Pro Pro Ser Arg Asp Glu Leu Thr Lys Asn Gln
        355                 360                 365

Val Ser Leu Ser Cys Ala Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Val Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 31
<211> LENGTH: 214
<212> TYPE: PRT
<213> ORGANISM: Artificial
<220> FEATURE:
<223> OTHER INFORMATION: OAscFab1 -<VEGF> light chain

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 32
<211> LENGTH: 705
<212> TYPE: PRT
<213> ORGANISM: Artificial
<220> FEATURE:
<223> OTHER INFORMATION: OAscFab2 -<ANG2> peptide connected heavy chain
      and light chain

<400> SEQUENCE: 32

Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu Gly Gln Pro Lys
            100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
            130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
            165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser Gly Gly Gly Ser Gly Gly Gly Gly Ser
            210                 215                 220

```
Gly Gly Gly Gly Ser Gly Gly Gly Ser Gly Gly Gly Ser Gly
225                 230                 235                 240

Gly Gly Gly Ser Gly Gly Gln Val Gln Leu Val Gln Ser Gly Ala Glu
            245                 250                 255

Val Lys Lys Pro Gly Ala Ser Val Lys Val Ser Cys Lys Ala Ser Gly
260                 265                 270

Tyr Thr Phe Thr Gly Tyr Tyr Met His Trp Val Arg Gln Ala Pro Gly
        275                 280                 285

Gln Gly Leu Glu Trp Met Gly Trp Ile Asn Pro Asn Ser Gly Gly Thr
    290                 295                 300

Asn Tyr Ala Gln Lys Phe Gln Gly Arg Val Thr Met Thr Arg Asp Thr
305                 310                 315                 320

Ser Ile Ser Thr Ala Tyr Met Glu Leu Ser Arg Leu Arg Ser Asp Asp
                325                 330                 335

Thr Ala Val Tyr Tyr Cys Ala Arg Ser Pro Asn Pro Tyr Tyr Tyr Asp
            340                 345                 350

Ser Ser Gly Tyr Tyr Pro Gly Ala Phe Asp Ile Trp Gly Gln Gly
        355                 360                 365

Thr Met Val Thr Val Ser Ser Ala Ser Thr Lys Gly Pro Ser Val Phe
370                 375                 380

Pro Leu Ala Pro Ser Ser Lys Ser Thr Ser Gly Gly Thr Ala Ala Leu
385                 390                 395                 400

Gly Cys Leu Val Lys Asp Tyr Phe Pro Glu Pro Val Thr Val Ser Trp
                405                 410                 415

Asn Ser Gly Ala Leu Thr Ser Gly Val His Thr Phe Pro Ala Val Leu
            420                 425                 430

Gln Ser Ser Gly Leu Tyr Ser Leu Ser Ser Val Val Thr Val Pro Ser
        435                 440                 445

Ser Ser Leu Gly Thr Gln Thr Tyr Ile Cys Asn Val Asn His Lys Pro
450                 455                 460

Ser Asn Thr Lys Val Asp Lys Lys Val Glu Pro Lys Ser Cys Asp Lys
465                 470                 475                 480

Thr His Thr Cys Pro Pro Cys Pro Ala Pro Glu Leu Leu Gly Gly Pro
                485                 490                 495

Ser Val Phe Leu Phe Pro Pro Lys Pro Lys Asp Thr Leu Met Ile Ser
            500                 505                 510

Arg Thr Pro Glu Val Thr Cys Val Val Val Asp Val Ser His Glu Asp
        515                 520                 525

Pro Glu Val Lys Phe Asn Trp Tyr Val Asp Gly Val Glu Val His Asn
    530                 535                 540

Ala Lys Thr Lys Pro Arg Glu Glu Gln Tyr Asn Ser Thr Tyr Arg Val
545                 550                 555                 560

Val Ser Val Leu Thr Val Leu His Gln Asp Trp Leu Asn Gly Lys Glu
                565                 570                 575

Tyr Lys Cys Lys Val Ser Asn Lys Ala Leu Pro Ala Pro Ile Glu Lys
            580                 585                 590

Thr Ile Ser Lys Ala Lys Gly Gln Pro Arg Glu Pro Gln Val Tyr Thr
        595                 600                 605

Leu Pro Pro Cys Arg Asp Glu Leu Thr Lys Asn Gln Val Ser Leu Trp
    610                 615                 620

Cys Leu Val Lys Gly Phe Tyr Pro Ser Asp Ile Ala Val Glu Trp Glu
625                 630                 635                 640
```

```
Ser Asn Gly Gln Pro Glu Asn Asn Tyr Lys Thr Thr Pro Pro Val Leu
                645                 650                 655

Asp Ser Asp Gly Ser Phe Phe Leu Tyr Ser Lys Leu Thr Val Asp Lys
            660                 665                 670

Ser Arg Trp Gln Gln Gly Asn Val Phe Ser Cys Ser Val Met His Glu
        675                 680                 685

Ala Leu His Asn His Tyr Thr Gln Lys Ser Leu Ser Leu Ser Pro Gly
    690                 695                 700

Lys
705

<210> SEQ ID NO 33
<211> LENGTH: 453
<212> TYPE: PRT
<213> ORGANISM: Artificial
<220> FEATURE:
<223> OTHER INFORMATION: OAscFab2 -<VEGF> heavy chain

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285
```

```
Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Cys Thr Leu Pro Pro Ser Arg Asp Glu Leu Thr Lys Asn Gln
        355                 360                 365

Val Ser Leu Ser Cys Ala Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Val Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 34
<211> LENGTH: 214
<212> TYPE: PRT
<213> ORGANISM: Artificial
<220> FEATURE:
<223> OTHER INFORMATION: OAscFab2 -<VEGF> light chain

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

-continued

Ala Cys Glu Val Thr His Gln Gly Leu Ser Ser Pro Val Thr Lys Ser
            195                 200                 205

Phe Asn Arg Gly Glu Cys
    210

<210> SEQ ID NO 35
<211> LENGTH: 705
<212> TYPE: PRT
<213> ORGANISM: Artificial
<220> FEATURE:
<223> OTHER INFORMATION: OAscFab3 -<ANG2> peptide connected heavy chain
      and light chain

<400> SEQUENCE: 35

Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Cys Gly Thr Lys Val Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser Gly Gly Gly Ser Gly Gly Gly Gly Ser
    210                 215                 220

Gly Gly Gly Gly Ser Gly Gly Gly Ser Gly Gly Gly Ser Gly
225                 230                 235                 240

Gly Gly Gly Ser Gly Gly Gln Val Gln Leu Val Gln Ser Gly Ala Glu
                245                 250                 255

Val Lys Lys Pro Gly Ala Ser Val Lys Val Ser Cys Lys Ala Ser Gly
            260                 265                 270

Tyr Thr Phe Thr Gly Tyr Tyr Met His Trp Val Arg Gln Ala Pro Gly
        275                 280                 285

Gln Cys Leu Glu Trp Met Gly Trp Ile Asn Pro Asn Ser Gly Gly Thr
    290                 295                 300

Asn Tyr Ala Gln Lys Phe Gln Gly Arg Val Thr Met Thr Arg Asp Thr
305                 310                 315                 320

Ser Ile Ser Thr Ala Tyr Met Glu Leu Ser Arg Leu Arg Ser Asp Asp
                325                 330                 335

Thr Ala Val Tyr Tyr Cys Ala Arg Ser Pro Asn Pro Tyr Tyr Tyr Asp
              340                 345                 350

Ser Ser Gly Tyr Tyr Pro Gly Ala Phe Asp Ile Trp Gly Gln Gly
              355                 360                 365

Thr Met Val Thr Val Ser Ser Ala Ser Thr Lys Gly Pro Ser Val Phe
370                 375                 380

Pro Leu Ala Pro Ser Ser Lys Ser Thr Ser Gly Gly Thr Ala Ala Leu
385                 390                 395                 400

Gly Cys Leu Val Lys Asp Tyr Phe Pro Glu Pro Val Thr Val Ser Trp
              405                 410                 415

Asn Ser Gly Ala Leu Thr Ser Gly Val His Thr Phe Pro Ala Val Leu
              420                 425                 430

Gln Ser Ser Gly Leu Tyr Ser Leu Ser Ser Val Val Thr Val Pro Ser
              435                 440                 445

Ser Ser Leu Gly Thr Gln Thr Tyr Ile Cys Asn Val Asn His Lys Pro
450                 455                 460

Ser Asn Thr Lys Val Asp Lys Lys Val Glu Pro Lys Ser Cys Asp Lys
465                 470                 475                 480

Thr His Thr Cys Pro Pro Cys Pro Ala Pro Glu Leu Leu Gly Gly Pro
              485                 490                 495

Ser Val Phe Leu Phe Pro Pro Lys Pro Lys Asp Thr Leu Met Ile Ser
              500                 505                 510

Arg Thr Pro Glu Val Thr Cys Val Val Val Asp Val Ser His Glu Asp
              515                 520                 525

Pro Glu Val Lys Phe Asn Trp Tyr Val Asp Gly Val Glu Val His Asn
              530                 535                 540

Ala Lys Thr Lys Pro Arg Glu Glu Gln Tyr Asn Ser Thr Tyr Arg Val
545                 550                 555                 560

Val Ser Val Leu Thr Val Leu His Gln Asp Trp Leu Asn Gly Lys Glu
              565                 570                 575

Tyr Lys Cys Lys Val Ser Asn Lys Ala Leu Pro Ala Pro Ile Glu Lys
              580                 585                 590

Thr Ile Ser Lys Ala Lys Gly Gln Pro Arg Glu Pro Gln Val Tyr Thr
              595                 600                 605

Leu Pro Pro Cys Arg Asp Glu Leu Thr Lys Asn Gln Val Ser Leu Trp
610                 615                 620

Cys Leu Val Lys Gly Phe Tyr Pro Ser Asp Ile Ala Val Glu Trp Glu
625                 630                 635                 640

Ser Asn Gly Gln Pro Glu Asn Asn Tyr Lys Thr Thr Pro Pro Val Leu
              645                 650                 655

Asp Ser Asp Gly Ser Phe Phe Leu Tyr Ser Lys Leu Thr Val Asp Lys
              660                 665                 670

Ser Arg Trp Gln Gln Gly Asn Val Phe Ser Cys Ser Val Met His Glu
              675                 680                 685

Ala Leu His Asn His Tyr Thr Gln Lys Ser Leu Ser Leu Ser Pro Gly
              690                 695                 700

Lys
705

<210> SEQ ID NO 36
<211> LENGTH: 453
<212> TYPE: PRT
<213> ORGANISM: Artificial
<220> FEATURE:

<223> OTHER INFORMATION: OAscFab3 -<VEGF> heavy chain

<400> SEQUENCE: 36

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Tyr Thr Phe Thr Asn Tyr
            20                  25                  30
Gly Met Asn Trp Val Arg Gln Ala Pro Gly Lys Gly Leu Glu Trp Val
        35                  40                  45
Gly Trp Ile Asn Thr Tyr Thr Gly Glu Pro Thr Tyr Ala Ala Asp Phe
    50                  55                  60
Lys Arg Arg Phe Thr Phe Ser Leu Asp Thr Ser Lys Ser Thr Ala Tyr
65                  70                  75                  80
Leu Gln Met Asn Ser Leu Arg Ala Glu Asp Thr Ala Val Tyr Tyr Cys
                85                  90                  95
Ala Lys Tyr Pro His Tyr Tyr Gly Ser Ser His Trp Tyr Phe Asp Val
            100                 105                 110
Trp Gly Gln Gly Thr Leu Val Thr Val Ser Ser Ala Ser Thr Lys Gly
        115                 120                 125
Pro Ser Val Phe Pro Leu Ala Pro Ser Ser Lys Ser Thr Ser Gly Gly
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Lys Val Glu Pro Lys
    210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Cys Thr Leu Pro Pro Ser Arg Asp Glu Leu Thr Lys Asn Gln
        355                 360                 365
Val Ser Leu Ser Cys Ala Val Lys Gly Phe Tyr Pro Ser Asp Ile Ala
    370                 375                 380
Val Glu Trp Glu Ser Asn Gly Gln Pro Glu Asn Asn Tyr Lys Thr Thr
385                 390                 395                 400
```

```
Pro Pro Val Leu Asp Ser Asp Gly Ser Phe Phe Leu Val Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
            450

<210> SEQ ID NO 37
<211> LENGTH: 214
<212> TYPE: PRT
<213> ORGANISM: Artificial
<220> FEATURE:
<223> OTHER INFORMATION: OAscFab3 -<VEGF> light chain

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 38
<211> LENGTH: 708
<212> TYPE: PRT
<213> ORGANISM: Artificial
<220> FEATURE:
<223> OTHER INFORMATION: OAscXFab1 -<ANG2> peptide connected heavy chain
      and light chain

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
```

```
            20                  25                  30
Tyr Met His Trp Val Arg Gln Ala Pro Gly Gln Gly Leu Glu Trp Met
         35                  40                  45
Gly Trp Ile Asn Pro Asn Ser Gly Gly Thr Asn Tyr Ala Gln Lys Phe
 50                  55                  60
Gln Gly Arg Val Thr Met Thr Arg Asp Thr Ser Ile Ser Thr Ala Tyr
 65                  70                  75                  80
Met Glu Leu Ser Arg Leu Arg Ser Asp Asp Thr Ala Val Tyr Tyr Cys
                 85                  90                  95
Ala Arg Ser Pro Asn Pro Tyr Tyr Asp Ser Ser Gly Tyr Tyr Tyr
                100                 105                 110
Pro Gly Ala Phe Asp Ile Trp Gly Gln Gly Thr Met Val Thr Val Ser
                115                 120                 125
Ser Ala Ser Val Ala Ala Pro Ser Val Phe Ile Phe Pro Pro Ser Asp
            130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
            180                 185                 190
Ser Thr Tyr Ser Leu Ser Ser Thr Leu Thr Leu Ser Lys Ala Asp Tyr
        195                 200                 205
Glu Lys His Lys Val Tyr Ala Cys Glu Val Thr His Gln Gly Leu Ser
    210                 215                 220
Ser Pro Val Thr Lys Ser Phe Asn Arg Gly Glu Cys Gly Gly Gly Gly
225                 230                 235                 240
Ser Gly Gly Gly Gly Ser Gly Gly Gly Gly Ser Gly Gly Gly Gly Ser
                245                 250                 255
Gly Gly Gly Gly Ser Gly Gly Gly Ser Gly Gly Gln Pro Gly Leu
            260                 265                 270
Thr Gln Pro Pro Ser Val Ser Val Ala Pro Gly Gln Thr Ala Arg Ile
        275                 280                 285
Thr Cys Gly Gly Asn Asn Ile Gly Ser Lys Ser Val His Trp Tyr Gln
    290                 295                 300
Gln Lys Pro Gly Gln Ala Pro Val Leu Val Val Tyr Asp Asp Ser Asp
305                 310                 315                 320
Arg Pro Ser Gly Ile Pro Glu Arg Phe Ser Gly Ser Asn Ser Gly Asn
                325                 330                 335
Thr Ala Thr Leu Thr Ile Ser Arg Val Glu Ala Gly Asp Glu Ala Asp
            340                 345                 350
Tyr Tyr Cys Gln Val Trp Asp Ser Ser Asp His Tyr Val Phe Gly
        355                 360                 365
Thr Gly Thr Lys Val Thr Val Leu Ser Ser Ala Ser Thr Lys Gly Pro
    370                 375                 380
Ser Val Phe Pro Leu Ala Pro Ser Ser Lys Ser Thr Ser Gly Gly Thr
385                 390                 395                 400
Ala Ala Leu Gly Cys Leu Val Lys Asp Tyr Phe Pro Glu Pro Val Thr
                405                 410                 415
Val Ser Trp Asn Ser Gly Ala Leu Thr Ser Gly Val His Thr Phe Pro
            420                 425                 430
Ala Val Leu Gln Ser Ser Gly Leu Tyr Ser Leu Ser Ser Val Val Thr
        435                 440                 445
```

```
Val Pro Ser Ser Ser Leu Gly Thr Gln Thr Tyr Ile Cys Asn Val Asn
        450                 455                 460

His Lys Pro Ser Asn Thr Lys Val Asp Lys Lys Val Glu Pro Lys Ser
465                 470                 475                 480

Cys Asp Lys Thr His Thr Cys Pro Pro Cys Pro Ala Pro Glu Leu Leu
                485                 490                 495

Gly Gly Pro Ser Val Phe Leu Phe Pro Pro Lys Pro Lys Asp Thr Leu
            500                 505                 510

Met Ile Ser Arg Thr Pro Glu Val Thr Cys Val Val Val Asp Val Ser
        515                 520                 525

His Glu Asp Pro Glu Val Lys Phe Asn Trp Tyr Val Asp Gly Val Glu
    530                 535                 540

Val His Asn Ala Lys Thr Lys Pro Arg Glu Glu Gln Tyr Asn Ser Thr
545                 550                 555                 560

Tyr Arg Val Val Ser Val Leu Thr Val Leu His Gln Asp Trp Leu Asn
                565                 570                 575

Gly Lys Glu Tyr Lys Cys Lys Val Ser Asn Lys Ala Leu Pro Ala Pro
            580                 585                 590

Ile Glu Lys Thr Ile Ser Lys Ala Lys Gly Gln Pro Arg Glu Pro Gln
        595                 600                 605

Val Tyr Thr Leu Pro Pro Cys Arg Asp Glu Leu Thr Lys Asn Gln Val
    610                 615                 620

Ser Leu Trp Cys Leu Val Lys Gly Phe Tyr Pro Ser Asp Ile Ala Val
625                 630                 635                 640

Glu Trp Glu Ser Asn Gly Gln Pro Glu Asn Asn Tyr Lys Thr Thr Pro
                645                 650                 655

Pro Val Leu Asp Ser Asp Gly Ser Phe Phe Leu Tyr Ser Lys Leu Thr
            660                 665                 670

Val Asp Lys Ser Arg Trp Gln Gln Gly Asn Val Phe Ser Cys Ser Val
        675                 680                 685

Met His Glu Ala Leu His Asn His Tyr Thr Gln Lys Ser Leu Ser Leu
    690                 695                 700

Ser Pro Gly Lys
705

<210> SEQ ID NO 39
<211> LENGTH: 453
<212> TYPE: PRT
<213> ORGANISM: Artificial
<220> FEATURE:
<223> OTHER INFORMATION: OAscXFab1 -<VEGF> heavy chain

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95
```

```
Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Cys Thr Leu Pro Pro Ser Arg Asp Glu Leu Thr Lys Asn Gln
        355                 360                 365

Val Ser Leu Ser Cys Ala Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Val Ser Lys Leu
            405                 410                 415

Thr Val Asp Lys Ser Arg Trp Gln Gln Gly Asn Val Phe Ser Cys Ser
        420                 425                 430

Val Met His Glu Ala Leu His Asn His Tyr Thr Gln Lys Ser Leu Ser
    435                 440                 445

Leu Ser Pro Gly Lys
    450

<210> SEQ ID NO 40
<211> LENGTH: 214
<212> TYPE: PRT
<213> ORGANISM: Artificial
<220> FEATURE:
<223> OTHER INFORMATION: OAscXFab1 -<VEGF> light chain

<400> SEQUENCE: 40
```

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 41
<211> LENGTH: 708
<212> TYPE: PRT
<213> ORGANISM: Artificial
<220> FEATURE:
<223> OTHER INFORMATION: OAscXFab2 -<ANG2> peptide connected heavy chain
      and light chain

<400> SEQUENCE: 41

Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
```

```
            130                 135                 140
Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys Gly Gly Gly Ser Gly Gly Gly Gly Ser Gly
210                 215                 220

Gly Gly Gly Ser Gly Gly Gly Ser Gly Gly Gly Ser Gly Gly
225                 230                 235                 240

Gly Gly Ser Gly Gly Gln Val Gln Leu Val Gln Ser Gly Ala Glu Val
            245                 250                 255

Lys Lys Pro Gly Ala Ser Val Lys Val Ser Cys Lys Ala Ser Gly Tyr
                260                 265                 270

Thr Phe Thr Gly Tyr Tyr Met His Trp Val Arg Gln Ala Pro Gly Gln
            275                 280                 285

Gly Leu Glu Trp Met Gly Trp Ile Asn Pro Asn Ser Gly Gly Thr Asn
290                 295                 300

Tyr Ala Gln Lys Phe Gln Gly Arg Val Thr Met Thr Arg Asp Thr Ser
305                 310                 315                 320

Ile Ser Thr Ala Tyr Met Glu Leu Ser Arg Leu Arg Ser Asp Asp Thr
                325                 330                 335

Ala Val Tyr Tyr Cys Ala Arg Ser Pro Asn Pro Tyr Tyr Tyr Asp Ser
            340                 345                 350

Ser Gly Tyr Tyr Tyr Pro Gly Ala Phe Asp Ile Trp Gly Gln Gly Thr
        355                 360                 365

Met Val Thr Val Ser Ser Ala Ser Val Ala Ala Pro Ser Val Phe Ile
    370                 375                 380

Phe Pro Pro Ser Asp Glu Gln Leu Lys Ser Gly Thr Ala Ser Val Val
385                 390                 395                 400

Cys Leu Leu Asn Asn Phe Tyr Pro Arg Glu Ala Lys Val Gln Trp Lys
                405                 410                 415

Val Asp Asn Ala Leu Gln Ser Gly Asn Ser Gln Glu Ser Val Thr Glu
            420                 425                 430

Gln Asp Ser Lys Asp Ser Thr Tyr Ser Leu Ser Ser Thr Leu Thr Leu
        435                 440                 445

Ser Lys Ala Asp Tyr Glu Lys His Lys Val Tyr Ala Cys Glu Val Thr
450                 455                 460

His Gln Gly Leu Ser Ser Pro Val Thr Lys Ser Phe Asn Arg Gly Glu
465                 470                 475                 480

Cys Asp Lys Thr His Thr Cys Pro Pro Cys Pro Ala Pro Glu Leu Leu
                485                 490                 495

Gly Gly Pro Ser Val Phe Leu Phe Pro Pro Lys Pro Lys Asp Thr Leu
            500                 505                 510

Met Ile Ser Arg Thr Pro Glu Val Thr Cys Val Val Val Asp Val Ser
        515                 520                 525

His Glu Asp Pro Glu Val Lys Phe Asn Trp Tyr Val Asp Gly Val Glu
530                 535                 540

Val His Asn Ala Lys Thr Lys Pro Arg Glu Glu Gln Tyr Asn Ser Thr
545                 550                 555                 560
```

```
Tyr Arg Val Val Ser Val Leu Thr Val Leu His Gln Asp Trp Leu Asn
                565                 570                 575

Gly Lys Glu Tyr Lys Cys Lys Val Ser Asn Lys Ala Leu Pro Ala Pro
            580                 585                 590

Ile Glu Lys Thr Ile Ser Lys Ala Lys Gly Gln Pro Arg Glu Pro Gln
        595                 600                 605

Val Tyr Thr Leu Pro Pro Cys Arg Asp Glu Leu Thr Lys Asn Gln Val
    610                 615                 620

Ser Leu Trp Cys Leu Val Lys Gly Phe Tyr Pro Ser Asp Ile Ala Val
625                 630                 635                 640

Glu Trp Glu Ser Asn Gly Gln Pro Glu Asn Asn Tyr Lys Thr Thr Pro
                645                 650                 655

Pro Val Leu Asp Ser Asp Gly Ser Phe Phe Leu Tyr Ser Lys Leu Thr
            660                 665                 670

Val Asp Lys Ser Arg Trp Gln Gln Gly Asn Val Phe Ser Cys Ser Val
        675                 680                 685

Met His Glu Ala Leu His Asn His Tyr Thr Gln Lys Ser Leu Ser Leu
    690                 695                 700

Ser Pro Gly Lys
705

<210> SEQ ID NO 42
<211> LENGTH: 453
<212> TYPE: PRT
<213> ORGANISM: Artificial
<220> FEATURE:
<223> OTHER INFORMATION: OAscXFab2 -<VEGF> heavy chain

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205
```

```
Asn His Lys Pro Ser Asn Thr Lys Val Asp Lys Lys Val Glu Pro Lys
            210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Cys Thr Leu Pro Pro Ser Arg Asp Glu Leu Thr Lys Asn Gln
        355                 360                 365

Val Ser Leu Ser Cys Ala Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Val Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 43
<211> LENGTH: 214
<212> TYPE: PRT
<213> ORGANISM: Artificial
<220> FEATURE:
<223> OTHER INFORMATION: OAscXFab2 -<VEGF> light chain

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
            210

<210> SEQ ID NO 44
<211> LENGTH: 705
<212> TYPE: PRT
<213> ORGANISM: Artificial
<220> FEATURE:
<223> OTHER INFORMATION: OAscXFab3 -<ANG2> peptide connected heavy chain
      and light chain

<400> SEQUENCE: 44

Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu Gly Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205

Pro Lys Ser Cys Gly Gly Gly Gly Ser Gly Gly Gly Gly Ser Gly Gly
    210                 215                 220

Gly Gly Ser Gly Gly Gly Gly Ser Gly Gly Gly Gly Ser Gly Gly Gly
225                 230                 235                 240

Gly Ser Gly Gly Gln Val Gln Leu Val Gln Ser Gly Ala Glu Val Lys
```

```
              245                 250                 255
Lys Pro Gly Ala Ser Val Lys Val Ser Cys Lys Ala Ser Gly Tyr Thr
            260                 265                 270

Phe Thr Gly Tyr Tyr Met His Trp Val Arg Gln Ala Pro Gly Gln Gly
        275                 280                 285

Leu Glu Trp Met Gly Trp Ile Asn Pro Asn Ser Gly Gly Thr Asn Tyr
    290                 295                 300

Ala Gln Lys Phe Gln Gly Arg Val Thr Met Thr Arg Asp Thr Ser Ile
305                 310                 315                 320

Ser Thr Ala Tyr Met Glu Leu Ser Arg Leu Arg Ser Asp Asp Thr Ala
                325                 330                 335

Val Tyr Tyr Cys Ala Arg Ser Pro Asn Pro Tyr Tyr Asp Ser Ser
            340                 345                 350

Gly Tyr Tyr Tyr Pro Gly Ala Phe Asp Ile Trp Gly Gln Gly Thr Met
        355                 360                 365

Val Thr Val Ser Gly Gln Pro Lys Ala Ala Pro Ser Val Thr Leu Phe
    370                 375                 380

Pro Pro Ser Ser Glu Glu Leu Gln Ala Asn Lys Ala Thr Leu Val Cys
385                 390                 395                 400

Leu Ile Ser Asp Phe Tyr Pro Gly Ala Val Thr Val Ala Trp Lys Ala
                405                 410                 415

Asp Ser Ser Pro Val Lys Ala Gly Val Glu Thr Thr Thr Pro Ser Lys
            420                 425                 430

Gln Ser Asn Asn Lys Tyr Ala Ala Ser Ser Tyr Leu Ser Leu Thr Pro
        435                 440                 445

Glu Gln Trp Lys Ser His Arg Ser Tyr Ser Cys Gln Val Thr His Glu
    450                 455                 460

Gly Ser Thr Val Glu Lys Thr Val Ala Pro Thr Glu Cys Ser Asp Lys
465                 470                 475                 480

Thr His Thr Cys Pro Pro Cys Pro Ala Pro Glu Leu Leu Gly Gly Pro
                485                 490                 495

Ser Val Phe Leu Phe Pro Pro Lys Pro Lys Asp Thr Leu Met Ile Ser
            500                 505                 510

Arg Thr Pro Glu Val Thr Cys Val Val Val Asp Val Ser His Glu Asp
        515                 520                 525

Pro Glu Val Lys Phe Asn Trp Tyr Val Asp Gly Val Glu Val His Asn
    530                 535                 540

Ala Lys Thr Lys Pro Arg Glu Glu Gln Tyr Asn Ser Thr Tyr Arg Val
545                 550                 555                 560

Val Ser Val Leu Thr Val Leu His Gln Asp Trp Leu Asn Gly Lys Glu
                565                 570                 575

Tyr Lys Cys Lys Val Ser Asn Lys Ala Leu Pro Ala Pro Ile Glu Lys
            580                 585                 590

Thr Ile Ser Lys Ala Lys Gly Gln Pro Arg Glu Pro Gln Val Tyr Thr
        595                 600                 605

Leu Pro Pro Cys Arg Asp Glu Leu Thr Lys Asn Gln Val Ser Leu Trp
    610                 615                 620

Cys Leu Val Lys Gly Phe Tyr Pro Ser Asp Ile Ala Val Glu Trp Glu
625                 630                 635                 640

Ser Asn Gly Gln Pro Glu Asn Asn Tyr Lys Thr Thr Pro Pro Val Leu
                645                 650                 655

Asp Ser Asp Gly Ser Phe Phe Leu Tyr Ser Lys Leu Thr Val Asp Lys
            660                 665                 670
```

-continued

```
Ser Arg Trp Gln Gln Gly Asn Val Phe Ser Cys Ser Val Met His Glu
        675                 680                 685
Ala Leu His Asn His Tyr Thr Gln Lys Ser Leu Ser Leu Ser Pro Gly
        690                 695                 700
Lys
705

<210> SEQ ID NO 45
<211> LENGTH: 453
<212> TYPE: PRT
<213> ORGANISM: Artificial
<220> FEATURE:
<223> OTHER INFORMATION: OAscXFab3 -<VEGF> heavy chain

<400> SEQUENCE: 45

Glu Val Gln Leu Val Glu Ser Gly Gly Gly Leu Val Gln Pro Gly Gly
1               5                   10                  15
Ser Leu Arg Leu Ser Cys Ala Ala Ser Gly Tyr Thr Phe Thr Asn Tyr
            20                  25                  30
Gly Met Asn Trp Val Arg Gln Ala Pro Gly Lys Gly Leu Glu Trp Val
        35                  40                  45
Gly Trp Ile Asn Thr Tyr Thr Gly Glu Pro Thr Tyr Ala Ala Asp Phe
    50                  55                  60
Lys Arg Arg Phe Thr Phe Ser Leu Asp Thr Ser Lys Ser Thr Ala Tyr
65                  70                  75                  80
Leu Gln Met Asn Ser Leu Arg Ala Glu Asp Thr Ala Val Tyr Tyr Cys
                85                  90                  95
Ala Lys Tyr Pro His Tyr Tyr Gly Ser Ser His Trp Tyr Phe Asp Val
            100                 105                 110
Trp Gly Gln Gly Thr Leu Val Thr Val Ser Ser Ala Ser Thr Lys Gly
        115                 120                 125
Pro Ser Val Phe Pro Leu Ala Pro Ser Ser Lys Ser Thr Ser Gly Gly
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Lys Val Glu Pro Lys
    210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
```

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Cys Thr Leu Pro Pro Ser Arg Asp Glu Leu Thr Lys Asn Gln
        355                 360                 365

Val Ser Leu Ser Cys Ala Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Val Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 46
<211> LENGTH: 214
<212> TYPE: PRT
<213> ORGANISM: Artificial
<220> FEATURE:
<223> OTHER INFORMATION: OAscXFab3 -<VEGF> light chain

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 47
<211> LENGTH: 191
<212> TYPE: PRT
<213> ORGANISM: Homo sapiens

<400> SEQUENCE: 47

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190
```

<210> SEQ ID NO 48
<211> LENGTH: 504
<212> TYPE: PRT
<213> ORGANISM: Artificial
<220> FEATURE:
<223> OTHER INFORMATION: Human angiopoietin-2 (ANG-2) with leader and
      His-tag

<400> SEQUENCE: 48

```
Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Pro Tyr Val Ser Asn Ala
    50                  55                  60

Val Gln Arg Asp Ala Pro Leu Glu Tyr Asp Asp Ser Val Gln Arg Leu
65                  70                  75                  80

Gln Val Leu Glu Asn Ile Met Glu Asn Asn Thr Gln Trp Leu Met Lys
                85                  90                  95

Leu Glu Asn Tyr Ile Gln Asp Asn Met Lys Lys Glu Met Val Glu Ile
            100                 105                 110

Gln Gln Asn Ala Val Gln Asn Gln Thr Ala Val Met Ile Glu Ile Gly
        115                 120                 125
```

```
Thr Asn Leu Leu Asn Gln Thr Ala Glu Gln Thr Arg Lys Leu Thr Asp
    130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
        195                 200                 205

Ile Lys Glu Glu Lys Asp Gln Leu Gln Val Leu Val Ser Lys Gln Asn
    210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Glu Thr Val Asn
                245                 250                 255

Asn Leu Leu Thr Met Met Ser Thr Ser Asn Ser Ala Lys Asp Pro Thr
            260                 265                 270

Val Ala Lys Glu Glu Gln Ile Ser Phe Arg Asp Cys Ala Glu Val Phe
        275                 280                 285

Lys Ser Gly His Thr Thr Asn Gly Ile Tyr Thr Leu Thr Phe Pro Asn
    290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
            340                 345                 350

Tyr Trp Leu Gly Asn Glu Phe Val Ser Gln Leu Thr Asn Gln Gln Arg
        355                 360                 365

Tyr Val Leu Lys Ile His Leu Lys Asp Trp Glu Gly Asn Glu Ala Tyr
    370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
                405                 410                 415

Ser Gln Pro Gly Asn Asp Phe Ser Thr Lys Asp Gly Asp Asn Asp Lys
            420                 425                 430

Cys Ile Cys Lys Cys Ser Gln Met Leu Thr Gly Gly Trp Trp Phe Asp
        435                 440                 445

Ala Cys Gly Pro Ser Asn Leu Asn Gly Met Tyr Tyr Pro Gln Arg Gln
    450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495

Ser Gly His His His His His His
            500

<210> SEQ ID NO 49
<211> LENGTH: 19
<212> TYPE: PRT
<213> ORGANISM: Artificial
<220> FEATURE:
```

```
<223> OTHER INFORMATION: leader peptide

<400> SEQUENCE: 49

Met Gly Trp Ser Cys Ile Ile Leu Phe Leu Val Ala Thr Ala Thr Gly
1               5                   10                  15

Val His Ser
```